United States Patent
Nirogi et al.

(10) Patent No.: US 12,391,698 B2
(45) Date of Patent: Aug. 19, 2025

(54) SUBSTITUTED PIPERIDINES AND PIPERAZINES AND METHODS FOR THE TREATMENT OF CNS DISORDERS

(71) Applicant: SUVEN LIFE SCIENCES LIMITED, Hyderabad-Telangana (IN)

(72) Inventors: Ramakrishna Nirogi, Hyderabad (IN); Abdul Rasheed Mohammed, Hyderabad (IN); Anil Karbhari Shinde, Hyderabad (IN); Narsimha Bogaraju, Hyderabad (IN); Vinod Kumar Goyal, Hyderabad (IN); Santosh Kumar Pandey, Hyderabad (IN); Vijay Sidram Benade, Hyderabad (IN); Pradeep Jayarajan, Hyderabad (IN); Ramkumar Subramanian, Hyderabad (IN); Venkateswarlu Jasti, Hyderabad (IN)

(73) Assignee: SUVEN LIFE SCIENCES LIMITED, Hyderabad-Telangana (IN)

( * ) Notice: Subject to any disclaimer, the term of this patent is extended or adjusted under 35 U.S.C. 154(b) by 0 days.

(21) Appl. No.: 18/721,449

(22) PCT Filed: Jan. 11, 2023

(86) PCT No.: PCT/IB2023/050245
§ 371 (c)(1),
(2) Date: Jun. 18, 2024

(87) PCT Pub. No.: WO2023/135528
PCT Pub. Date: Jul. 20, 2023

(65) Prior Publication Data
US 2025/0092049 A1 Mar. 20, 2025

(30) Foreign Application Priority Data
Jan. 11, 2022 (IN) .............................. 202241001563

(51) Int. Cl.
| | |
|---|---|
| *A61K 31/4523* | (2006.01) |
| *A61K 31/496* | (2006.01) |
| *A61K 31/519* | (2006.01) |
| *A61P 25/00* | (2006.01) |
| *A61P 25/14* | (2006.01) |
| *A61P 25/28* | (2006.01) |
| *C07D 241/04* | (2006.01) |
| *C07D 401/14* | (2006.01) |
| *C07D 487/04* | (2006.01) |

(52) U.S. Cl.
CPC .......... *C07D 487/04* (2013.01); *A61K 31/519* (2013.01); *A61P 25/00* (2018.01); *A61P 25/14* (2018.01); *A61P 25/28* (2018.01)

(58) Field of Classification Search
CPC .............. A61K 31/4523; A61K 31/496; C07D 241/04; C07D 401/14
USPC .............. 514/252.13, 326; 544/359; 546/207
See application file for complete search history.

(56) References Cited

FOREIGN PATENT DOCUMENTS

| | | |
|---|---|---|
| CN | 105367565 A | 3/2016 |
| EP | 0453042 A1 | 10/1991 |
| EP | 0464846 A1 | 1/1992 |
| JP | H0733744 | 2/1995 |
| JP | H09268188 A | 10/1997 |
| WO | 1996006846 | 3/1996 |
| WO | 2006069993 | 7/2006 |
| WO | WO-2023135528 A1 * | 7/2023 ........... A61K 31/519 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag Gmbh & Co. KGaA, 2005, Preface.*
Hackam, et al. JAMA, 296(14), 2006, 1731-1732.*
Herold F et al, "Synthesis of new hexahydro- and octahydropyrido[1,2-c]pyrimidine derivatives with an arylpiperazine moiety as ligands for 5-HT1A and 5-HT2A receptors", II Farmaco, vol. 57, Dec. 2002, pp. 959-971.
Herold F et al, "Synthesis of new hexahydro-and octahydropyrido[1,2-c]pyrimidine derivatives with an arylpiperazine moiety as ligands for 5-HT1A and 5-HT2A receptors, part 2", Pharmazie (Germany) Feb. 2004, vol. 59(2), p. 99-105.
Zareba Przemyslaw et al., "Chemical puzzles in the search for new, flexible derivatives of lurasidone as antipsychotic drugs", Bioorganic Medicinal Chem. (Elsevier, Amsterdam, NL) Mar. 29, 2020, vol. 28, No. 10, Article in Press (13 pages).
Lopez-Rodriguez M L et al, "Synthesis and Structure-Activity Relationships of a New Model of Arylpiperazines. 8.Computational Simulation of Ligand-Receptor Interaction of 5-HT1AR Agonists with Selectivity over alpha1-Adrenoceptors", Journal of Medicinal Chemistry, American Chemical Society, US, vol. 48, No. 7, Mar. 12, 2005, pp. 2548-2558.

(Continued)

*Primary Examiner* — Douglas M Willis
(74) *Attorney, Agent, or Firm* — IPHORGAN LTD

(57) ABSTRACT

The present invention relates to heteroalicyclic compounds represented by the general formula (I), or their isotopic forms, stereoisomers, or pharmaceutically acceptable salts thereof. The present invention also describes a method of making such compounds, pharmaceutical compositions comprising such compounds and their use for the treatment or prevention of central nervous system related disorders.

15 Claims, 3 Drawing Sheets

(56) References Cited

OTHER PUBLICATIONS

Lopez-Rodriguez M L et al, "Synthesis of new (benzimidazolyl)piperazines with affinity for the 5-HT"1"A receptor via Pd(0) amination of bromobenzimidazoles", Bioorganic & Medicinal Chemistry Letters, Elsevier, Amsterdam NL, vol. 9, No. 16, Aug. 16, 1999, pp. 2339-2342.

Yevich J P et al, "Synthesis and Biological Evaluation of 1-(1,2-Benzisothiazol-3-YL)-and (1,2-Benzisoxazol-3-YL)Piperazine Derivatives as Potential Antipsychotic Agents", Journal of Medicinal Chemistry, American Chemical Society, US, vol. 29, No. 3, Mar. 1986, pp. 359-369.

New J S et al, "The Thieno[3,2-C]Pyridine and Furo[3,2-C]Pyridine Rings: New Pharmacophores With Potential Antipsychotic Activity", Journal of Medicinal Chemistry, American Chemical Society, US, vol. 32, Jun. 1989, pp. 1147-1156.

European Patent Office, "International Search Report" issued Mar. 22, 2023 in PCT Appln. PCT/IB2023/050245.

European Patent Office, "Written Opinion" issued Mar. 22, 2023 in PCT Appln. PCT/IB2023/050245.

European Patent Office, "International Preliminary Report on Patentability" issued Dec. 13, 2023 in PCT Appln. PCT/IB2023/050245.

Suven Life Sciences Ltd., "Response to Written Opinion" filed May 22, 2023 in PCT Appln. PCT/IB2023/050245 (provided in two pdfs with this IDS Form).

Blair et al., "Extrapyramidal symptoms are serious side effects of antipsychotic and other drugs" Nurse Practitioner, vol. 17, No. 11 (Nov. 1992), pp. 56,62,63,64,67.

Kusumi et al., "Psychopharmacology of atypical antipsychotic drugs: From the receptor binding profile to neuroprotection and neurogenesis" Psychiatry and Clinical Neurosciences 69:243-258 (2015).

Madhubhashinee et al., "Antipsychotic-associated weight gain: management strategies and impact on treatment adherence" Neuropsychiatric Disease and Treatment (2017) 13:2231-2241.

Miller et al., "Atypical Antispychotics: Sleep, Sedation, and Efficacy" Prim Care Companion J. Clin. Psychiatry (2004) 6 [Supp 2]:3-7.

Ferrarelli et al., "Protecting cognition from antipsychotics" Science Signalling (2017) 10:498 (provided as 4 page pdf).

Ichikawa et al., "Structural Insight into Receptor-Selectivity for Lurasidone" Neurochem. Intl. 61:1133-1143 (2012).

* cited by examiner

Values are expressed mean ± SEM (n=4/ group). $^{\#\#}p<0.001$ Vs vehicle alone, $***p<0.001$ Vs reserpine, $^{\wedge\wedge}p<0.01$ Vs apomorphine.

Values are expressed mean ± SEM. $***p<0.001$ Vs vehicle (Bonferroni's post test).

Values are expressed mean ± SEM. $*p<0.05$, $p<0.01$, $*p<0.001$ Vs vehicle (Bonferroni's post test).

Values are expressed mean ± SEM

Values are expressed mean ± SEM.

SUBSTITUTED PIPERIDINES AND PIPERAZINES AND METHODS FOR THE TREATMENT OF CNS DISORDERS

CROSS REFERENCE TO RELATED APPLICATIONS

This application is a national stage completion application of PCT Application No. PCT/IB2023/050245, filed Jan. 11, 2023, and claims priority from India Application No. 202241001563, filed Jan. 11, 2022. Each of these applications is incorporated by reference herein in its entirety.

FIELD OF THE INVENTION

The invention relates to heteroalicyclic compounds represented by the general formula (I), or their isotopic forms, stereoisomers, or pharmaceutically acceptable salts thereof. The present invention also describes a method of making such compounds, pharmaceutical compositions comprising such compounds and their use for the treatment or prevention of central nervous system related disorders.

BACKGROUND OF THE INVENTION

A class of medication primarily used to manage psychosis (including delusions, hallucinations, paranoia or disordered thought) in schizophrenia and bipolar disorder are known as antipsychotics. They are divided into first-generation antipsychotics (or typical antipsychotics) and second-generation drugs (or atypical antipsychotics). Antipsychotics are most frequently used for various central nervous system (CNS) disorders like schizophrenia, bipolar disorder, Tourette syndrome, psychotic depression, treatment-resistant depression, agitation or psychosis associated with dementia, and the like (https://www.ncbi.nlm.nih.gov/books/NBK519503).

WO2006069993 disclosed arylpiperazine derivatives as 5-$HT_{1A}$ receptor subtype ligands. WO1996006846 discloses arylpiperazine derivatives as 5-$HT_{1A}$ ligands for the treatment of central nervous system disorders.

EP0453042 discloses novel 2,9-disubstituted-4H-pyrido-[1,2-a]pyrimidin-4-ones having dopamine and serotonin antagonistic activity.

EP0464846 discloses imide derivatives having affinity at dopamine $D_2$ receptor. CN105367565 discloses piperazine (piperidine) cyclohexyl derivatives have affinity at dopamine $D_2$ receptor, a dopamine $D_3$ receptor, a serotonin 5-$HT_{1A}$ receptor and a serotonin 5-$HT_{2A}$ receptor.

M. L. Lopez-Rodriguez et al. discloses (benzimidazolyl) piperazine compounds as 5-$HT_{1A}$ receptor ligands (*Bioorg. Med. Chem. Lett.* 9 (1999) 2339-2342). O. Ichikawa et al. discloses Lurasidone that has affinity for dopamine $D_2$, 5-hydroxyltryptamine 5-$HT_{2A}$, and 5-$HT_7$ receptors (*Neurochemistry International* 61 (2012) 1133-1143).

The compounds of the present invention show multiple pharmacological effects which is desirable so as to have a wide treatment spectrum as the causal factors for schizophrenia, bipolar disorders, mood disorders, emotional disorders are of heterogeneous in nature.

The long-term use of antipsychotics is associated with side effects such as involuntary movement disorders, cognitive dulling, gynecomastia, metabolic syndrome, and tardive dyskinesia (TD). TD causes involuntary movements of the tongue, lips, face, trunk, and extremities that occur in patients treated with long-term antipsychotics. Antipsychotics are also associated with increased mortality in elderly people with dementia. Therefore, there is an unmet need and scope to discover and develop a novel antipsychotic with improved therapeutic target selectivity, acceptable tolerability and safety profile for the treatment of schizophrenia and other CNS related disorders.

The objective of the present invention is to provide a drug which works on CNS and has a wider treatment option, minimal side effects and very good safety margin as compared to typical and atypical antipsychotic drugs known in the literature. The focused and intensive research to achieve above said objective yielded heteroalicyclic substituted piperazine and piperidine derivatives. These derivatives exhibit activity as antagonists of dopamine $D_2$ receptors, antagonists of 5-$HT_{1A}$ receptors, antagonists of 5-$HT_{2A}$ receptors and antagonists of 5-$HT_7$ receptors and further inhibits serotonin reuptake.

The heteroalicyclic substituted piperazine and piperidine compounds of the present invention, in addition to showing efficacy in animal models of schizophrenia and related diseases, also attenuates associated cognitive deficit and showed lesser propensity to induce side effects like extrapyramidal side effects, involuntary movements and tardive dyskinesia.

SUMMARY OF THE INVENTION

In first aspect, in the present invention provided is a heteroalicyclic piperazine or piperidine derivative represented by a compound of formula (I), or an isotopic form, a stereoisomer, or a pharmaceutically acceptable salt thereof,

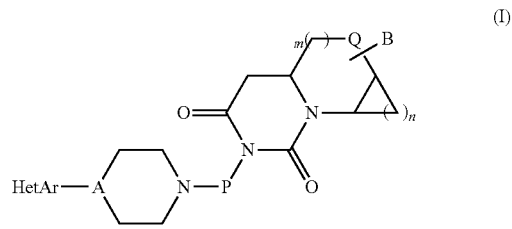

wherein,
HetAr is selected from,

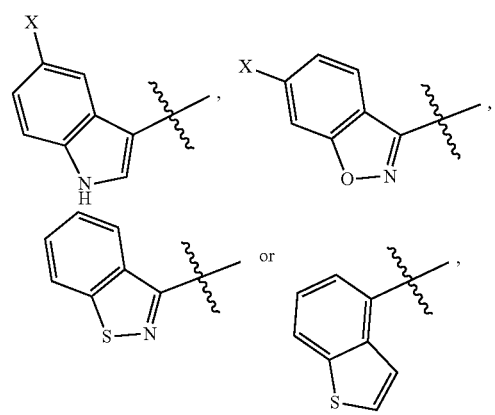

wherein X is hydrogen, halogen or alkoxy;

" $\sim\!\!\sim\!\!\sim$ " represents the point of attachment;

P is —(CH$_2$)$_b$—, or

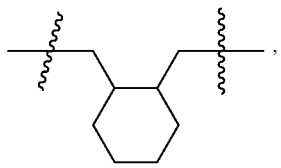

wherein b is an integer from 2 to 6;
A is CH or N;
n is 0 or 1; m is 0 or 1;
Q is —CH$_2$—, O, NH, N-Alkyl, —N(COR)—, or —N(COOR)—, wherein R is alkyl, alkoxyalkyl, cycloalkyl or alkylaryl; and
B is hydrogen, halogen or alkoxy; provided Q is CH$_2$ then B can be hydrogen, halogen or alkoxy.

In another aspect, the present invention relates to processes for the preparation of the compound of formula (I) or an isotopic form, a stereoisomer, or a pharmaceutically acceptable salt thereof.

In another aspect, the present invention relates to a pharmaceutical composition comprising a therapeutically effective amount of the compound of formula (I), or an isotopic form, a stereoisomer, or a pharmaceutically acceptable salt thereof, and pharmaceutically acceptable excipients.

DETAILED DESCRIPTION OF THE INVENTION

Figure 1:
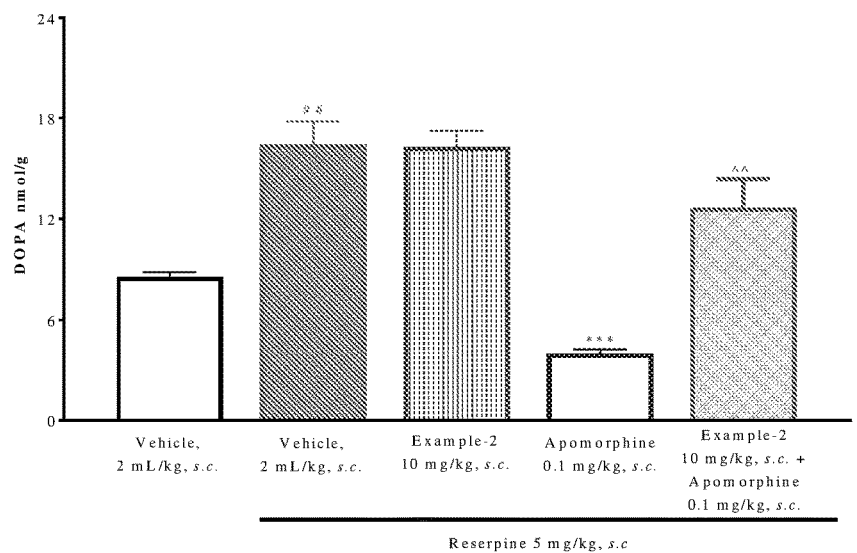
FIG. 1: Reserpine induced dihydroxyphenylalanine (DOPA) accumulation assay

Unless otherwise stated, the following terms used in the specification and claims have the meanings given below:

The term, "alkyl" as used herein refers to branched or straight-chain aliphatic hydrocarbon. Examples of alkyl include methyl, ethyl, n-propyl, isopropyl, n-butyl, isobutyl, sec-butyl and tert-butyl.

The term "alkoxy" as used herein refers to an alkyl group bonded to the oxygen atom. Examples of the alkoxy include methoxy, ethoxy, propyloxy, and butyloxy.

The term, "alkoxyalkyl" as used herein refers to alkyl and alkoxy group defined above bonded together by oxygen atom. Examples of alkoxyalkyl include methoxymethyl, methoxyethyl, ethoxymethyl, ethoxypropyl, methoxypropyl and the like.

The term, "alkylaryl" as used herein refers to alkyl as defined above attached with aryl group. Examples of alkylaryl include, benzyl, phenethyl, pyridylethyl, pyridylpropyl and the like.

The term, "cycloalkyl" as used herein refers to a saturated monocyclic hydrocarbon ring containing from three to six carbon atoms. Examples of the cycloalkyl group include cyclopropyl, cyclobutyl, cyclopentyl and cyclohexyl.

The term, "halogen" as used herein refers to fluorine, chlorine, bromine or iodine. Preferably, halogen is fluorine, chlorine or bromine.

The term, "isotopic form" as used herein refers to the compound of formula (I) wherein one or more atoms of compound of formula (I) are substituted by their respective isotopes. For example, isotopes of hydrogen include $^2$H (deuterium) and $^3$H (tritium), isotopes of carbon included $^{11}$C, $^{14}$C, and isotope of iodine includes $^{123}$I, and isotope of fluorine includes $^{18}$F.

The term, "stereoisomer" as used herein refers to isomers of a compound of formula (I) that differ in the arrangement of their atoms in space. Compounds disclosed herein may exist as a single stereoisomer, racemates and/or mixtures of enantiomers and/or diastereomers. All such single stereoisomer, racemates and mixtures thereof are intended to be within the scope of the present invention.

The term, "pharmaceutically acceptable salt" as used herein refers to salts of the active compound i.e. the compound of formula (I), and are prepared by reaction with the appropriate acid or acid derivative, depending on the particular substituents found on the compounds described herein.

The phrase, "therapeutically effective amount" is defined as an amount of a compound of the present invention that (i) treats the particular disease, condition or disorder (ii) eliminates one or more symptoms of the particular disease, condition or disorder (iii) delays the onset of one or more symptoms of the particular disease, condition or disorder described herein.

The term, "patient" as used herein refers to an animal. Preferably the term "patient" refers to a mammal. The term mammal includes animals such as mice, rats, dogs, rabbits, pigs, monkeys, horses, pigeons, *Xenopus laevis*, zebrafish, guinea pigs, elephant, camel, chimpanzee and humans. More preferably the patient is human.

Embodiments

The present invention encompasses all the compounds described by the compound of formula (I) without any limitation, however, preferred aspects and elements of the invention are discussed herein in the form of the following embodiments.

In one embodiment, the present invention relates to the compound of formula (Ia) derived from the compound of formula (I),

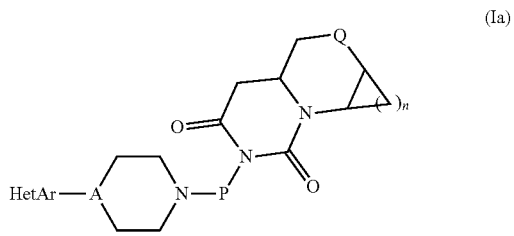

(Ia)

or an isotopic form, a stereoisomer, or a pharmaceutically acceptable salt thereof;
wherein, HetAr, A, P, Q and n are as defined in the first aspect.

In another embodiment, the present invention relates to the compound of formula (Ib) derived from the compound of formula (I),

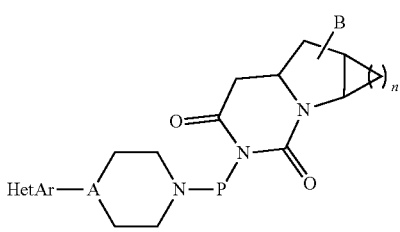

(Ib)

or an isotopic form, a stereoisomer, or a pharmaceutically acceptable salt thereof;

wherein, B is hydrogen or halogen; n is 0 or 1; provided that B is hydrogen or halogen when n is 0; HetAr, A, and P are as defined in the first aspect.

In some embodiments, the group HetAr is

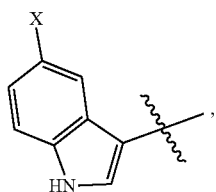

wherein X is hydrogen, alkoxy or halogen.

In some embodiments, the group HetAr is

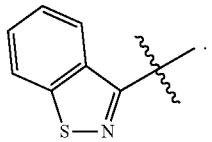 [SMILES: *c1nsc2ccccc12]

In some embodiments, the group HetAr is

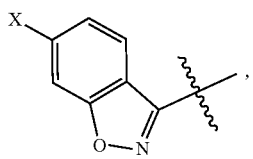

wherein X is hydrogen or halogen.

In some embodiments, the group HetAr is

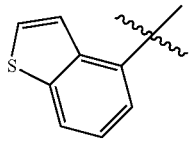

In some embodiments, the group B is hydrogen or halogen.

In another embodiment, the preferred compound of the invention is selected from:

2-[4-(4-Benzo[d]isothiazol-3-yl-piperazin-1-yl)-butyl]-tetrahydro-pyrrolo[1,2-c]pyrimidine-1,3-dione;

2-[4-(4-Benzo[d]isothiazol-3-yl-piperazin-1-yl)-butyl]-tetrahydro-pyrrolo[1,2-c]pyrimidine-1,3-dione oxalate;

2-[4-(4-Benzo[b]thiophen-4-yl-piperazin-1-yl)-butyl]-tetrahydro-pyrrolo[1,2-c]pyrimidine-1,3-dione;

2-[4-(4-Benzo[b]thiophen-4-yl-piperazin-1-yl)-butyl]-tetrahydro-pyrrolo[1,2-c]pyrimidine-1,3-dione oxalate;

2-{4-[4-(6-Fluoro-benzo[d]isoxazol-3-yl)-piperidin-1-yl]-butyl}-tetrahydro-pyrrolo[1,2-c]pyrimidine-1,3-dione;

2-{4-[4-(5-Fluoro-1H-indol-3-yl)-piperidin-1-yl]-butyl}-tetrahydro-pyrrolo[1,2-c]pyrimidine-1,3-dione;

2-{4-[4-(5-Fluoro-1H-indol-3-yl)-piperidin-1-yl]-butyl}-tetrahydro-pyrrolo[1,2-c]pyrimidine-1,3-dione oxalate;

2-[4-(4-Benzo[d]isothiazol-3-yl-piperazin-1-yl)-butyl]-6-fluoro-tetrahydro-pyrrolo[1,2-c]pyrimidine-1,3-dione;

2-[4-(4-Benzo[d]isothiazol-3-yl-piperazin-1-yl)-butyl]-6-fluoro-tetrahydro-pyrrolo[1,2-c]pyrimidine-1,3-dione oxalate;

3-[4-(4-Benzo[d]isothiazol-3-yl-piperazin-1-yl)-butyl]-hexahydro-1b,3-diaza-cyclopropa[a]indene-2,4-dione;

3-[4-(4-Benzo[d]isothiazol-3-yl-piperazin-1-yl)-butyl]-hexahydro-1b,3-diaza-cyclopropa[a]indene-2,4-dione oxalate;

2-[4-(4-Benzo[d]isothiazol-3-yl-piperazin-1-yl)-butyl]-hexahydro-pyrido[1,2-c]pyrimidine-1,3-dione;

2-{4-[4-(6-Fluoro-benzo[d]isoxazol-3-yl)-piperidin-1-yl]-butyl}-hexahydro-pyrido[1,2-c]pyrimidine-1,3-dione;

2-{4-[4-(6-Fluoro-benzo[d]isoxazol-3-yl)-piperidin-1-yl]-butyl}-hexahydro-pyrido[1,2-c]pyrimidine-1,3-dione fumarate;

2-{4-[4-(5-Fluoro-1H-indol-3-yl)-piperidin-1-yl]-butyl}-hexahydro-pyrido[1,2-c]pyrimidine-1,3-dione;

2-{4-[4-(5-Methoxy-1H-indol-3-yl)-piperidin-1-yl]-butyl}-hexahydro-pyrido[1,2-c]pyrimidine-1,3-dione;

7-[4-(4-Benzo[d]isothiazol-3-yl-piperazin-1-yl)-butyl]-tetrahydro-pyrimido[6,1-c][1,4]oxazine-6,8-dione;

7-[4-(4-Benzo[d]isothiazol-3-yl-piperazin-1-yl)-butyl]-tetrahydro-pyrimido[6,1-c][1,4]oxazine-6,8-dione oxalate;

7-[4-(4-Benzo[d]isothiazol-3-yl-piperazin-1-yl)-butyl]-6,8-dioxo-octahydro-pyrazino[1,2-c]pyrimidine-2-carboxylic acid benzyl ester;

7-[4-(4-Benzo[d]isothiazol-3-yl-piperazin-1-yl)-butyl]-6,8-dioxo-octahydro-pyrazino[1,2-c]pyrimidine-2-carboxylic acid benzyl ester fumarate;

7-{4-[4-(6-Fluoro-benzo[d]isoxazol-3-yl)-piperidin-1-yl]-butyl}-6,8-dioxo-octahydro-pyrazino[1,2-c]pyrimidine-2-carboxylic acid benzyl ester;

7-{4-[4-(6-Fluoro-benzo[d]isoxazol-3-yl)-piperidin-1-yl]-butyl}-6,8-dioxo-octahydro-pyrazino[1,2-c]pyrimidine-2-carboxylic acid benzyl ester fumarate;

2-[3-(4-benzo[d]isothiazol-3-yl-piperazin-1-yl)-propyl]-tetrahydro-pyrrolo[1,2-c]pyrimidine-1,3-dione;

2-{3-[4-(6-Fluoro-benzo[d]isoxazol-3-yl)-piperidin-1-yl]-propyl}-tetrahydro-pyrrolo[1,2-c]pyrimidine-1,3-dione;

2-{3-[4-(5-Fluoro-1H-indol-3-yl)-piperidin-1-yl]-propyl}-tetrahydro-pyrrolo[1,2-c]pyrimidine-1,3-dione;

2-[2-(4-Benzo[d]isothiazol-3-yl-piperazin-1-ylmethyl)-cyclohexylmethyl]-tetrahydro-pyrrolo[1,2-c]pyrimidine-1,3-dione;

2-[2-(4-Benzo[d]isothiazol-3-yl-piperazin-1-ylmethyl)-cyclohexylmethyl]-tetrahydro-pyrrolo[1,2-c]pyrimidine-1,3-dione oxalate;

2-{2-[4-(6-Fluoro-benzo[d]isoxazol-3-yl)-piperidin-1-ylmethyl]-cyclohexylmethyl}-tetrahydro-pyrrolo[1,2-c]pyrimidine-1,3-dione;

2-{2-[4-(6-Fluoro-benzo[d]isoxazol-3-yl)-piperidin-1-ylmethyl]-cyclohexylmethyl}-tetrahydro-pyrrolo[1,2-c]pyrimidine-1,3-dione oxalate;

7-[2-(4-Benzo[d]isothiazol-3-yl-piperazin-1-ylmethyl)-cyclohexylmethyl]-tetrahydro-pyrimido[6,1-c][1,4]oxazine-6,8-dione;
7-[4-(4-Benzo[d]isothiazol-3-yl-piperazin-1-yl)-butyl]-hexahydro-pyrazino[1,2-c]pyrimidine-6,8-dione;
7-{4-[4-(6-Fluoro-benzo[d]isoxazol-3-yl)-piperidin-1-yl]-butyl}-hexahydro-pyrazino[1,2-c]pyrimidine-6,8-dione;
7-[4-(4-Benzo[d]isothiazol-3-yl-piperazin-1-yl)-butyl]-6,8-dioxo-octahydro-pyrazino[1,2-c]pyrimidine-2-carboxylic acid methyl ester;
7-[4-(4-Benzo[d]isothiazol-3-yl-piperazin-1-yl)-butyl]-6,8-dioxo-octahydro-pyrazino[1,2-c]pyrimidine-2-carboxylic acid methyl ester fumarate;
7-{4-[4-(6-Fluoro-benzo[d]isoxazol-3-yl)-piperidin-1-yl]-butyl}-6,8-dioxo-octahydro-pyrazino[1,2-c]pyrimidine-2-carboxylic acid methyl ester;
7-{4-[4-(6-Fluoro-benzo[d]isoxazol-3-yl)-piperidin-1-yl]-butyl}-6,8-dioxo-octahydro-pyrazino[1,2-c]pyrimidine-2-carboxylic acid methyl ester fumarate;
2-Acetyl-7-[4-(4-benzo[d]isothiazol-3-yl-piperazin-1-yl)-butyl]-hexahydro-pyrazino[1,2-c]pyrimidine-6,8-dione;
2-Acetyl-7-[4-(4-benzo[d]isothiazol-3-yl-piperazin-1-yl)-butyl]-hexahydro-pyrazino[1,2-c]pyrimidine-6,8-dione fumarate;
7-[4-(4-Benzo[d]isothiazol-3-yl-piperazin-1-yl)-butyl]-2-isopropyl-hexahydro-pyrazino[1,2-c]pyrimidine-6,8-dione;
7-[4-(4-Benzo[d]isothiazol-3-yl-piperazin-1-yl)-butyl]-2-isopropyl-hexahydro-pyrazino[1,2-c]pyrimidine-6,8-dione fumarate;
2-{4-[4-(Benzo[d]isoxazol-3-yl)-piperidin-1-yl]-butyl}-tetrahydro-pyrrolo[1,2-c]pyrimidine-1,3-dione;
2-{4-[4-(Benzo[d]isoxazol-3-yl)-piperidin-1-yl]-butyl}-tetrahydro-pyrrolo[1,2-c]pyrimidine-1,3-dione oxalate;
2-[3-(4-Benzo[d]isoxazol-3-yl-piperidin-1-yl)-propyl]-tetrahydro-pyrrolo[1,2-c]pyrimidine-1,3-dione; and
2-[3-(4-Benzo[d]isoxazol-3-yl-piperidin-1-yl)-propyl]-tetrahydro-pyrrolo[1,2-c]pyrimidine-1,3-dione oxalate; or an isotopic form, a stereoisomer, or a pharmaceutically acceptable salt thereof.

In another aspect, the present invention relates to a method of treating or preventing central nervous system disorder or condition selected from anxiety disorders, agitation, aggression, borderline personality disorder, schizophrenia, emotional disturbance, psychotic disorders, mood disorders, bipolar I type disorder, bipolar II type disorder, delirium, hysteria, dissociative disorder, sleep disorder, anhedonia, neuropsychiatric symptoms associated with dementia, amnestic disorders, cognitive disorders, cognitive deficits associated with schizophrenia, movement disorders, depressive disorders, drug dependencies, drug addictions, autism disorder, Tourette syndrome and/or attention-deficit/hyperactivity disorder comprising administering to a patient in need thereof a therapeutically effective amount of the compound of formula (I) or an isotopic form, a stereoisomer, or a pharmaceutically acceptable salt thereof.

In another aspect, the present invention relates to the compound of formula (I) or an isotopic form, a stereoisomer, or a pharmaceutically acceptable salt thereof for use in the treatment of central nervous system disorder or condition selected from anxiety disorders, agitation, aggression, borderline personality disorder, schizophrenia, emotional disturbance, psychotic disorders, mood disorders, bipolar I type disorder, bipolar II type disorder, delirium, hysteria, dissociative disorder, sleep disorder, anhedonia, neuropsychiatric symptoms associated with dementia, amnestic disorders, cognitive disorders, cognitive deficits associated with schizophrenia, movement disorders, depressive disorders, drug dependencies, drug addictions, autism disorder, Tourette syndrome and/or attention-deficit/hyperactivity disorder.

In another aspect, the present invention relates to the use of the compound of formula (I) or an isotopic form, a stereoisomer, or a pharmaceutically acceptable salt thereof for the manufacture of a medicament for the treatment of central nervous system disorder or condition selected from anxiety disorders, agitation, aggression, borderline personality disorder, schizophrenia, emotional disturbance, psychotic disorders, mood disorders, bipolar I type disorder, bipolar II type disorder, delirium, hysteria, dissociative disorder, sleep disorder, anhedonia, neuropsychiatric symptoms associated with dementia, amnestic disorders, cognitive disorders, cognitive deficits associated with schizophrenia, movement disorders, depressive disorders, drug dependencies, drug addictions, autism disorder, Tourette syndrome and/or attention-deficit/hyperactivity disorder.

In another aspect, the present invention relates to the pharmaceutical composition comprising a therapeutically effective amount of the compound of formula (I) or an isotopic form, a stereoisomer, or a pharmaceutically acceptable salt thereof for use in the treatment of central nervous system disorder or condition selected from anxiety disorders, agitation, aggression, borderline personality disorder, schizophrenia, emotional disturbance, psychotic disorders, mood disorders, bipolar I type disorder, bipolar II type disorder, delirium, hysteria, dissociative disorder, sleep disorder, anhedonia, neuropsychiatric symptoms associated with dementia, amnestic disorders, cognitive disorders, cognitive deficits associated with schizophrenia, movement disorders, depressive disorders, drug dependencies, drug addictions, autism disorder, Tourette syndrome and/or attention-deficit/hyperactivity disorder.

In some embodiments, the anxiety disorder is selected from panic disorder with or without agoraphobia, agoraphobia without history of panic disorder; specific phobias for example specific animal phobias, social anxiety, and social phobia; obsessive-compulsive disorder; stress disorders including post-traumatic stress disorder, and acute stress disorder; and generalized anxiety disorders.

In some embodiments, anhedonia is selected from iatrogenic anhedonia; anhedonia of a psychic or mental cause; anhedonia associated with depression; anhedonia associated with schizophrenia.

In some embodiments, the neuropsychiatric symptoms associated with dementia are selected from apathy/indifference, agitation, aggression, depression, anxiety, irritability/lability, dysphoria, aberrant motor behavior, delusions, hallucinations, elation/euphoria, psychosis, disinhibition, sleep and night time behavior disorders, appetite and eating disorders or combination thereof.

In some embodiments, schizophrenia is refractory schizophrenia, intractable schizophrenia or chronic schizophrenia.

In some embodiments, the psychotic disorder is selected from schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, or psychotic mood disorders such as severe major depressive disorder.

In some embodiments, the mood disorder is selected from mood disorders associated with psychotic disorders, such as acute mania and depression associated with bipolar disorder; or mood disorder associated with schizophrenia.

In some embodiments, the cognitive disorder is selected from senile dementia, dementia of the Alzheimer's type, memory disorders, loss of executive function, vascular dementia, dementia due to HIV disease, dementia due to head trauma, dementia due to Parkinson's disease, dementia due to Huntington's disease, dementia due to Pick's disease, dementia due to Creutzfeldt-Jakob disease, or dementia due to multiple etiologies.

epines, nicotine, phenobarbital, stimulant intoxication, narcotism, and behavioral addictions, such as an addiction to gambling.

In another embodiment, the present invention relates to the process for the preparation of the compound of formula (I) as described herein.

Experimental Procedure:

The scheme depicts a general process for the preparation of the compound of formula (I), wherein X is halogen; HetAr, A, B, P, Q, n, and m are as defined above.

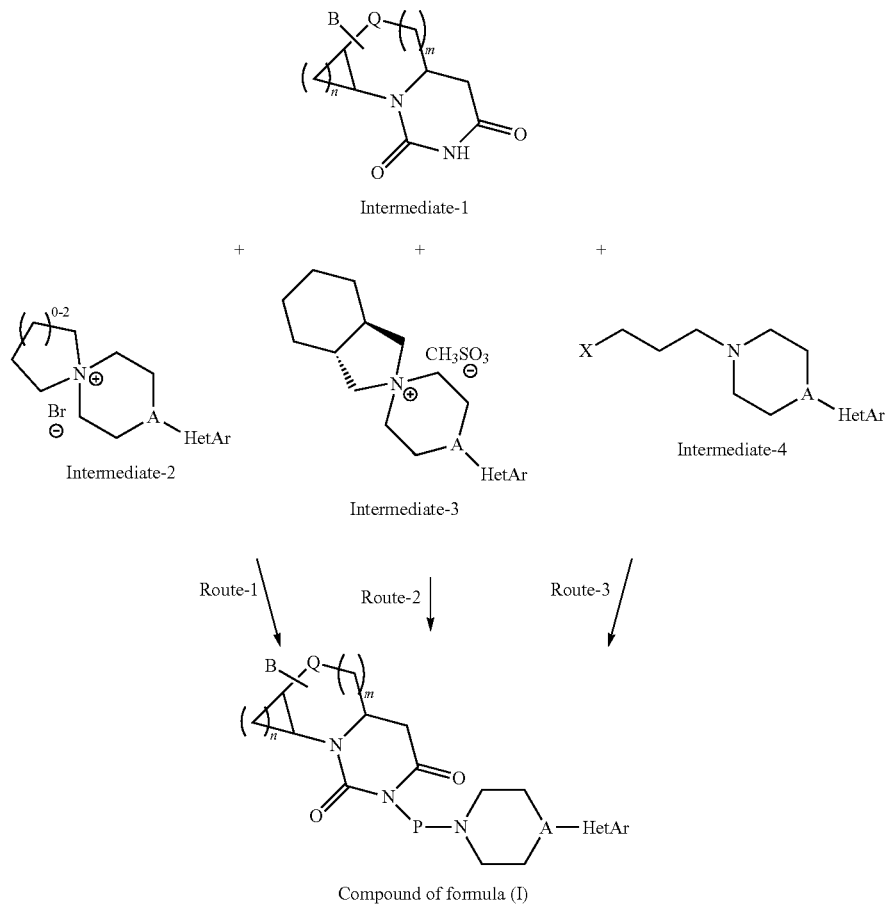

In some embodiments, the movement disorder is selected from akinesia, dyskinesia, including familial paroxysmal dyskinesia, spasticity, Tourette syndrome, Scott syndrome, PALSY syndrome, akinetic-rigid syndrome, extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia, or medication-induced postural tremor.

In some embodiments, the depressive disorder is selected from, major depression, single episodic major depressive disorder, recurrent major depressive disorders, depressive neurosis and neurotic depression, or melancholic depression.

In some embodiments, the drug dependencies and drug addictions is selected from dependencies on, or addiction to, alcohol, alcohol intoxication, heroin, cocaine, benzodiaz- Route-1: Preparation of Compound of Formula (I)

A mixture of intermediate-1, intermediate-2, and an inorganic base selected from $K_2CO_3$, $KHCO_3$, $Na_2CO_3$, $NaHCO_3$ or NaOH, in solvent selected from 1,4-dioxane, toluene, DMF, or xylene in presence of metal scavenger such as 18-crown-6 was stirred and heated at 100-155° C. preferably at 133-140° C. until most of intermediate-1 gets consumed or for a period of 3-12 h preferably for a period of 6 h. The desired product would be isolated by standard isolation techniques such as filtration, trituration, water/organic work-up or re-crystallization method to obtain the compound of formula (I).

Route-2: Preparation of Compound of Formula (I)

A mixture of intermediate-1, intermediate-3, and an inorganic base selected from $K_2CO_3$, $KHCO_3$, $Na_2CO_3$, $NaHCO_3$ or NaOH, in solvent selected from 1,4-dioxane, toluene, DMF, or xylene in presence of metal scavenger such as 18-crown-6 was stirred and heated at 100-155° C. preferably at 133-140° C. until most of intermediate-1 gets consumed or for a period of 3-12 h preferably for a period of 6 h. The desired product would be isolated by standard isolation techniques such as filtration, trituration, water/organic work-up or re-crystallization method to obtain the compound of formula (I).

Route-3: Preparation of Compound of Formula (I)

The suspension of intermediate-1, intermediate-4 and an inorganic base selected from $K_2CO_3$, $KHCO_3$, $Na_2CO_3$, $NaHCO_3$ or NaOH, in solvent selected from 1,4-dioxane, toluene, DMF, or xylene and most preferably DMF was stirred and heated at 100-155° C. preferably at 150-155° C. until most of intermediate-1 gets consumed or for a period of 12-16 h preferably for a period of 16 h. The desired product would be isolated by standard isolation techniques such as filtration, trituration, water/organic work-up or re-crystallization method to obtain the compound of formula (I).

Preparation of Pharmaceutically Acceptable Salt of the Compound of Formula (I)

The compound of formula (I) can optionally be converted into its pharmaceutically acceptable salt by reaction with the appropriate acid or acid derivative. Suitable pharmaceutically acceptable salts will be apparent to those skilled in the art. The salts are formed with inorganic acids e.g., hydrochloric, hydrobromic, sulfuric, nitric or phosphoric acid, or organic acids e.g., oxalic, succinic, maleic, acetic, fumaric, citric, malic, tartaric, benzoic, p-toluic, p-toluenesulfonic, benzenesulfonic acid, methanesulfonic or naphthalene sulfonic acid.

Preparation of Stereoisomers of the Compound of Formula (I)

The stereoisomers of the compounds of formula (I) may be prepared in one or more conventional ways presented below:

a. One or more of the reagents may be used in their optically active form.
b. Optically pure catalyst or chiral ligands along with metal catalyst may be employed in the reduction process. The metal catalyst may be rhodium, ruthenium, indium, and the like. The chiral ligands may preferably be chiral phosphines.
c. The mixture of stereoisomers may be resolved by conventional methods such as forming diastereomeric salts with chiral acids or chiral amines or chiral amino alcohols, or chiral amino acids. The resulting mixture of diastereomers may then be separated by methods such as fractional crystallization, chromatography, and the like, which is followed by an additional step of isolating the optically active product from the resolved material salt.
d. The mixture of stereoisomers may be resolved by conventional methods such as microbial resolution, resolving the diastereomeric salts formed with chiral acids or chiral bases. Chiral acids that can be employed may be tartaric acid, mandelic acid, lactic acid, camphorsulfonic acid, amino acids, and the like. Chiral bases that can be employed may be cinchona alkaloids, brucine or a basic amino acid such as lysine, arginine, and the like.

In another embodiment, the suitable pharmaceutically acceptable salts of the compound of formula (I) include but are not limited to, hydrochloride, hydrobromide, oxalate, fumarate, tartrate, maleate, and succinate.

In another embodiment, the present invention relates to the pharmaceutical compositions comprising the compound of formula (I) or a pharmaceutically acceptable salt thereof, and pharmaceutically acceptable excipients. To use the compounds of formula (I) or their stereoisomers and a pharmaceutically acceptable salt thereof in therapy, they will normally be formulated into a pharmaceutical composition in accordance with standard pharmaceutical practice.

The pharmaceutical compositions of the present invention may be formulated in a conventional manner using one or more pharmaceutically acceptable excipients. The pharmaceutically acceptable excipients are diluents, disintegrating agents, binders, lubricants, glidants, polymers, coating agents, solvents, co-solvents, preservatives, wetting agents, thickening agents, antifoaming agents, sweetening agents, flavoring agents, antioxidants, colorants, solubilizers, plasticizer, dispersing agents and the like. Excipients are selected from microcrystalline cellulose, mannitol, lactose, pregelatinized starch, sodium starch glycolate, corn starch or derivatives thereof, povidone, crospovidone, calcium stearate, glyceryl monostearate, glyceryl palmitostearate, talc, colloidal silicon dioxide, magnesium stearate, sodium lauryl sulfate, sodium stearyl fumarate, zinc stearate, stearic acid, hydrogenated vegetable oil, gum *arabica*, magnesia, glucose, fats, waxes, natural or hardened oils, water, physiological sodium chloride solution, alcohols, for example, ethanol, propanol or glycerol, sugar solutions, such as glucose solutions or mannitol solutions and the like or a mixture of the various excipients.

In yet another embodiment, the compounds of the invention may be formulated in the form of pills, tablets, coated tablets, capsules, powder, granules, pellets, patches, implants, films, liquids, semi-solids, gels, aerosols, emulsions, elixirs and the like. Such pharmaceutical compositions and processes for preparing the same are well known in the art.

In yet another embodiment, the pharmaceutical composition of the present invention contains 1 to 90%, 5 to 75%, or 10 to 60% by weight of the compounds of the present invention or pharmaceutically acceptable salt thereof. The amount of the compounds or its pharmaceutically acceptable salt in the pharmaceutical composition(s) can range from about 1 mg to about 500 mg, from about 5 mg to about 400 mg, from about 5 mg to about 250 mg, from about 7 mg to about 150 mg, or in any range falling within the broader range of 1 mg to 500 mg.

The dose of the active compounds can vary depending on factors such as age and weight of patient, nature and severity of the disease or disorder to be treated and such other factors. Therefore, any reference regarding therapeutically effective amount of the compounds of general formula (I), stereoisomers and pharmaceutically acceptable salts thereof refer to the aforementioned factors.

The following abbreviations are used herein:
5-$HT_{1A}$: 5-Hydroxytryptamine 1A receptor
5-$HT_{2A}$: 5-Hydroxytryptamine 2A receptor
AUC: Area under the curve
Boc: tert-Butyloxycarbonyl
Bn: Benzyl
$C_{max}$: Maximum concentration
Cbz: Benzyloxycarbonyl
$CDCl_3$: Deuteratedchloroform
DCM: Dichloromethane
DIPEA: N,N-Diisopropylethylamine
DMF: N,N-Dimethylformamide
DMAP: 4-Dimethylaminopyridine
DMSO: Dimethyl sulfoxide
DOI: 2,5-Dimethoxy-4-iodoamphetamine
$EC_{50}$: Half maximal effective concentration
EtOAc: Ethyl acetate
EtOH: Ethanol h: Hour(s)
g: Gram(s)
HCl: Hydrochloric acid
H₂O: Water
K₂CO₃: Potassium carbonate
KHCO₃: Potassium bicarbonate
KOH: Potassium hydroxide
L: Liter
LC-MS/MS: Liquid chromatography-Mass spectrometry/Mass spectrometry
LiOH: Lithium hydroxide
nM: Nanomolar
mL: Milliliter
mmol: Millimoles
min: Minutes
M: Molar
Mp: Melting point
MgSO₄: Magnesium sulfate
NaHCO₃: Sodium bicarbonate
Na₂CO₃: Sodium carbonate
NaOH: Sodium hydroxide
Na₂SO₄: Sodium sulfate
NH₄Cl: Ammonium chloride
rpm: Revolutions per minute
r.t: Room temperature (25° C. to 30° C.)
ROA: Route of Administration
THF: Tetrahydrofuran
$t_{1/2}$: Half-life time
μL: Microliter
μM: Micromolar
ng/ml: Nanograms per milliliter
i.m: Intramuscular
p.o: Per oral
s.c: Subcutaneous

EXAMPLES

The compounds of the present invention were prepared according to the following experimental procedures, using appropriate materials and conditions. The following examples are provided by way of illustration only but not to limit the scope of the present invention.

Preparation of Intermediates

Intermediate-1a: Preparation of(S)-tetrahydro-pyrrolo[1,2-c]pyrimidine-1,3-dione

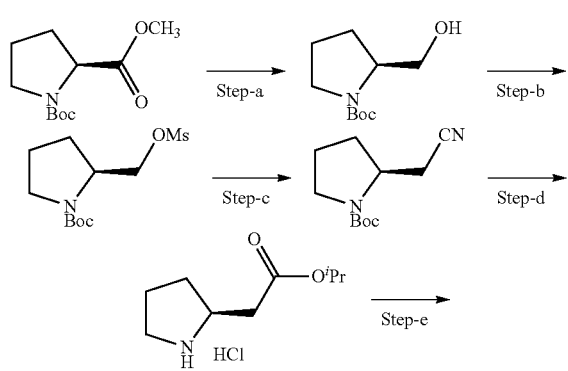

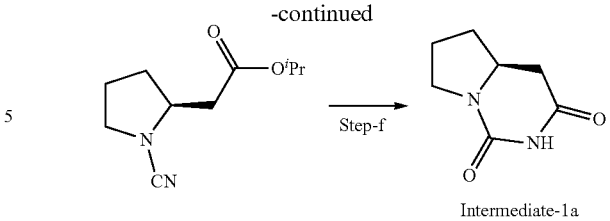

Intermediate-1a

Step-a: At about 0° C., 1M THF solution of lithium aluminum hydride (791.6 mL) was added drop-wise to a mixture of pyrrolidine-1,2-dicarboxylic acid 1-tert-butyl ester 2-methyl ester (165.0 g, 719.6 mmol). After stirring for about 60 min at about 0° C., the mixture was quenched by adding EtOAc (360.0 mL), saturated aqueous NH₄Cl solution (719.6 mL) followed by IN NaOH solution (719.6 mL). The suspension was stirred for 1 h before being filtered over cloth/paper. The filtrate was then separated into two layers, the organic layer was washed with brine solution, dried over anhydrous Na₂SO₄ and the solvent was removed under vacuum to obtain (S)-2-hydroxymethyl-pyrrolidine-1-carboxylic acid tert-butyl ester (126.0 g) in 87% yield. ¹H NMR (400 MHZ, CDCl₃): δ 4.80-4.72 (m, 1H), 4.01-3.92 (m, 1H), 3.68-3.54 (m, 2H), 3.50-3.40 (m, 1H), 3.37-3.28 (m, 1H), 2.08-1.50 (m, 1H), 1.90-1.75 (m, 3H), 1.47 (s, 9H): IR (film) ν 3428, 2971, 2880, 2376, 1683, 1407 cm⁻¹: Mass (m/z): 202.1 (M+H)⁺. Step-b: To a stirred mixture of step-a compound (200.0 g, 993.7 mmol), cooled at 0° C., triethylamine (278.9 mL, 1987.4 mmol) followed by methanesulfonyl chloride (97.5 mL, 1192.4 mmol) was added. The reaction mass was stirred for a period of 1 h followed by quenching with water. The two layers were separated and the organic layer was washed again with water, dried over anhydrous Na₂SO₄ and the solvent was removed under vacuum to obtain (S)-2-(methane sulfonyloxymethyl)-pyrrolidine-1-carboxylic acid tert-butyl ester (274.0 g) in 98% yield.

¹H NMR (400 MHZ, CDCl₃): δ 4.35-4.28 (m, 2H), 4.05-3.95 (m, 1H), 3.40-3.30 (m, 2H), 3.00 (s, 3H), 2.10-1.80 (m, 4H), 1.46 (s, 9H): Mass (m/z): 280.0 (M+H)⁺.

Step-c: A solution of step-b compound (229.8 g, 822.6 mmol) and potassium cyanide (160.4 g, 2467.8 mmol) in DMSO (1.64 L) was stirred at about 90° C. for about 7 h. Following standard extractive workup with EtOAc followed by solvent evaporation yielded (S)-2-Cyanomethyl-pyrrolidine-1-carboxylic acid tert-butyl ester as oil (137.1 g) in 79% yield.

¹H NMR (400 MHZ, CDCl₃): δ 4.05-3.96 (m, 1H), 3.50-3.35 (m, 2H), 2.88-2.80 (m, 0.5H), 2.78-2.65 (m, 2H), 2.60-2.52 (m, 0.5H), 2.22-2.12 (m, 1H), 2.08-1.80 (m, 3H), 1.46 (s, 9H). IR (film) ν 2975, 2885, 2248, 1693, 1462, 1397, 1254 cm 1; Mass (m/z): 211.2 (M+H)⁺.

Step-d: A solution of step-c compound (0.50 g, 2.37 mmol) in isopropanol (4.8 mL) cooled at 0-5° C., a solution of dry HCl in isopropanol (3 M, 23.7 mL) was added over a period of 15 min. The reaction mass was stirred at the same temperature for an additional 1 h before raising the temperature gradually to reflux. The reflux was continued for 48 h followed by distillation of solvent and removal of solvent traces under high vacuum at 50° C. to obtain (S)-2-Pyrrolidin-2-yl-acetic acid isopropyl ester hydrochloride (0.42 g) as off-white colored solid in 86% yield.

¹H-NMR (DMSO-d₆): δ 9.55 (bs, 1H), 9.38 (bs, 1H), 5.0-4.88 (m, 1H), 3.76-3.63 (m, 1H), 3.20-3.10 (m, 2H), 2.90 (dd, J=7.6, 17.2 Hz, 1H), 2.15-2.05 (m, 1H), 2.0-1.77 (m, 2H), 1.62-1.51 (m, 1H), 1.22 (d, J=6.0 Hz, 6H): Mass (m/z): 172.0 (M+H)⁺.

Step-e: A solution of step-d compound (100.3 g, 482.9 mmol) in a 1:1 mixture of THF and water (1932.0 mL) cooled at 0-5° C., NaHCO$_3$ (386.3 g, 4829 mmol) was added. The reaction mixture was stirred for additional 30 min and the cyanogen bromide (61.4 g, 579.4 mmol) was added over a period of 15 min. The reaction mass was stirred at the same temperature for an additional 2 h before being extracted multiple times with EtOAc. Combined organic layer was washed with brine solution, dried over anhydrous Na$_2$SO$_4$ and the solvent was evaporated under vacuum to obtain (S)-(1-Cyanopyrrolidin-2-yl)-acetic acid isopropyl ester (66.9 g) in 70.6% yield.

$^1$H-NMR (CDCl$_3$): δ 5.10-5.0 (m, 1H), 4.02-3.94 (m, 1H), 3.01-2.88 (m, 2H), 2.78 (dd, J=5.2, 16.0 Hz, 1H), 2.43 (dd, J=8.4, 16.0 Hz, 1H), 2.22-2.12 (m, 1H), 2.0-1.88 (m, 2H), 1.71-1.62 (m, 1H), 1.26 (d, J=6.0 Hz, 6H): Mass (m/z): 197.1 (M+H)$^+$.

Step-f: A solution of step-e compound (66.9 g, 340.9 mmol) in dibutyl phosphate (143.3 mL, 681.8 mmol) at r.t. was heated at 110° C. for 2 h. The reaction mass was then cooled to r.t. and triturated multiple times with hexane followed couple of times. The precipitated solid compound was then filtered at Nutsche filter to obtain (S)-Tetrahydro-pyrrolo[1,2-c]pyrimidine-1,3-dione (45.1 g) in 85% yield.
$^1$H-NMR (CDCl$_3$): δ 7.95 (bs, 1H), 3.82-3.72 (m, 1H), 3.70-3.60 (m, 1H), 3.56-3.47 (m, 1H), 2.80 (dd, J=4.0, 16.4 Hz, 1H), 2.38 (dd, J=13.2, 16.4 Hz, 1H), 2.33-2.26 (m, 1H), 2.14-2.05 (m, 1H), 1.98-1.85 (m, 1H), 1.69-1.57 (m, 1H): Mass (m/z): 154.9 (M+H)$^+$.

Intermediate-1b: Preparation of 6-fluoro-tetrahydro-pyrrolo[1,2-c]pyrimidine-1,3-dione

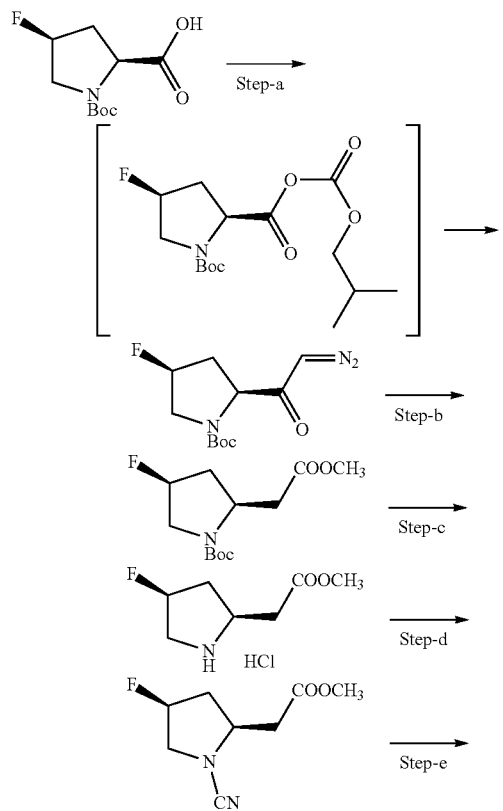

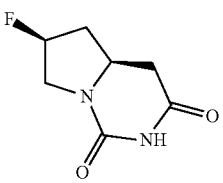

Intermediate-1b

Step-a: A stirred solution of 4-fluoro-pyrrolidine-1,2-dicarboxylic acid 1-tert-butyl ester (0.70 g, 3.0 mmol: prepared from 4-hydroxy-pyrrolidine-2-carboxylic acid by using protocol as reported in WO2007113634 A1) in DCM (6.0 mL), cooled at −30° C., triethylamine (0.5 mL, 3.6 mmol) and isobutyl chloroformate (0.47 mL, 3.6 mmol) were added. The reaction mass was stirred for additional 15 min. The reaction mass was warmed to 0° C., then a freshly prepared diethylether solution of diazomethane (~15-30 mmol) was added. The reaction mixture was stirred for additional 30 min at the same temperature. The excess diazomethane was quenched by adding methanol. The reaction mixture was diluted with additional diethyl ether and washed with aqueous saturated solution of NaHCO$_3$. The organic layer was washed with brine solution, dried over anhydrous Na$_2$SO$_4$ and the solvent was removed under vacuum to obtain 2-(2-diazoacetyl)-4-fluoropyrrolidine-1-carboxylic acid tert-butyl ester (1.1 g) in 42% yield. Mass (m/z): 258.2 (M+H)$^+$.

Step-b: To the stirred solution of step-a compound (1.1 g, 4.27 mmol) in methanol (17.0 mL) under nitrogen atmosphere cooled at −30° C., DIPEA (2.24 mL, 12.82 mmol) was added. After 10 min, silver benzoate (0.21 g, 0.85 mmol) was added and the reaction mass was gradually warmed to r.t. After 2 h, the reaction mass was filtered through cloth/paper bed and filtrate was concentrated under vacuum to obtain a crude mass which purified by silica gel column chromatography to obtain 4-fluoro-2-methoxycarbonylmethyl-pyrrolidine-1-carboxylic acid tert-butyl ester (0.186 g) in 17% yield. $^1$H-NMR (CDCl$_3$): δ 5.30-5.10 (m, 1H), 4.56-4.40 (m, 1H), 3.67 (s, 3H), 3.60-3.48 (m, 1H), 3.45-3.25 (m, 1H), 2.90-2.77 (m, 2H), 2.60-2.40 (m, 1H), 2.05-1.90 (m, 1H), 1.48 (s, 9H): Mass (m/z): 262.2 (M+H)$^+$.

Step-c: To the stirred solution of step-b compound (0.186 g, 0.72 mmol) in methanol (1.5 mL), cooled at 0° C., a dry HCl in methanol (3 M, 1.5 mL) was added. The reaction mass was gradually warmed to r.t. and stirred for 16 h. The contents were removed under vacuum to obtain a gummy mass which was triturated with diethyl ether to obtain (4-Fluoro-pyrrolidin-2-yl)-acetic acid methyl ester hydrochloride as solid (0.097 g) in 69% yield. $^1$H-NMR (DMSO-d$_6$): δ 9.66 (bs, 1H), 9.29 (bs, 1H), 5.50-5.30 (m, 1H), 4.02-3.90 (m, 1H), 3.66 (s, 3H), 3.60-3.45 (m, 1H), 3.45-3.30 (m, 1H), 2.90-2.75 (m, 2H), 2.60-2.45 (m, 1H), 2.05-1.88 (m, 1H): Mass (m/z): 162.1 (M+H)$^+$.

Step-d: By following the procedure as reported for step-e of intermediate-1a preparation, step-c compound (97.0 mg) was converted to (1-cyano-4-fluoro-pyrrolidin-2-yl)-acetic acid methyl ester (73.0 mg) in 80% yield. $^1$H-NMR (CDCl$_3$): δ 5.40-5.20 (m, 1H), 4.02-3.90 (m, 1H), 3.66 (s, 3H), 3.60-3.45 (m, 1H), 3.45-3.30 (m, 1H), 2.90-2.75 (m, 2H), 2.60-2.45 (m, 1H), 2.05-1.88 (m, 1H); Mass (m/z): 187.1 (M+H)$^+$.

Step-e: By following the procedure as reported for step-f of intermediate-1a preparation, step-d compound (73.0 mg) was converted to 6-fluoro-tetrahydro-pyrrolo[1,2-c]pyrimidine-1,3-dione (37.0 mg) in 55% yield. $^1$H-NMR (CDCl$_3$): δ 7.43 (bs, 1H), 5.36-5.18 (m, 1H), 4.17 (dd, J=13.2, 19.6 Hz, 1H), 4.05-3.95 (m, 1H), 3.57 (dd, J=3.6, 13.6 Hz, 1H), 2.77 (dd, J=4.0, 16.4 Hz, 1H), 2.65 (dd, J=13.2, 16.4 Hz, 1H), 2.24-2.0 (m, 2H); Mass (m/z): 173.1 (M+H)$^+$.

Intermediate-1c: Preparation of Hexahydro-1b,3-diaza-cyclopropa[a]indene-2,4-dione

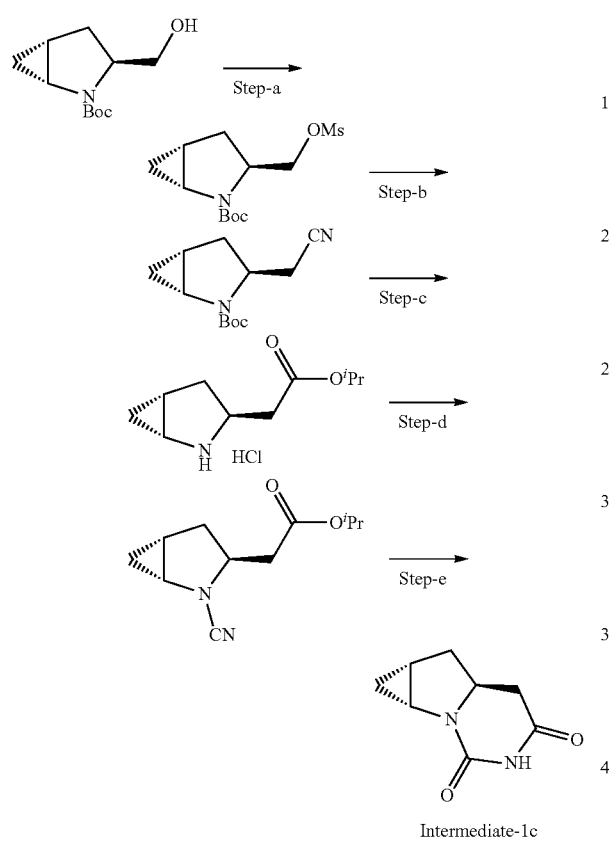

Intermediate-1c

Step-a: 3-(Methanesulfonyloxymethyl)-2-aza-bicyclo[3.1.0]hexane-2-carboxylic acid tert-butyl ester was prepared from 3-hydroxymethyl-2-aza-bicyclo[3.1.0]hexane-2-carboxylic acid tert-butyl ester (prepared by following the protocol from WO2011061751) by following the procedure as reported for step-b of intermediate-1a preparation. Mass (m/z): 292.1 (M+H)$^+$.

Step-b: 3-Cyanomethyl-2-aza-bicyclo[3.1.0]hexane-2-carboxylic acid tert-butyl ester was prepared from step-a compound by following the procedure as reported for step-c of intermediate-1a preparation. Mass (m/z): 223.1 (M+H)$^+$.

Step-c: (2-Aza-bicyclo[3.1.0]hex-3-yl)-acetic acid isopropyl ester hydrochloride was prepared from step-b compound by following the procedure as reported for step-d of intermediate-1a preparation. Mass (m/z): 184.1 (M+H)$^+$.

Step-d: (2-Cyano-2-aza-bicyclo[3.1.0]hex-3-yl)-acetic acid isopropyl ester was prepared from step-c compound by following the procedure as reported for step-e of intermediate-1a preparation. Mass (m/z): 209.2 (M+H)$^+$.

Step-e: Hexahydro-1b,3-diaza-cyclopropa[a]indene-2,4-dione was prepared from step-d compound by following the procedure as reported for step-f of intermediate-1a preparation. Mass (m/z): 167.1 (M+H)$^+$.

Intermediate-1d: Preparation of hexahydro-pyrido[1,2-c]pyrimidine-1,3-dione

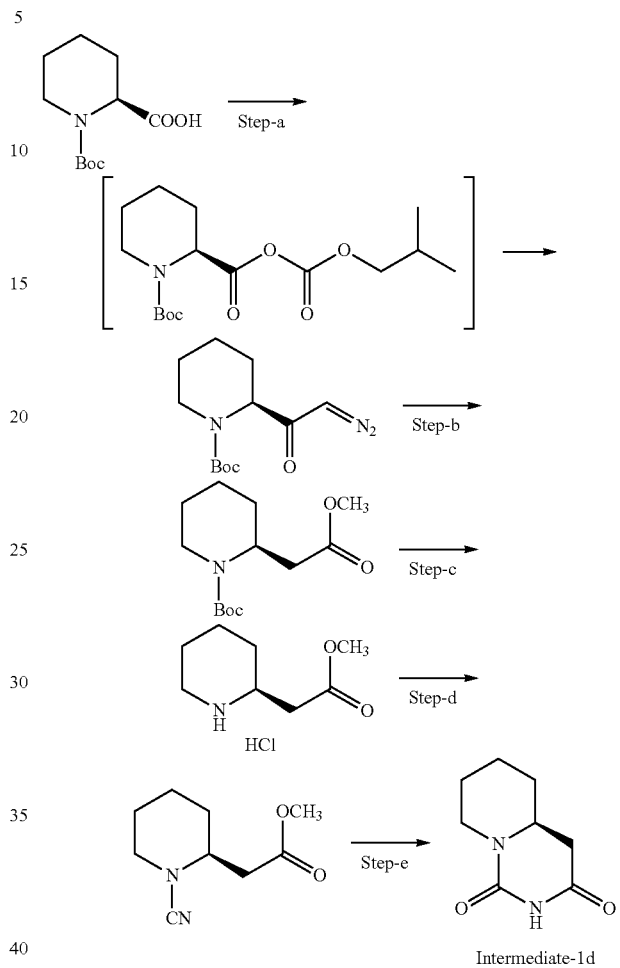

Intermediate-1d

Step-a: 2-(2-Diazo-acetyl)-piperidine-1-carboxylic acid tert-butyl ester was prepared from commercially available piperidine-1,2-dicarboxylic acid 1-tert-butyl ester by following the procedure as reported for step-a of intermediate-1b preparation. $^1$H NMR (400 MHZ, CDCl$_3$): δ 5.42 (s, 1H), 4.85-4.75 (m, 1H), 4.20-3.92 (m, 1H), 2.95-2.72 (m, 1H), 2.35-2.22 (m, 1H), 1.70-1.60 (m, 4H), 1.55-1.50 (m, 1H), 1.48 (s, 9H); Mass (m/z): 254.2 (M+H)$^+$.

Step-b: 2-Methoxycarbonylmethyl-piperidine-1-carboxylic acid tert-butyl ester was prepared from step-a compound by following the procedure as reported for step-b of intermediate-1b preparation. $^1$H NMR (400 MHZ, CDCl$_3$): δ 4.76-4.62 (m, 1H), 4.10-3.90 (m, 1H), 3.66 (s, 3H), 2.85-2.70 (m, 1H), 2.65-2.49 (m, 2H), 1.75-1.60 (m, 4H), 1.55-1.35 (m, 11H); Mass (m/z): 258.2 (M+H)$^+$.

Step-c: Piperidin-2-yl-acetic acid methyl ester hydrochloride was prepared from step-b compound by following the procedure as reported for step-c of intermediate-1b preparation. $^1$H NMR (400 MHZ, DMSO-d$_6$): δ 9.09 (bs, 2H), 3.64 (s, 3H), 3.43-3.30 (m, 1H), 3.27-3.19 (m, 1H), 2.95-2.80 (m, 2H), 2.68 (dd, J=8.0, 16.4 Hz, 1H), 1.87-1.78 (m, 1H), 1.75-1.67 (m, 2H), 1.65-1.58 (m, 1H), 1.52-1.42 (m, 2H); Mass (m/z): 157.9 (M+H)$^+$.

Step-d: (1-Cyano-piperidin-2-yl)-acetic acid methyl ester was prepared from step-c compound by following the procedure as reported for step-d of intermediate-1b preparation.
$^1$H NMR (400 MHZ, CDCl$_3$): δ 3.72 (s, 3H), 3.48-3.38 (m, 2H), 3.15-3.04 (m, 1H), 2.86 (dd, J=6.4, 16.0 Hz, 1H), 2.55 (dd, J=7.2, 16.0 Hz, 1H), 1.88-1.75 (m, 2H), 1.70-1.62 (m, 2H), 1.56-1.36 (m, 2H); Mass (m/z): 183.1 (M+H)$^+$.

Step-e: Hexahydro-pyrido[1,2-c]pyrimidine-1,3-dione was prepared from step-d compound by following the procedure as reported for step-e of intermediate-1b preparation. $^1$H NMR (400 MHZ, DMSO-d$_6$): δ 10.18 (bs, 1H), 4.12-4.05 (m, 1H), 3.43-3.30 (m, 1H), 2.70-2.58 (m, 2H), 2.41 (dd, J=8.8, 16.8 Hz, 1H), 1.78-1.68 (m, 2H), 1.68-1.62 (m, 1H), 1.45-1.25 (m, 2H), 1.25-1.13 (m, 1H); Mass (m/z): 169.0 (M+H)$^+$.

Intermediate-1e: Preparation of tetrahydro-pyrimido[6,1-c][1,4]oxazine-6,8-dione

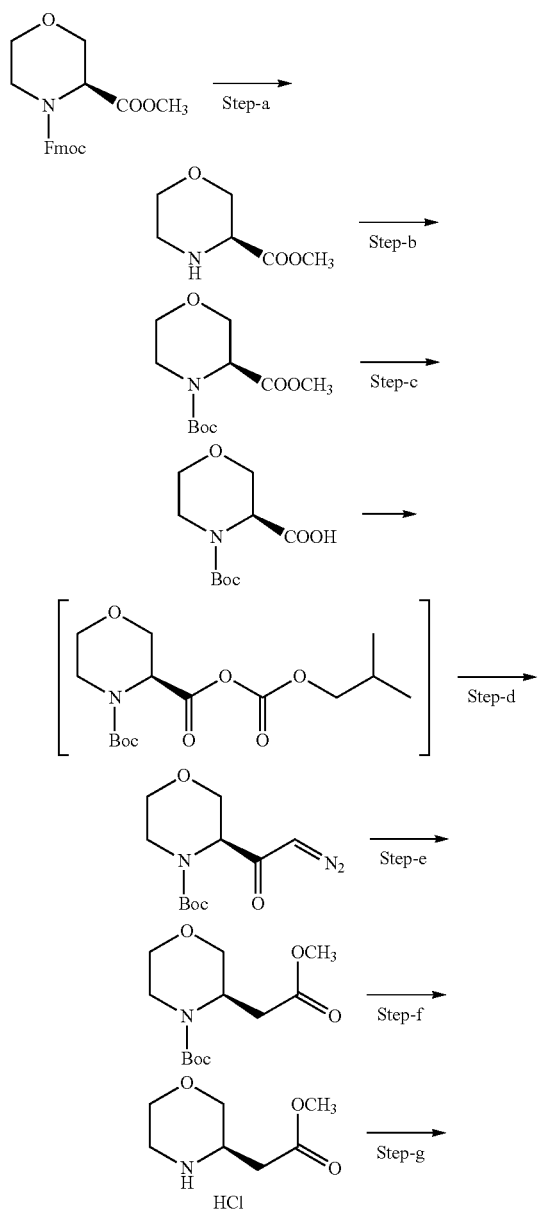

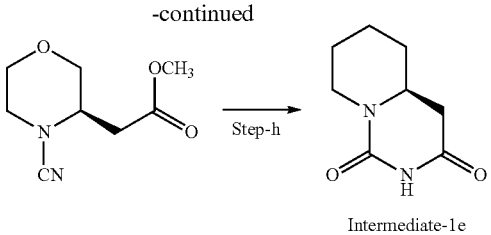

Intermediate-1e

Step-a: To the stirred solution of morpholine-3,4-dicarboxylic acid 4-(9H-fluoren-9-ylmethyl) ester 3-methyl ester (1.9 g, 5.17 mmol: prepared as per the procedures reported in *J. Org. Chem.* 2007, 72, 4254-4257) in methanol (21.0 mL) at r.t., 10% Pd—C(Palladium on carbon 0.9 g) was added and the reaction mass was stirred under nitrogen atmosphere for 16 h. The reaction mass was filtered over cloth/paper bed, the filtrate was evaporated under vacuum and the crude product thus obtained was purified by silica gel column chromatography to obtain Morpholine-3-carboxylic acid methyl ester (0.67 g) in 90% yield.
$^1$H NMR (400 MHZ, CDCl$_3$): δ 4.01 (dd, J=3.2, 11.2 Hz, 1H), 3.80-3.72 (m, 2H), 3.75 (s, 3H), 3.65-3.56 (m, 2H), 3.08-3.02 (m, 1H), 2.91-2.83 (m, 1H); Mass (m/z): 146.1 (M+H)$^+$.

Step-b: To the stirred solution of step-a compound (0.64 g, 4.45 mmol) in DCM (18.0 mL) cooled at 0° C., triethylamine (2.40 mL, 17.80 mmol), DMAP (54.0 mg, 0.44 mmol), and Boc anhydride (2.26 mL, 9.78 mmol) were added. The reaction mass was gradually warmed to r.t., and stirred for 16 h. The volatiles were removed under vacuum and the crude product was purified by silica gel column chromatography to obtain Morpholine-3,4-dicarboxylic acid 4-tert-butyl ester 3-methyl ester (0.75 g) in 69% yield. $^1$H NMR (400 MHZ, CDCl$_3$): δ 4.61-4.56 (m, 0.5H), 4.45-4.30 (m, 1.5H), 3.95-3.72 (m, 1.5H), 3.77 (s, 3H), 3.70-3.60 (m, 1.5H), 3.54-3.41 (m, 1H), 3.38-3.28 (m, 0.5H), 3.25-3.13 (m, 0.5H), 1.48 (s, 4.5H), 1.44 (s, 4.5H): Mass (m/z): 268.1 (M+Na)$^+$.

Step-c: To the stirred solution of step-b compound (0.75 g, 3.05 mmol) in a mixture of THF and water (1:1, 12 mL) at r.t., LiOH·H$_2$O (0.16 g, 3.66 mmol) was added. The reaction mass was stirred for 2 h before diluting it with diethyl ether and water. The two layers were separated and the aqueous layer was acidified with concentrated HCl to pH 2 and extracted with EtOAc. The organic layer was washed with brine solution, dried over anhydrous Na$_2$SO$_4$ and the solvent was removed under vacuum to obtain Morpholine-3,4-dicarboxylic acid 4-tert-butyl ester (0.64 g) in 90% yield. $^1$H NMR (400 MHZ, DMSO-d$_6$): δ 12.99 (bs, 1H), 4.34 (dd, J=2.4, 20.4 Hz, 1H), 4.18 (dd, J=12.0, 15.2 Hz, 1H), 3.86-3.72 (m, 1H), 3.60-3.50 (m, 2H), 3.40-3.34 (m, 1H), 3.05-2.95 (m, 1H), 1.40 (s, 4H), 1.36 (s, 5H); Mass (m/z): 254.3 (M+Na)$^+$.

Step-d: Step-c compound (0.64 g, 2.77 mmol) was converted to 3-(2-diazo-acetyl)-morpholine-4-carboxylic acid tert-butyl ester in quantitative yields by following the procedure as reported for step-a of intermediate-1b preparation. Mass (m/z): 278.3 (M+Na)$^+$.

Step-e: Step-d compound (0.90 g, 3.5 mmol) was converted to 3-methoxy carbonylmethyl-morpholine-4-carboxylic acid tert-butyl ester (0.15 g) in 17% yields by following the procedure as reported for step-b of intermediate-1b preparation. Mass (m/z): 260.2 (M+H)$^+$.

Step-f: Step-e compound (0.15 g, 0.58 mmol) was converted to Morpholin-3-yl-acetic acid methyl ester hydrochloride (0.11 g) in quantitative yields by following the procedure as reported for step-c of intermediate-1b preparation. ¹H NMR (400 MHZ, DMSO-d₆): δ 9.47 (bs, 1H), 9.28 (bs, 1H), 3.96-3.85 (m, 2H), 3.72-3.65 (m, 1H), 3.64 (s, 3H), 3.60-3.35 (m, 2H), 3.30-3.06 (m, 2H), 2.76-2.60 (m, 2H); Mass (m/z): 160.2 (M+H)⁺.

Step-g: Step-f compound (0.1 g, 0.6 mmol) was converted to (4-Cyano-morpholin-3-yl)-acetic acid methyl ester (0.07 g) in 59% yields by following the procedure as reported for step-d of intermediate-1b preparation. Mass (m/z): 185.1 (M+H)⁺.

Step-h: Step-g compound (0.07 g, 0.37 mmol) was converted to Tetrahydro-pyrimido[6,1-c][1,4]oxazine-6,8-dione (24.0 mg) in 38% yields by following the procedure as reported for step-e of intermediate-1b preparation. ¹H NMR (400 MHZ, CDCl₃): δ 7.49 (bs, 1H), 4.10-4.01 (m, 2H), 4.0-3.93 (m, 1H), 3.68-3.52 (m, 2H), 3.21 (t, J=11.2 Hz, 1H), 3.07-2.98 (m, 1H), 2.65 (dd, J=4.8, 16.8 Hz, 1H), 2.39 (dd, J=12.4, 16.8 Hz, 1H); Mass (m/z): 171.1 (M+H)⁺.

Intermediate-1f: Preparation of 6,8-dioxo-octa-hydro-pyrazino[1,2-c]pyrimidine-2-carboxylic acid benzyl ester

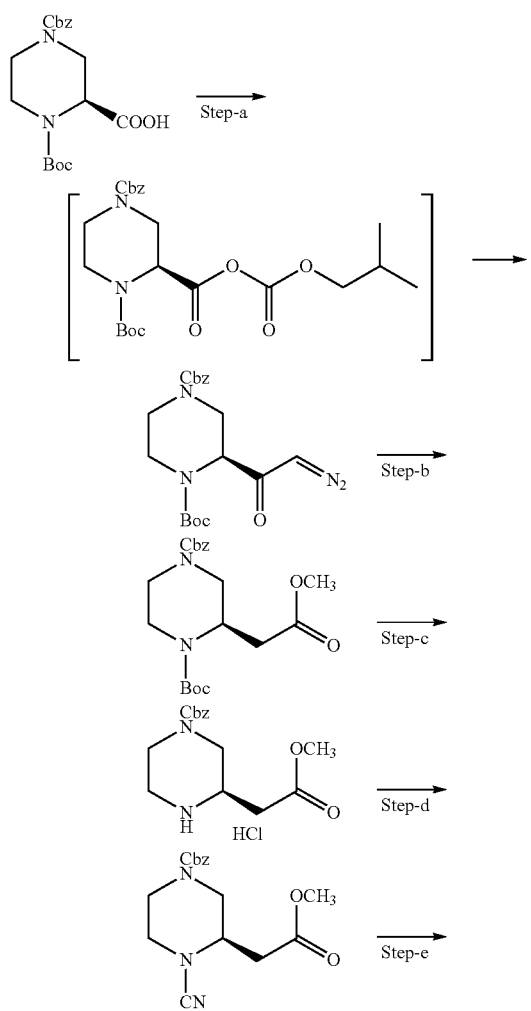

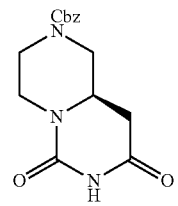

Intermediate-1f

Step-a: Commercially available S-piperazine-2-carboxylic acid was Cbz protected by following the procedure as reported in WO2012019426 followed by Boc protection as reported in Tetrahedron Letters 1989, 30, 5129-5132 to obtain piperazine-1,2,4-tricarboxylic acid 4-benzyl ester 1-tert-butyl ester. The compound obtained above was converted to 2-(2-diazo-acetyl)-piperazine-1,4-dicarboxylic acid 4-benzyl ester 1-tert-butyl ester by following the procedure as reported for step-a of intermediate-1b preparation. ¹H NMR (400 MHZ, CDCl₃): δ 7.40-7.30 (m, 5H), 5.50-5.36 (m, 1H), 5.20-5.08 (m, 2H), 4.70-4.50 (m, 2H), 4.08-3.85 (m, 2H), 3.25-3.08 (m, 2H), 3.06-2.95 (m, 1H), 1.47 (s, 9H); Mass (m/z): 389.1 (M+H)⁺.

Step-b: The compound of step-a was converted to 2-Methoxycarbonylmethyl-piperazine-1,4-dicarboxylic acid 4-benzyl ester 1-tert-butyl ester by following the procedure as reported for step-b of intermediate-1b preparation. ¹H NMR (400 MHZ, CDCl₃): δ 7.40-7.30 (m, 5H), 5.20-5.06 (m, 2H), 4.70-4.52 (m, 1H), 4.15-4.05 (m, 2H), 3.98-3.85 (m, 1H), 3.70-3.52 (m, 3H), 3.13-2.80 (m, 3H), 2.62-2.42 (m, 2H), 1.48 (s, 9H); Mass (m/z): 393.2 (M+H)⁺.

Step-c: The compound of step-b was converted to 3-Methoxycarbonylmethyl-piperazine-1-carboxylic acid benzyl ester hydrochloride by following the procedure as reported for step-c of intermediate-1b preparation. ¹H NMR (400 MHZ, CDCl₃): δ 7.40-7.30 (m, 5H), 5.20-5.10 (m, 2H), 4.30-4.15 (m, 1H), 3.73 (s, 3H), 3.60-3.05 (m, 6H), 2.96-2.86 (m, 1H), 2.70-2.58 (m, 1H); Mass (m/z): 293.1 (M+H)⁺.

Step-d: The compound of step-c was converted to 4-Cyano-3-methoxycarbonylmethyl-piperazine-1-carboxylic acid benzyl ester by following the procedure as reported for step-d of intermediate-1b preparation. ¹H NMR (400 MHZ, CDCl₃): δ 7.40-7.30 (m, 5H), 5.20-5.08 (m, 2H), 3.95-3.82 (m, 1H), 3.80-3.40 (m, 5H), 3.50-3.40 (m, 1H), 3.40-3.32 (m, 1H), 3.30-3.15 (m, 2H), 2.81 (dd, J=6.4, 16.8 Hz, 1H), 2.61 (dd, J=7.2, 16.8 Hz, 1H); Mass (m/z): 318.2 (M+H)⁺.

Step-e: The compound of step-d was converted to 6,8-Dioxo-octahydro-pyrazino[1,2-c]pyrimidine-2-carboxylic acid benzyl ester by following the procedure as reported for step-e of intermediate-1b preparation. ¹H NMR (400 MHz, DMSO-d₆): δ 10.35 (bs, 1H), 7.40-7.38 (m, 5H), 5.10 (s, 2H), 4.10-3.96 (m, 3H), 3.60-3.50 (m, 1H), 3.05-2.85 (m, 1H), 2.85-2.62 (m, 3H), 2.50-2.38 (m, 1H); Mass (m/z): 304.3 (M+H)⁺.

Intermediate-2a: Preparation of 8-benzo[d]isothiazol-3-yl-8-aza-5-azonia-spiro[4.5]decane bromide

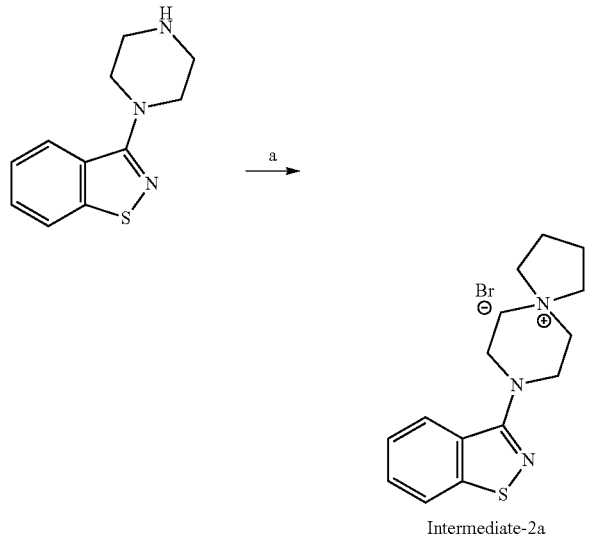

Intermediate-2a

A mixture of the 3-piperazin-1-yl-benzo[d]isothiazole (50.0 g, 227.98 mmol), 1,4-dibromobutane (60.5 g, 280.42 mmol), anhydrous $K_2CO_3$ (75.5 g, 547.15 mmol), and 18-crown-6 (0.6 g, 2.27 mmol) in EtOH (912 mL) was heated under reflux with stirring for 8 h. The hot reaction mixture was filtered, and the filtrate was concentrated under vacuum to about one-third of the initial volume, re-filtered, and cooled. The crystalline precipitate was collected and dried under vacuum at 100° C. to provide 58.9 g (73%) of the titled compound. Mp: 258-259° C.; $^1$H NMR (400 MHZ, DMSO-$d_6$): δ 8.20 (d, J=8.0 Hz, 1H), 8.13 (d, J=8.0 Hz, 1H), 7.61 (t, J=7.2 Hz, 1H), 7.50 (t, J=7.6 Hz, 1H), 3.86-3.80 (m, 4H), 3.78-3.65 (m, 8H), 2.20-2.08 (m, 4H); Mass (m/z): 274.3 (M)$^+$.

Intermediates-2b to 2e were prepared from 1-Benzo[b]thiophen-4-yl-piperazine, 5-Fluoro-4-piperidin-4-yl-1H-indole, 6-Fluoro-4-piperidin-4-yl-benzo[d]isoxazole, and 5-Methoxy-3-piperidin-4-yl-1H-indole using the procedure as described for Intermediate-2a with some non-critical variations.

| Intermediate no. | Chemical name and Structure | Analytical Characterization |
|---|---|---|
| 2b | 8-Benzo[b]thiophen-4-yl-8-aza-5-azonia-spiro[4.5]decane; bromide | $^1$H NMR (400 MHa, DMSO-$d_6$): δ 7.75 (d, J = 5.2 Hz, 1H), 7.69 (d, J = 8.0 Hz, 1H), 7.47 (d, J = 5.2 Hz, 1H), 7.30 (t, J = 7.8 Hz, 1H), 6.96 (d, J = 7.6 Hz, 1H), 3.86-3.80 (m, 4H), 3.78-3.65 (m, 8H), 2.20-2.08 (m, 4H); Mass (m/z): 273.1 (M)$^+$. |
| 2c | 8-(5-Fluoro-1H-indol-3-yl)-5-azonia-spiro[4.5]decane; bromide | $^1$H NMR (400 MHz, DMSO-$d_6$): δ 11.08 (bs, 1H), 7.42-7.33 (m, 2H), 7.30 (s, 1H), 6.94 (dt, J = 2.4, 9.2 Hz, 1H), 3.68-3.52 (m, 9H), 2.18-1.95 (m, 8H); Mass (m/z): 273.1 (M)$^+$. |
| 2d | 8-(6-Fluoro-benzo[d]isoxazol-3-yl)-5-azonia-spiro[4.5]decane; bromide | $^1$H NMR (400 MHz, DMSO-$d_6$): δ 8.14 (dd, J = 5.2, 8.8 Hz, 1H), 7.75 (d, J = 8.8 Hz, 1H), 7.34 (t, J = 9.2 Hz, 1H), 3.70-3.52 (m, 9H), 2.40-2.30 (m, 2H), 2.28-2.15 (m, 2H), 2.15-2.05 (m, 4H); Mass (m/z): 275.0 (M)$^+$. |

| Intermediate no. | Chemical name and Structure | Analytical Characterization |
|---|---|---|
| 2e | 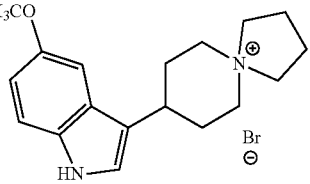<br>8-(5-Methoxy-1H-indol-3-yl)-5-azonia-spiro[4.5]decane; bromide | $^1$H NMR (400 MHz, DMSO-$d_6$): δ 10.78 (bs, 1H), 7.26 (d, J = 8.8 Hz, 1H), 7.17 (s, 1H), 6.94 (s, 1H), 6.74 (d, J = 8.8 Hz, 1H), 3.85-3.70 (m, 4H), 3.63 (s, 3H), 3.65-3.45 (m, 4H), 3.15-3.0 (m, 1H), 2.20-1.90 (m, 8H); Mass (m/z): 285.1 (M)$^+$. |
| 2f | 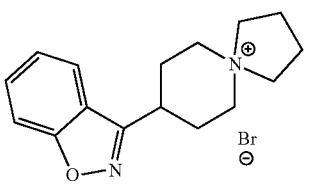 [SMILES: c1ccc2c(C3CC[N+]4(CCCC4)CC3)noc2c1 ; [Br-]]<br>8-Benzo[d]isoxazol-3-yl-5-azonia-spiro[4.5]decane; bromide | $^1$H NMR (400 MHz, DMSO-$d_6$): δ 8.06 (d, J = 8.0 Hz, 1H), 777 (d, J = 8.4 Hz, 1H), 7.70 (t, J = 7.6 Hz, 1H), 7.45 (t, J = 7.6 Hz, 1H), 3.70-3.50 (m, 9H), 2.40-2.30 (m, 2H), 2.30-2.18 (m, 2H), 2.16-2.04 (m, 4H); Mass (m/z): 256.8 (M)$^+$. |

Intermediate-3a: Preparation of Intermediate-3a

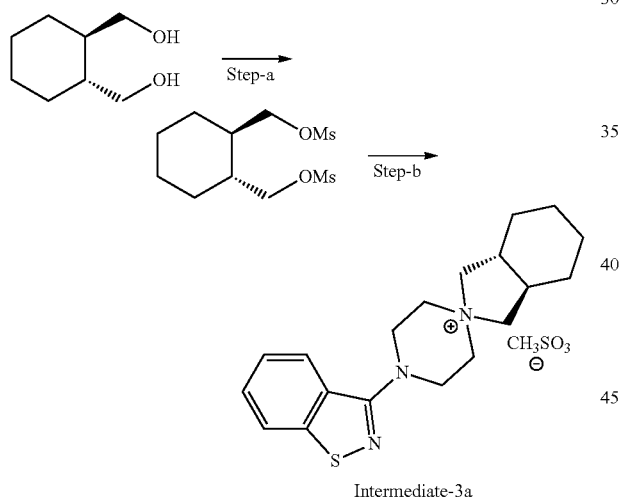

Intermediate-3a

Step-a: A stirred solution of commercially available (R, R)-trans-1,2-cyclohexanedimethanol (3.0 g, 20.8 mmol) in DCM (83.0 mL) cooled at 0° C., triethylamine (10.1 mL, 72.9 mmol) and methanesulfonyl chloride (4.4 mL, 57.2 mmol) were added. The reaction mixture was gradually warmed to r.t., and the mixture was stirred for 6 h. After completion of the reaction, the reaction mass was diluted with water and the two layers were separated. The organic layer was washed with brine solution, dried over anhydrous $Na_2SO_4$ and the solvent was removed under vacuum to obtain (1R, 2R)-1,2-bis (methanesulfonyloxymethyl) cyclohexane as a solid (5.5 g) in 90% yield. $^1$H-NMR (CDCl$_3$): δ 4.32-4.25 (m, 2H), 4.21-4.16 (m, 2H), 3.0 (s, 6H), 1.86-1.75 (m, 4H), 1.73-1.68 (m, 1H), 1.63-1.52 (m, 1H), 1.35-1.20 (m, 4H); Mass (m/z): 323.0 (M+Na)$^+$.

Step-b: To a stirred solution of commercially available 3-piperazin-1-yl-benzo[d]isothiazole (1.0 g, 4.56 mmol) in toluene (20.0 mL) at r.t., solid (1R, 2R)-1,2-bis (methanesulfonyloxymethyl) cyclohexane as obtained in step-a above (13.7 g, 45.6 mmol) was added and the reaction mass was stirred under reflux for 3 h. The reaction mass then cooled to r.t. and the volatiles were removed under vacuum. The crude reaction mass was triturated with diethyl ether and the obtained solids were dried under vacuum which afforded intermediate 3a (0.98 g) in quantitative yields. $^1$H-NMR (DMSO-$d_6$): δ 8.20 (d, J=8.0 Hz, 1H), 8.12 (d, J=8.0 Hz, 1H), 7.61 (t, J=7.2 Hz, 1H), 7.50 (t, J=7.6 Hz, 1H), 4.0-3.92 (m, 2H), 3.88-3.65 (m, 8H), 3.33 (s, 3H), 3.28-3.18 (m, 2H), 1.96-1.75 (m, 6H), 1.30-1.10 (m, 4H); Mass (m/z): 328.1 (M)$^+$.

Intermediate-3b: Preparation of Intermediate-3b

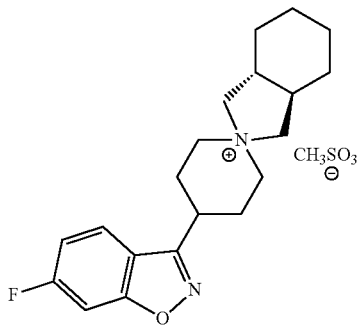

Intermediate-3b was prepared by reacting 6-Fluoro-3-piperidin-4-yl-benzo[d]isoxazole and (1R, 2R)-1,2-bis (methanesulfonyloxymethyl) cyclohexane by following the procedure as reported for step-b of intermediate-3a preparation in quantitative yields. $^1$H-NMR (DMSO-$d_6$): δ 8.11 (dd, J=5.6, 8.8 Hz, 1H), 7.75 (dd, J=1.2, 9.2 Hz, 1H), 7.37 (dd, J=1.2, 9.2 Hz, 1H), 4.03-3.97 (m, 1H), 3.88-3.82 (m, 1H), 3.78-3.70 (m, 1H), 3.65-3.50 (m, 5H), 3.34 (s, 3H), 2.40-2.23 (m, 4H), 2.20-2.08 (m, 1H), 1.95-1.75 (m, 6H), 1.30-1.10 (m, 4H); Mass (m/z): 329.1 (M)+.

Intermediate-4a: Preparation of 3-[4-(3-chloro-propyl)-piperazin-1-yl]-benzo[d]isothiazole

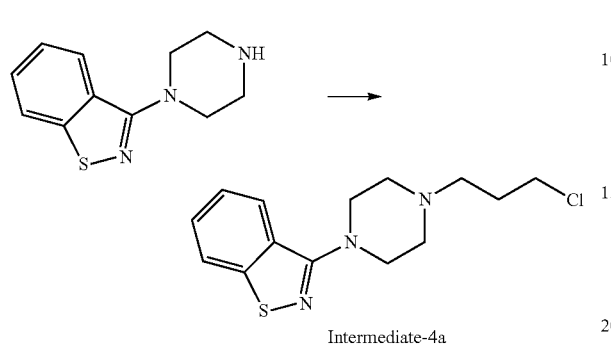

Intermediate-4a

To a stirred suspension of commercially available 3-Piperazin-1-yl-benzo[d]isothiazole (10.0 g, 45.6 mmol), KOH flakes (7.6 g, 137.0 mmol) and a 1:1 mixture of THF and water (100.0 mL) was added 1-bromo-3-chloro propane (19.6 g, 137.0 mmol) at r.t. The mixture was stirred for 16 h and the mixture was extracted with EtOAc. The combined organic extracts were washed with brine solution, dried over anhydrous $Na_2SO_4$ and the solvent was evaporated under vacuum. The residue obtained was purified by silica gel column chromatography to obtain intermediate-4a (9.68 g) in 72% yield. $^1$H NMR (400 MHZ, DMSO-$d_6$): δ 8.06-8.03 (m, 2H), 7.53 (dd, J=7.2 Hz, 1H), 7.41 (dd, J=7.6 Hz, 1H), 3.72-3.68 (m, 2H), 3.45-3.43 (m, 4H), 2.60-2.56 (m, 4H), 2.52-2.46 (m, 2H), 1.96-1.90 (m, 2H); Mass (m/z): 296.1, 298.1 (M+H)+.

Using a similar procedure as given in the preparation of intermediate-4a and some non-critical variations intermediate-4b, 4c and 4d were prepared.

Intermediate-4b: Preparation of 3-[1-(3-chloro-propyl)-piperidin-4-yl]-6-fluoro-benzo[d]isoxazole

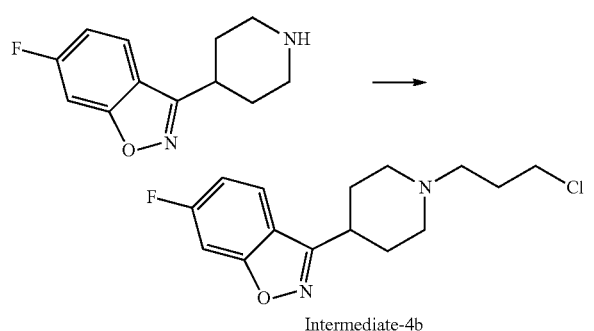

Intermediate-4b

Yield: 7.9 g, (62%); $^1$H NMR (400 MHZ, DMSO-$d_6$): δ 7.79 (s, 1H), 7.47-7.45 (m, 1H), 7.26-7.21 (m, 1H), 4.63-4.53 (m, 2H), 3.75-3.65 (m, 2H), 3.19-3.11 (m, 2H), 3.03-2.95 (m, 2H), 2.74-2.63 (m, 1H), 2.29-2.21 (m, 2H), 2.07-2.01 (m, 2H), 1.85-1.78 (m, 2H); Mass (m/z): 297.2, 299.2 (M+H)+.

Intermediate-4c: Preparation of 3-[1-(3-Chloro-propyl)-piperidin-4-yl]-5-fluoro-1H-indole

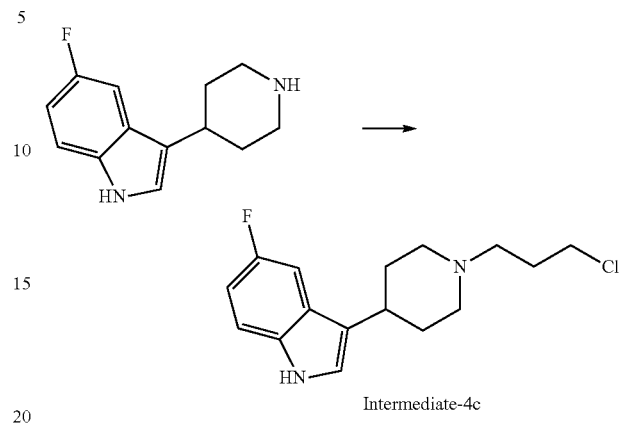

Intermediate-4c

Yield: 2.3 g, (65%); $^1$H NMR (400 MHZ, DMSO-$d_6$): δ 10.99 (s, 1H), 7.43 (dd, J=2, 10.4 Hz, 1H), 7.36 (dd, J=4.8, 8.8 Hz, 1H), 7.21 (d, J=2.0 Hz, 1H), 6.94 (dt, J=2.4, 9.2 Hz, 1H), 4.62 (t, J=7.6 Hz, 2H), 3.75-3.65 (m, 2H), 3.19-3.11 (m, 2H), 3.03-2.95 (m, 2H), 2.74-2.63 (m, 1H), 2.29-2.21 (m, 2H), 2.07-2.01 (m, 2H), 1.85-1.78 (m, 2H); Mass (m/z): 295.2, 297.2 (M+H)+.

Intermediate-4d: Preparation of 3-[1-(3-chloro-propyl)-piperidin-4-yl]-benzo[d]isoxazole

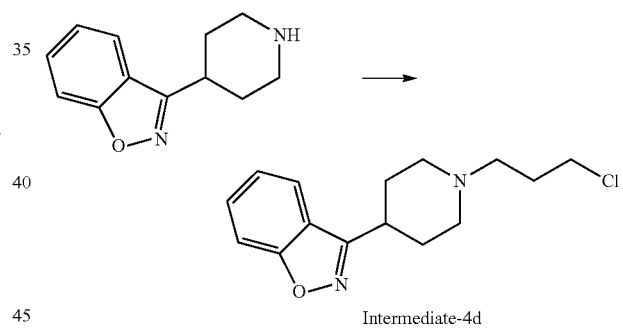

Intermediate-4d

Yield: 0.3 g, (44%); $^1$H NMR (400 MHZ, DMSO-$d_6$): δ 8.07 (d, J=8.0 Hz, 1H), 7.77 (d, J=8.3 Hz, 1H), 7.68 (t, J=7.6 Hz, 1H), 7.43 (t, J=7.6 Hz, 1H), 4.65-4.55 (m, 2H), 3.75-3.65 (m, 2H), 3.20-3.10 (m, 2H), 3.05-2.95 (m, 2H), 2.75-2.65 (m, 1H), 2.30-2.20 (m, 2H), 2.08-2.0 (m, 2H), 1.85-1.75 (m, 2H); Mass (m/z): 279.2, 281.2 (M+H)+.

Example-1: 2-[4-(4-Benzo[d]isothiazol-3-yl-piperazin-1-yl)-butyl]-tetrahydro-pyrrolo[1,2-c]pyrimidine-1,3-dione

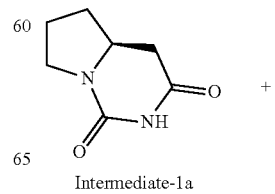

Intermediate-1a

Example-2: 2-[4-(4-Benzo[d]isothiazol-3-yl-piperazin-1-yl)-butyl]-tetrahydro-pyrrolo[1,2-c]pyrimidine-1,3-dione oxalate

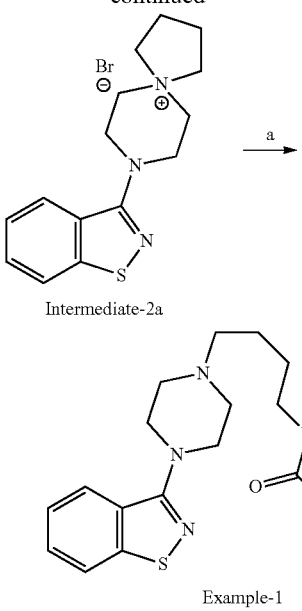

Intermediate-2a

Example-1

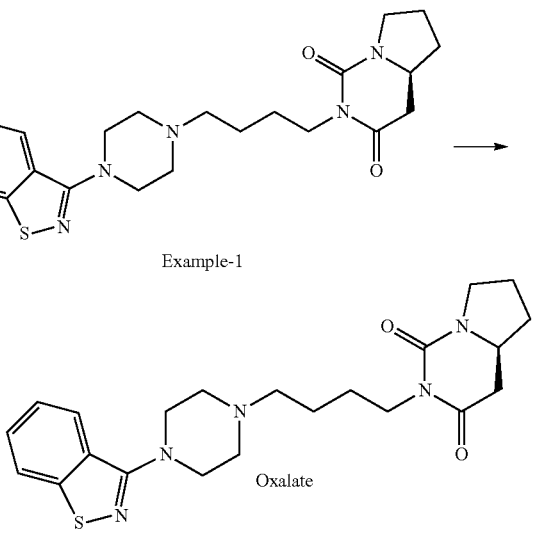

Example-1

Example-2

A mixture of Intermediate-2a (114.0 g, 321.78 mmol), Intermediate-1a (45.1 g, 292.5 mmol), anhydrous $K_2CO_3$ (80.7 g, 585.0 mmol), and 18-crown-6 (0.77 g, 2.92 mmol) in xylene (1170 mL) was stirred and heated under reflux for 3 h. The hot mixture was filtered through cloth/paper; the cloth/paper was washed with EtOAc. The combined organic layer was washed with water and brine solution. The organic layer thus obtained was dried over anhydrous $Na_2SO_4$ and the solvent was removed under vacuum. The crude product was triturated with pentane followed by 3% EtOAc in hexane to obtain above titled compound (87.2 g) in 69.7% yield. $^1$H NMR (400 MHZ, $CDCl_3$): δ 7.91 (d, J=8.0 Hz, 1H), 7.81 (d, J=8.4 Hz, 1H), 7.46 (t, J=7.2 Hz, 1H), 7.35 (t, J=7.6 Hz, 1H), 3.88-3.79 (m, 1H), 3.78-3.61 (m, 2H), 3.59-3.48 (m, 5H), 2.86 (dd, J=4.0, 16.0 Hz, 1H), 2.70-2.63 (m, 4H), 2.49-2.42 (m, 4H), 2.43 (dd, J=14.0, 16.0 Hz, 1H), 2.31-2.23 (m, 1H), 2.12-2.02 (m, 1H), 1.96-1.81 (m, 1H), 1.68-1.51 (m, 4H); Mass (m/z): 428.1 $(M+H)^+$.

The Example 1 (87.0 g) was converted to the oxalate salt by treating with one equivalent of oxalic acid in isopropanol for 12 h to afford Example 2 (112.3 g) in quantitative yield. $^1$H NMR (400 MHZ, DMSO-$d_6$): δ 8.11 (d, J=7.6 Hz, 1H), 8.10 (d, J=7.6 Hz, 1H), 7.58 (t, J=7.2 Hz, 1H), 7.46 (t, J=8.0 Hz, 1H), 3.73-3.55 (m, 7H), 3.49-3.42 (m, 1H), 3.41-3.32 (m, 1H), 3.23-3.09 (m, 4H), 2.97-2.87 (m, 2H), 2.74 (dd, J=4.0, 16.0 Hz, 1H), 2.59 (dd, J=14.0, 16.0 Hz, 1H), 2.19-2.11 (m, 1H), 2.0-1.91 (m, 1H), 1.86-1.71 (m, 1H), 1.65-1.45 (m, 5H): Mass (m/z): 428.2 $(M+H)^+$; HPLC purity: 99.6%.

The following examples 3 to 22 were prepared by using the procedure as described for examples-1 and examples-2 preparations using appropriate intermediates with some non-critical variations (fumarate salts of compounds were prepared by reacting with fumaric acid using the procedure of example 2).

| Example Number | Chemical name and Structure | Characterization data |
|---|---|---|
| 3 | 2-[4-(4-Benzo[b]thiophen-4-yl-piperazin-1-yl)-butyl]-tetrahydro-pyrrolo[1,2-c]pyrimidine-1,3-dione | $^1$H NMR (400 MHz, $CDCl_3$): δ 7.55 (d, J = 8.0 Hz, 1H), 7.41-7.37 (m, 2H), 7.28 (t, J = 7.6 Hz, 1H), 7.47 (t, J = 5.2 Hz, 1H), 6.90 (d, J = 7.6 Hz, 1H), 3.90-3.80 (m, 1H), 3.78-3.60 (m, 2H), 3.57-3.47 (m, 1H), 3.30-3.10 (m, 4H), 2.86 (dd, J = 4.0, 16.0 Hz, 1H), 2.80-2.60 (m, 4H), 2.55-2.45 (m, 2H), 2.43 (dd, J = 13.6, 16.0 Hz, 1H), 2.32-2.22 (m, 1H), 2.12-2.02 (m, 1H), 1.95-1.81 (m, 1H), 1.70-1.50 (m, 5H); Mass (m/z): 427.2 $(M + H)^+$. |

-continued

| Example Number | Chemical name and Structure | Characterization data |
|---|---|---|
| 4 | 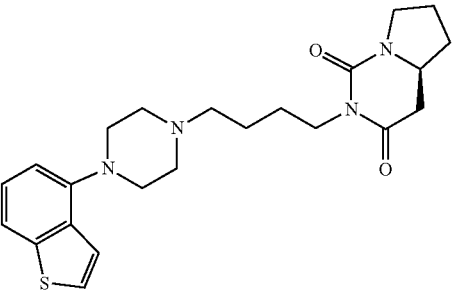 [SMILES: O=C1C[C@@H]2CCCN2C(=O)N1CCCCN1CCN(c2cccc3sccc23)CC1]<br>Oxalate<br>2-[4-(4-Benzo[b]thiophen-4-yl-piperazin-1-yl)-butyl]-tetrahydro-pyrrolo[1,2-c]pyrimidine-1,3-dione oxalate | $^1$H NMR (400 MHz, DMSO-d$_6$): δ 7.75 (d, J = 5.3 Hz, 1H), 7.69 (d, J = 8.0 Hz, 1H), 7.47 (d, J = 5.3 Hz, 1H), 7.30 (t, J = 7.8 Hz, 1H), 6.96 (d, J = 7.6 Hz, 1H), 3.78-3.65 (m, 6H), 3.65-3.56 (m, 1H), 3.50-3.40 (m, 1H), 3.40-3.30 (m, 1H), 3.25-3.10 (m, 4H), 3.02-2.90 (m, 2H), 2.80-2.70 (m, 1H), 2.62-2.50 (m, 1H), 2.20-2.10 (m, 1H), 2.02-1.92 (m, 1H), 1.88-1.72 (m, 1H), 1.68-1.45 (m, 5H); Mass (m/z): 427.2 (M + H)$^+$. |
| 5 | 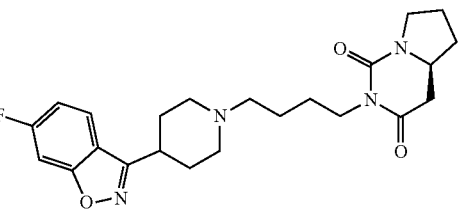<br>2-{4-[4-(6-Fluoro-benzo[d]isoxazol-3-yl)-piperidin-1-yl]-butyl}-tetrahydro-pyrrolo[1,2-c]pyrimidine-1,3-dione | $^1$H NMR (400 MHz, CDCl$_3$): δ 7.75 (s, 1H), 7.24 (d, J = 8.8 Hz, 1H), 7.05 (t, J = 8.4 Hz, 1H), 3.90-3.80 (m, 1H), 3.80-3.60 (m, 3H), 3.58-3.48 (m, 1H), 3.20-3.02 (m, 3H), 2.90-2.76 (m, 1H), 2.55-2.35 (m, 3H), 2.32-2.01 (m, 8H), 1.98-1.80 (m, 1H), 1.80-1.52 (m, 5H); Mass (m/z): 429.1 (M + H)$^+$. |
| 6 | 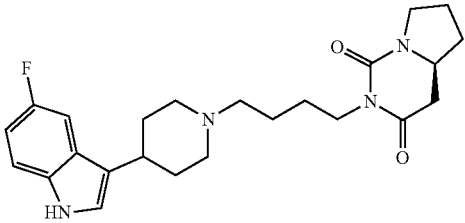<br>2-{4-[4-(5-Fluoro-1H-indol-3-yl)-piperidin-1-yl]-butyl}-tetrahydro-pyrrolo[1,2-c]pyrimidine-1,3-dione | $^1$H NMR (400 MHz, CDCl$_3$): δ 8.19 (bs, 1H), 7.32-7.18 (m, 2H), 7.06 (s, 1H), 6.97-6.89 (m, 1H), 3.90-3.81 (m, 1H), 3.80-3.70 (m, 2H), 3.68-3.62 (m, 2H), 3.58-3.45 (m, 2H), 3.20-3.10 (m, 2H), 2.90-2.82 (m, 2H), 2.80-2.68 (m, 2H), 2.55-2.38 (m, 3H), 2.32-2.22 (m, 1H), 2.15-2.02 (m, 2H), 1.97-1.82 (m, 1H), 1.82-1.70 (m, 2H), 1.70-1.52 (m, 4H); Mass (m/z): 427.1 (M + H)$^+$. |
| 7 | 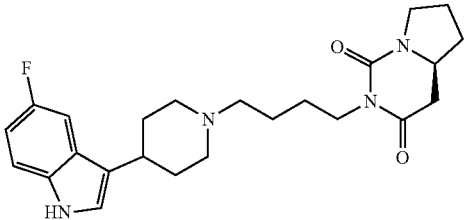 [SMILES: O=C1C[C@@H]2CCCN2C(=O)N1CCCCN1CCC(c2c[nH]c3ccc(F)cc23)CC1]<br>Oxalate<br>2-{4-[4-(5-Fluoro-1H-indol-3-yl)-piperidin-1-yl]-butyl}-tetrahydro-pyrrolo[1,2-c]pyrimidine-1,3-dione oxalate | $^1$H NMR (400 MHz, DMSO-d$_6$): δ 8.30 (bs, 1H), 7.33-7.20 (m, 2H), 7.05 (s, 1H), 6.97-6.89 (m, 1H), 4.20-3.98 (m, 1H), 3.80-3.70 (m, 2H), 3.68-3.62 (m, 2H), 3.58-3.45 (m, 2H), 3.21-3.12 (m, 2H), 2.90-2.82 (m, 2H), 2.80-2.68 (m, 2H), 2.55-2.38 (m, 3H), 2.32-2.22 (m, 1H), 2.15-2.02 (m, 2H), 1.97-1.82 (m, 1H), 1.82-1.70 (m, 2H), 1.70-1.52 (m, 4H); Mass (m/z): 427.1 (M + H)$^+$. |
| 8 | 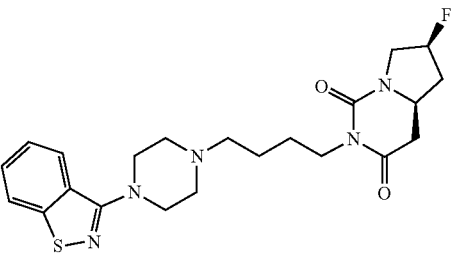 [SMILES: O=C1C[C@@H]2C[C@H](F)CN2C(=O)N1CCCCN1CCN(c2nsc3ccccc23)CC1] | $^1$H NMR (400 MHz, CDCl$_3$): δ 7.91 (d, J = 8.0 Hz, 1H), 7.81 (d, J = 8.4 Hz, 1H), 7.46 (t, J = 7.2 Hz, 1H), 7.35 (t, J = 7.6 Hz, 1H), 5.40-5.15 (m, 1H), 4.23-4.10 (m, 1H), 3.95-3.80 (m, 2H), 3.80-3.65 (m, 2H), 3.62-3.45 (m, 4H), 2.84 (dd, J = 4.0, 16.0 Hz, 1H), 2.75-2.55 (m, 5H), 2.50-2.40 (m 3H), 2.20-2.08 (m, 1H), 1.70-1.50 (m, 4H); Mass (m/z): 446.2 (M + H)$^+$. |

| Example Number | Chemical name and Structure | Characterization data |
|---|---|---|
| 9 | 2-[4-(4-Benzo[d]isothiazol-3-yl-piperazin-1-yl)-butyl]-6-fluoro-tetrahydro-pyrrolo[1,2-c]pyrimidine-1,3-dione<br>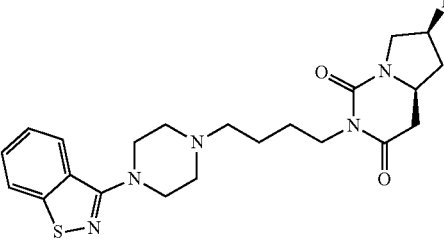<br>Oxalate<br>2-[4-(4-Benzo[d]isothiazol-3-yl-piperazin-1-yl)-butyl]-6-fluoro-tetrahydro-pyrrolo[1,2-c]pyrimidine-1,3-dione oxalate | $^1$H NMR (400 MHz, CDCl$_3$): δ 7.86 (d, J = 8.4 Hz, 1H), 7.82 (d, J = 8.4 Hz, 1H), 7.51 (t, J = 7.2 Hz, 1H), 7.40 (t, J = 7.6 Hz, 1H), 5.40-5.17 (m, 1H), 4.20-4.06 (m, 1H), 4.05-3.90 (m, 4H), 3.90-3.70 (m, 4H), 3.13-3.07 (m, 2H), 2.82 (dd, J = 4.0, 16.0 Hz, 1H), 2.67 (dd, J = 14.0, 16.0 Hz, 1H), 2.60-2.48 (m, 2H), 2.18-2.05 (m, 2H), 1.90-1.75 (m, 4H), 1.70-1.60 (m, 2H); Mass (m/z): 446.2 (M + H)$^+$. |
| 10 | 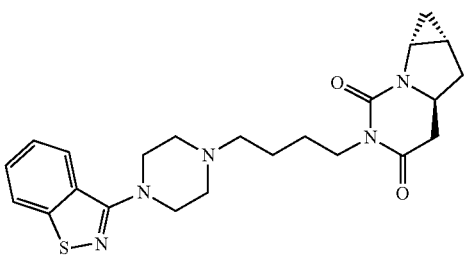 [SMILES: O=C1C[C@@H]2C[C@H]3C[C@H]3N2C(=O)N1CCCCN1CCN(c2nsc3ccccc23)CC1]<br>3-[4-(4-Benzo[d]isothiazol-3-yl-piperazin-1-yl)-1b,3-butyl]-hexahydro-diaza-cyclopropa[a]indene-2,4-dione | $^1$H NMR (400 MHz, CDCl$_3$): δ 7.91 (d, J = 8.0 Hz, 1H), 7.81 (d, J = 8.0 Hz, 1H), 7.47 (t, J = 7.2 Hz, 1H), 7.35 (t, J = 7.6 Hz, 1H), 4.30-4.20 (m, 1H), 3.88-3.80 (m, 2H), 3.80-3.67 (m, 2H), 3.60-3.50 (m, 4H), 3.50-3.45 (m, 1H), 2.75-2.56 (m, 6H), 2.50-2.38 (m, 2H), 2.30-2.20 (m, 1H), 1.70-1.50 (m, 4H), 1.20-1.12 (m, 1H), 0.56-0.50 (m, 1H); Mass (m/z): 440.2 (M + H)$^+$. |
| 11 | 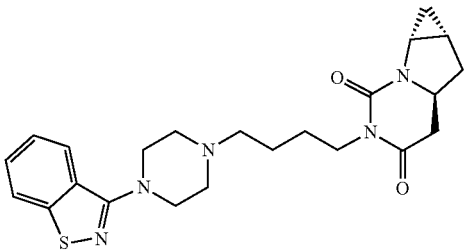<br>Oxalate<br>3-[4-(4-Benzo[d]isothiazol-3-yl-piperazin-1-yl)-butyl]-hexahydro-1b,3-diaza-cyclopropa[a]indene-2,4-dione oxalate | $^1$H NMR (400 MHz, DMSO-d$_6$): δ 8.11 (d, J = 6.9 Hz, 1H), 8.10 (d, J = 7.1 Hz, 1H), 7.58 (t, J = 7.2 Hz, 1H), 7.46 (t, J = 7.6 Hz, 1H), 4.30-4.18 (m, 1H), 3.75-3.50 (m, 6H), 3.45-3.40 (m, 2H), 3.20-3.02 (m, 5H), 2.98-2.82 (m, 2H), 2.70-2.32 (m, 2H), 1.68-1.45 (m, 5H), 1.05-0.98 (m, 1H), 0.60-0.53 (m, 1H); Mass (m/z): 440.2 (M + H)$^+$. |
| 12 | 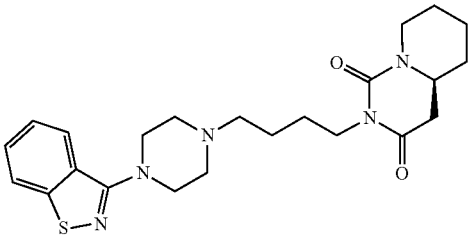 [SMILES: O=C1C[C@@H]2CCCCN2C(=O)N1CCCCN1CCN(c2nsc3ccccc23)CC1]<br>2-[4-(4-Benzo[d]isothiazol-3-yl-piperazin-1-yl)-butyl]-hexahydro-pyrido[1,2-c]pyrimidine-1,3-dione | $^1$H NMR (400 MHz, CDCl$_3$): δ 7.90 (d, J = 8.0 Hz, 1H), 7.81 (d, J = 8.0 Hz, 1H), 7.46 (t, J = 7.6 Hz, 1H), 7.35 (t, J = 7.6 Hz, 1H), 4.38-4.30 (m, 1H), 3.90-3.75 (m, 2H), 3.68-3.52 (m, 4H), 3.40-3.30 (m, 1H), 2.85-2.63 (m, 6H), 2.58-2.42 (m, 3H), 1.92-1.75 (m, 3H), 1.70-1.40 (m, 5H), 1.38-1.20 (m, 2H); Mass (m/z): 442.2 (M + H)$^+$; HPLC purity: 99.03%. |

| Example Number | Chemical name and Structure | Characterization data |
|---|---|---|
| 13 | 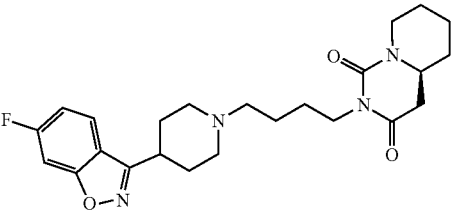 [SMILES: O=C1C[C@@H]2CCCCN2C(=O)N1CCCCN1CCC(c2noc3cc(F)ccc23)CC1]

2-{4-[4-(6-Fluoro-benzo[d]isoxazol-3-yl)-piperidin-1-yl]-butyl}-hexahydro-pyrido[1,2-c]pyrimidine-1,3-dione | $^1$H NMR (400 MHz, CDCl$_3$): δ 7.91 (bs, 1H), 7.23 (d, J = 10.8 Hz, 1H), 7.10 (t, J = 8.4 Hz, 1H), 4.38-4.28 (m, 1H), 3.90-3.76 (m, 2H), 3.45-3.20 (m, 3H), 2.90-2.18 (m, 4H), 2.56-2.46 (m, 2H), 1.90-1.72 (m, 6H), 1.72-1.60 (m, 7H), 1.55-1.40 (m, 2H), 1.38-1.22 (m, 1H); Mass (m/z): 443.2 (M + H)$^+$; HPLC purity: 96.30%. |
| 14 | 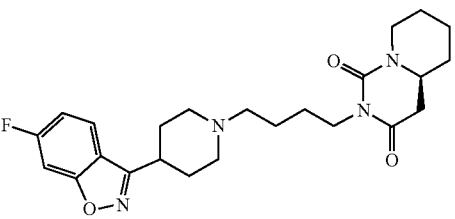

Fumarate

2-{4-[4-(6-Fluoro-benzo[d]isoxazol-3-yl)-piperidin-1-yl]-butyl}-hexahydro-pyrido[1,2-c]pyrimidine-1,3-dione fumarate | $^1$H NMR (400 MHz, DMSO-d$_6$): δ 8.06-7.98 (m, 1H), 7.70 (d, J = 8.8 Hz, 1H), 7.28 (t, J = 8.4 Hz, 1H), 6.60 (s, 2H), 4.16-4.08 (m, 1H), 3.72-3.60 (m, 2H), 3.40-3.15 (m, 5H), 3.12-3.03 (m, 2H), 2.81 (dd, J = 5.2, 16.8 Hz, 1H), 2.74-2.64 (m, 1H), 2.56-2.42 (m, 2H), 2.38-2.26 (m, 2H), 2.12-2.03 (m, 2H), 1.96-1.82 (m, 2H), 1.78-1.63 (m, 3H), 1.50-1.43 (m, 2H), 1.42-1.28 (m, 2H), 1.25-1.12 (m, 1H); Mass (m/z): 443.3 (M + H)$^+$; HPLC purity: 99.03%. |
| 15 | 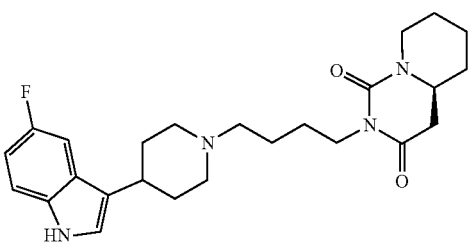 [SMILES: O=C1C[C@@H]2CCCCN2C(=O)N1CCCCN1CCC(c2c[nH]c3ccc(F)cc23)CC1]

2-{4-[4-(5-Fluoro-1H-indol-3-yl)-piperidin-1-yl]-butyl}-hexahydro-pyrido[1,2-c]pyrimidine-1,3-dione | $^1$H NMR (400 MHz, CDCl$_3$): δ 8.08 (bs, 1H), 7.26 (bs, 1H), 7.0 (bs, 1H), 6.91 (t, J = 8.0 Hz, 1H), 4.40-4.28 (m, 1H), 3.90-3.70 (m, 2H), 3.40-3.25 (m, 1H), 3.12-3.0 (m, 2H), 2.85-2.63 (m, 3H), 2.55-2.35 (m, 3H), 2.20-1.95 (m, 6H), 1.90-1.70 (m, 5H), 1.55-1.40 (m, 2H), 1.35-1.20 (m, 2H), 0.95-0.80 (m, 1H); Mass (m/z): 441.2 (M + H)$^+$; HPLC purity: 96.39%. |
| 16 | 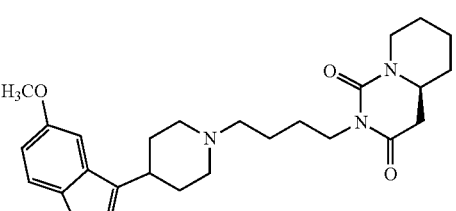

2-{4-[4-(5-Methoxy-1H-indol-3-yl)-piperidin-1-yl]-butyl}-hexahydro-pyrido[1,2-c]pyrimidine-1,3-dione | $^1$H NMR (400 MHz, CDCl$_3$): δ 7.85 (bs, 1H), 7.26 (d, J = 8.4 Hz, 1H), 7.06 (s, 1H), 6.95 (s, 1H), 6.85 (t, J = 8.4 Hz, 1H), 4.38-4.30 (m, 1H), 3.87 (s, 3H), 3.90-3.78 (m, 2H), 3.38-3.28 (m, 1H), 3.12-3.02 (m, 2H), 2.85-2.65 (m, 3H), 2.54-2.40 (m, 3H), 2.20-2.10 (m, 2H), 2.10-2.0 (m, 2H), 1.90-1.75 (m, 5H), 1.70-1.40 (m, 5H), 1.38-1.20 (m, 2H); Mass (m/z): 453.3 (M + H)$^+$; HPLC purity: 95.64%. |
| 17 | 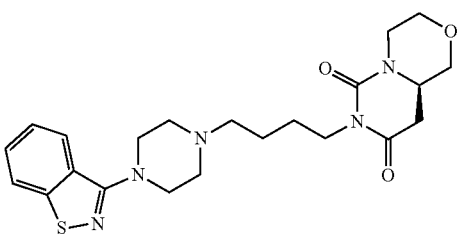 [SMILES: O=C1C[C@@H]2COCCN2C(=O)N1CCCCN1CCN(c2nsc3ccccc23)CC1]

7-[4-(4-Benzo[d]isothiazol-3-yl-piperazin-1-yl)-butyl]-tetrahydro-pyrimido[6,1-c][1,4]oxazine-6,8-dione | $^1$H NMR (400 MHz, CDCl$_3$): δ 8.09 (d, J = 7.6 Hz, 1H), 8.06 (d, J = 7.6 Hz, 1H), 7.58 (t, J = 7.2 Hz, 1H), 7.46 (t, J = 7.5 Hz, 1H), 3.96-3.92 (m, 1H), 3.88-3.82 (m, 2H), 3.76-3.71 (m, 1H), 3.64-3.61 (m, 1H), 3.60-3.55 (m, 4H), 3.57-3.50 (m, 6H), 3.30-3.0 (m, 2H), 2.80-2.65 (m, 2H), 2.60-2.50 (m, 2H), 1.60-1.45 (m, 4H); Mass (m/z): 444.2 (M + H)$^+$. |

-continued

| Example Number | Chemical name and Structure | Characterization data |
|---|---|---|
| 18 | 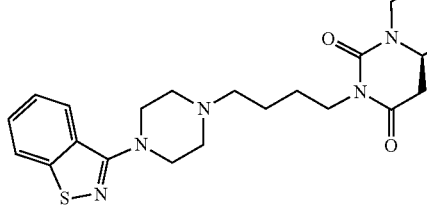<br>Oxalate<br><br>7-[4-(4-Benzo[d]isothiazol-3-yl-piperazin-1-yl)-butyl]-tetrahydro-pyrimido[6,1-c][1,4]oxazine-6,8-dione oxalate | $^1$H NMR (400 MHz, DMSO-d$_6$): δ 8.09 (d, J = 7.6 Hz, 1H), 8.06 (d, J = 7.6 Hz, 1H), 7.58 (t, J = 7.2 Hz, 1H), 7.46 (t, J = 7.5 Hz, 1H), 3.96-3.92 (m, 1H), 3.88-3.82 (m, 2H), 3.76-3.71 (m, 1H), 3.64-3.61 (m, 1H), 3.60-3.55 (m, 4H), 3.57-3.50 (m, 6H), 3.30-3.0 (m, 2H), 2.80-2.65 (m, 2H), 2.60-2.50 (m, 2H), 1.60-1.45 (m, 4H); Mass (m/z): 444.2 (M + H)$^+$; HPLC purity: 98.5%. |
| 19 | 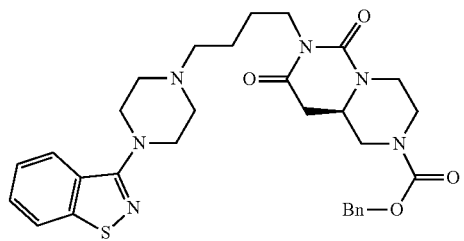 [SMILES: O=C(OCc1ccccc1)N1CCN2C(=O)N(CCCCN3CCN(c4nsc5ccccc45)CC3)C(=O)C[C@@H]2C1]<br><br>7-[4-(4-Benzo[d]isothiazol-3-yl-piperazin-1-yl)-butyl]-6,8-dioxo-octahydro-pyrazino[1,2-c]pyrimidine-2-carboxylic acid benzyl ester | $^1$H NMR (400 MHz, CDCl$_3$): δ 7.91 (d, J = 8.0 Hz, 1H), 7.89 (d, J = 8.0 Hz, 1H), 7.46 (t, J = 7.2 Hz, 1H), 7.40-7.30 (m, 3H), 7.15-7.06 (m, 3H), 5.15 (s, 2H), 4.30-4.15 (m, 3H), 3.90-3.72 (m, 2H), 3.60-3.55 (m, 4H), 3.52-3.42 (m, 1H), 3.08-2.86 (m, 2H), 2.80-2.68 (m, 4H), 2.68-2.62 (m, 4H), 2.52-2.40 (m, 2H), 1.66-1.50 (m, 3H); Mass (m/z): 577.4 (M + H)$^+$. |
| 20 | 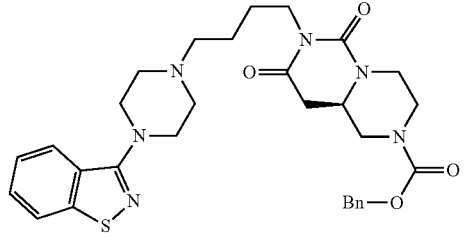<br>Fumarate<br><br>7-[4-(4-Benzo[d]isothiazol-3-yl-piperazin-1-yl)-butyl]-6,8-dioxo-octahydro-pyrazino[1,2-c]pyrimidine-2-carboxylic acid benzyl ester fumarate | $^1$H NMR (400 MHz, DMSO-d$_6$): δ 11.0 (bs, 2H), 8.10-8.0 (m, 2H), 7.53 (t, J = 7.6 Hz, 1H), 7.48-7.30 (m, 6H), 6.61 (s, 2H), 5.10 (s, 2H), 4.10-3.95 (m, 3H), 3.75-3.50 (m, 4H), 3.44 (bs, 4H), 2.90-2.75 (m, 1H), 2.63 (bs, 4H), 2.50-2.30 (m, 1H), 1.56-1.40 (m, 3H), 1.20-1.0 (m, 1H); Mass (m/z): 577.3 (M + H)$^+$; HPLC purity: 98.04%. |
| 21 | 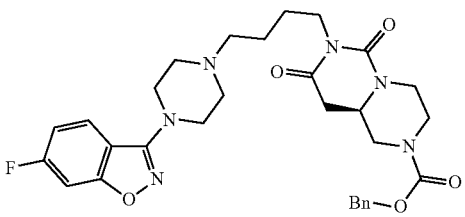 [SMILES: O=C(OCc1ccccc1)N1CCN2C(=O)N(CCCCN3CCN(c4noc5cc(F)ccc45)CC3)C(=O)C[C@@H]2C1]<br><br>7-{4-[4-(6-Fluoro-benzo[d]isoxazol-3-yl)-piperidin-1-yl]-butyl}-6,8-dioxo-octahydro-pyrazino[1,2-c]pyrimidine-2-carboxylic acid benzyl ester | $^1$H NMR (400 MHz, CDCl$_3$): δ 7.73-7.68 (m, 1H), 7.40-7.30 (m, 1H), 7.28-7.20 (m, 1H), 7.15-7.0 (m, 5H), 5.15 (s, 2H), 4.10-3.95 (m, 3H), 3.75-3.50 (m, 4H), 3.15-3.05 (m, 4H), 2.95-2.80 (m, 1H), 2.70-2.50 (m, 4H), 2.38-2.28 (m, 2H), 2.12-2.02 (m, 2H), 1.96-1.80 (m, 2H), 1.52-1.40 (m, 3H), 1.05-1.0 (m, 1H); Mass (m/z): 578.4 (M + H)$^+$. |

| Example Number | Chemical name and Structure | Characterization data |
|---|---|---|
| 22 | 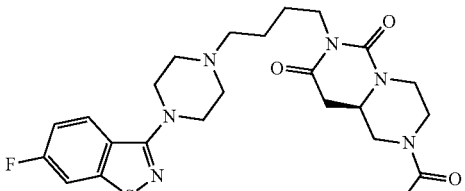<br>Fumarate<br>7-{4-[4-(6-Fluoro-benzo[d]isoxazol-3-yl)-piperidin-1-yl]-butyl}-6,8-dioxo-octahydro-pyrazino[1,2-c]pyrimidine-2-carboxylic acid benzyl ester fumarate | $^1$H NMR (400 MHz, DMSO-d$_6$): δ 8.06-7.98 (m, 1H), 7.70 (d, J = 8.4 Hz, 1H), 7.40-7.25 (m, 6H), 6.59 (s, 2H), 5.10 (s, 2H), 4.10-3.95 (m, 3H), 3.75-3.50 (m, 4H), 3.15-3.05 (m, 4H), 2.95-2.80 (m, 1H), 2.70-2.50 (m, 4H), 2.38-2.28 (m, 2H), 2.12-2.02 (m, 2H), 1.96-1.80 (m, 2H), 1.52-1.40 (m, 3H), 1.05-1.0 (m, 1H); Mass (m/z): 578.3 (M + H)$^+$; HPLC purity: 96.69%. |

Example-23: 2-[3-(4-benzo[d]isothiazol-3-yl-piperazin-1-yl)-propyl]tetrahydro-pyrrolo[1,2-c]pyrimidine-1,3-dione

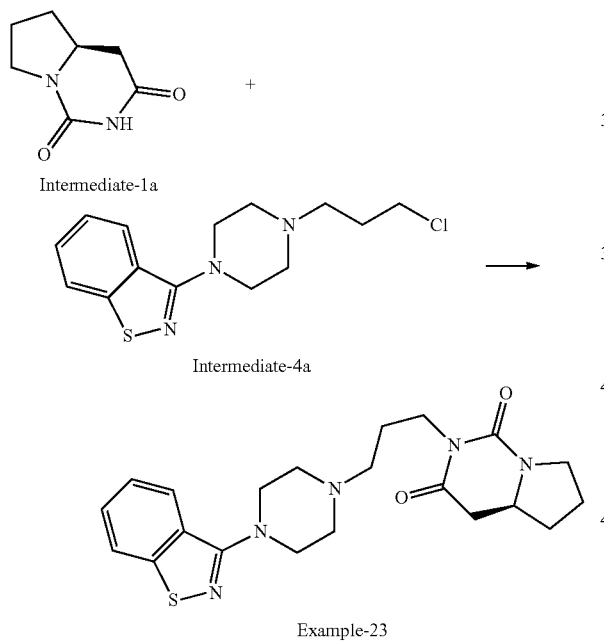

A mixture of intermediate-1a (1.54 g, 10.0 mmol), intermediate-4a (2.95 g, 10.0 mmol) and K$_2$CO$_3$ (2.76 g, 20.0 mol) in DMF (20 mL) was stirred at 80-100° C. for 16 h. The reaction mixture was cooled to r.t., poured into water (200 mL) and extracted with EtOAc. The organic phase was washed once with brine solution, dried over MgSO$_4$ and evaporated under vacuum. The residue was further purified by flash column chromatography which afforded above titled compound (2.12 g) in 52% yields. $^1$H NMR (400 MHZ, CDCl$_3$): δ 7.90 (d, J=8.4 Hz, 1H), 7.81 (d, J=8.0 Hz, 1H), 7.46 (t, J=7.2 Hz, 1H), 7.34 (t, J=7.6 Hz, 1H), 3.95-3.85 (m, 1H), 3.82-3.75 (m, 1H), 3.74-3.62 (m, 1H), 3.62-3.55 (m, 4H), 3.55-3.48 (m, 1H), 2.86 (dd, J=4.0, 16.0 Hz, 1H), 2.75-2.68 (m, 4H), 2.53 (t, J=7.6 Hz, 1H), 2.44 (dd, J=13.6, 16.0 Hz, 1H), 2.33-2.23 (m, 1H), 2.13-2.0 (m, 1H), 1.95-1.80 (m, 4H), 1.68-1.56 (m, 2H); Mass (m/z): 414.1 (M+H)$^+$.

Examples 24 and 25 were prepared using the procedure of example 23 using appropriate intermediates with some non-critical variations.

| Example Number | Chemical name and Structure | Characterization data |
|---|---|---|
| 24 | 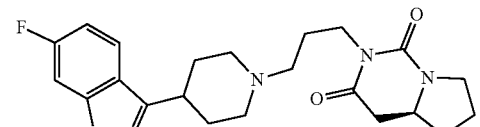<br>2-{3-[4-(6-Fluoro-benzo[d]isoxazol-3-yl)-piperidin-1-yl]-propyl}-tetrahydro-pyrrolo[1,2-c]pyrimidine-1,3-dione | $^1$H NMR (400 MHz, CDCl$_3$): δ 7.78-7.72 (m, 1H), 7.30-7.22 (m, 1H), 7.12-7.02 (m, 1H), 3.95-3.85 (m, 1H), 3.82-3.72 (m, 1H), 3.75-3.60 (m, 3H), 3.60-3.50 (m, 2H), 3.42-3.30 (m, 1H), 3.20-3.10 (m, 2H), 3.02-2.92 (m, 1H), 2.86 (dd, J = 3.6, 16.0 Hz, 1H), 2.62-2.50 (m, 2H), 2.44 (dd, J = 13.6, 16.0 Hz, 1H), 2.35-1.80 (m, 7H), 1.70-1.52 (m, 2H); Mass (m/z): 415.2 (M + H)$^+$. |

| Example Number | Chemical name and Structure | Characterization data |
| --- | --- | --- |
| 25 | 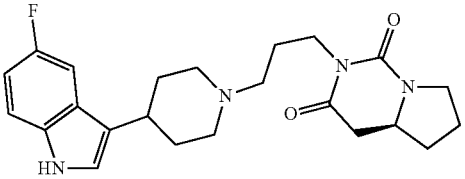 [SMILES: O=C1C[C@@H]2CCCN2C(=O)N1CCCN1CCC(c2c[nH]c3ccc(F)cc23)CC1]

2-{3-[4-(5-Fluoro-1H-indol-3-yl)-piperidin-1-yl]-propyl}-tetrahydro-pyrrolo[1,2-c]pyrimidine-1,3-dione | $^1$H NMR (400 MHz, CDCl$_3$): δ 8.18 (bs, 1H), 7.30-7.22 (m, 2H), 7.01 (s, 1H), 6.91 (t, J = 9.2 Hz, 1H), 3.93-3.83 (m, 1H), 3.80-3.75 (m, 1H), 3.75-3.68 (m, 1H), 3.68-3.60 (m, 2H), 3.58-3.48 (m, 1H), 3.20-3.12 (m, 2H), 2.86 (dd, J = 4.0, 16.0 Hz, 1H), 2.80-2.72 (m, 1H), 2.60-2.52 (m, 2H), 2.44 (dd, J = 13.6, 16.0 Hz, 1H), 2.33-2.18 (m, 3H), 2.13-1.98 (m, 3H), 1.95-1.82 (m, 3H), 1.66-1.53 (m, 2H); Mass (m/z): 413.2 (M + H)$^+$. |

Example-26: 2-[2-(4-Benzo[d]isothiazol-3-yl-piperazin-1-ylmethyl)-cyclohexylmethyl]-tetrahydro-pyrrolo[1,2-c]pyrimidine-1,3-dione

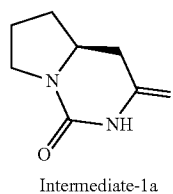

Intermediate-1a

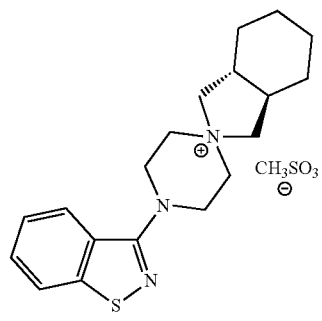

Intermediate-3a

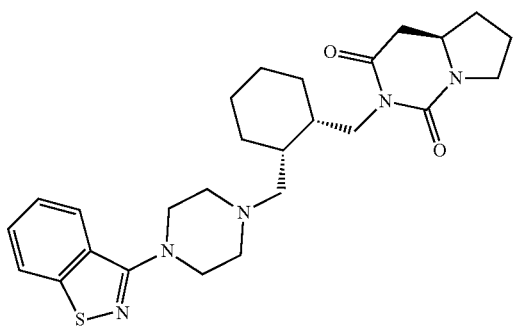

Example-26

A mixture of Intermediate-3a (114.0 g, 321.78 mmol), Intermediate-1a (45.1 g, 292.5 mmol), anhydrous K$_2$CO$_3$ (80.7 g, 585.0 mmol), and 18-crown-6 (0.77 g, 2.92 mmol) in xylene (1170 mL) was stirred and heated under reflux for 3 h. The hot mixture was filtered through filter cloth/paper; the filter cloth/paper was washed with EtOAc. The filtrate was washed with water and brine solution. The organic layer thus obtained was dried over anhydrous Na$_2$SO$_4$ and the solvent was removed under vacuum. The crude product was triturated with pentane followed by 3% EtOAc in hexane to obtain above titled compound (87.2 g) in 69.7% yield. $^1$H NMR (400 MHZ, CDCl$_3$): δ 7.91 (d, J=8.0 Hz, 1H), 7.80 (d, J=8.0 Hz, 1H), 7.45 (t, J=7.2 Hz, 1H), 7.34 (t, J=7.6 Hz, 1H), 4.15-4.0 (m, 1H), 3.80-3.60 (m, 4H), 3.58-3.48 (m, 5H), 2.88-2.76 (m, 1H), 2.70-2.56 (m, 4H), 2.45-2.33 (m, 1H), 2.32-2.20 (m, 2H), 2.15-2.02 (m, 1H), 1.98-1.83 (m, 2H), 1.70-1.48 (m, 5H), 1.45-1.35 (m, 1H), 1.30-0.95 (m, 4H); Mass (m/z): 482.2 (M+H)$^+$; HPLC purity: 92.01%.

Example-27: 2-[2-(4-Benzo[d]isothiazol-3-yl-piperazin-1-ylmethyl)-cyclohexylmethyl]-tetrahydro-pyrrolo[1,2-c]pyrimidine-1,3-dione oxalate

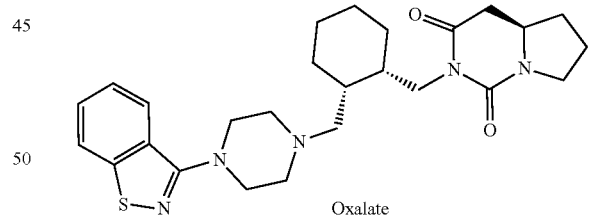

Oxalate

Example-27 was prepared from Example 26 by following the procedure as mentioned for Example-2 with non-critical variations. $^1$H NMR (400 MHZ, DMSO-d$_6$): δ 8.10 (d, J=6.8 Hz, 1H), 8.09 (d, J=7.2 Hz, 1H), 7.58 (t, J=7.2 Hz, 1H), 7.45 (t, J=8.0 Hz, 1H), 3.88-3.72 (m, 2H), 3.70-3.50 (m, 4H), 3.50-3.26 (m, 4H), 3.15-2.95 (m, 4H), 2.76-2.62 (m, 1H), 2.62-2.30 (m, 3H), 2.20-2.08 (m, 1H), 2.0-1.90 (m, 2H), 1.86-1.70 (m, 1H), 1.65-1.40 (m, 5H), 1.30-0.90 (m, 4H); Mass (m/z): 482.2 (M+H)$^+$; HPLC purity: 98.3%.

Examples 28-30 were prepared using the procedures of example 26 and example 2 using appropriate intermediates with some non-critical variations.

| Example Number | Chemical name and Structure | Characterization data |
|---|---|---|
| 28 | 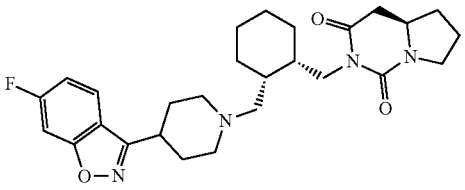<br>2-{2-[4-(6-Fluoro-benzo[d]isoxazol-3-yl)-piperidin-1-ylmethyl]-cyclohexylmethyl}-tetrahydro-pyrrolo[1,2-c]pyrimidine-1,3-dione | $^1$H NMR (400 MHz, CDCl$_3$): δ 7.75-7.63 (m, 1H), 7.30-7.20 (m, 1H), 7.10-7.0 (m, 1H), 4.16-3.97 (m, 1H), 3.80-3.60 (m, 3H), 3.60-3.50 (m, 2H), 3.13-2.95 (m, 3H), 2.90-2.80 (m, 2H), 2.65-2.52 (m, 1H), 2.48-2.35 (m, 2H), 2.32-2.25 (m, 1H), 2.23-2.0 (m, 7H), 1.98-1.85 (m, 2H), 1.70-1.50 (m, 2H), 1.40-1.0 (m, 6H); Mass (m/z): 483.3 (M + H)$^+$. |
| 29 | 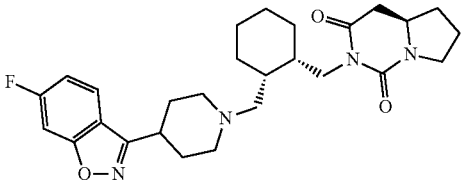 [SMILES: O=C1C[C@H]2CCCN2C(=O)N1C[C@H]1CCCC[C@H]1CN1CCC(c2noc3cc(F)ccc23)CC1]<br>Oxalate<br>2-{2-[4-(6-Fluoro-benzo[d]isoxazol-3-yl)-piperidin-1-ylmethyl]-cyclohexylmethyl}-tetrahydro-pyrrolo[1,2-c]pyrimidine-1,3-dione oxalate | $^1$H NMR (400 MHz, DMSO-d$_6$): δ 8.12-8.03 (m, 1H), 7.73 (d, J = 8.8 Hz, 1H), 7.34 (t, J = 8.8 Hz, 1H), 4.0-2.80 (m, 11H), 2.65-2.52 (m, 1H), 2.48-2.35 (m, 2H), 2.32-2.25 (m, 1H), 2.23-2.0 (m, 7H), 1.98-1.85 (m, 2H), 1.70-1.50 (m, 2H), 1.40-1.0 (m, 6H); Mass (m/z): 483.1 (M + H)$^+$; HPLC purity: 95.52%. |
| 30 | 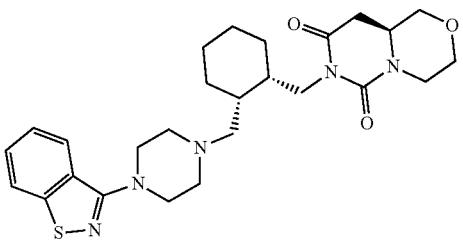 [SMILES: O=C1C[C@H]2COCCN2C(=O)N1C[C@H]1CCCC[C@H]1CN1CCN(c2nsc3ccccc23)CC1]<br>7-[2-(4-Benzo[d]isothiazol-3-yl-piperazin-1-ylmethyl)-cyclohexylmethyl]-tetrahydro-pyrimido[6,1-c][1,4]oxazine-6,8-dione | $^1$H NMR (400 MHz, CDCl$_3$): δ 7.91 (d, J = 8.2 Hz, 1H), 7.81 (d, J = 8.2 Hz, 1H), 7.45 (t, J = 7.5 Hz, 1H), 7.34 (t, J = 7.5 Hz, 1H), 7.75-7.63 (m, 1H), 4.25-4.10 (m, 1H), 4.10-4.0 (m, 2H), 4.0-3.90 (m, 2H), 3.60-3.40 (m, 5H), 3.20-3.10 (m, 1H), 3.08-2.97 (m, 1H), 2.70-2.58 (m, 4H), 2.45-2.35 (m, 1H), 2.30-2.10 (m, 1H), 1.98-1.88 (m, 2H), 1.70-1.50 (m, 4H), 1.20-1.0 (m, 2H), 0.90-0.80 (m, 4H); Mass (m/z): 498.2 (M + H)$^+$. |

Example-31: 7-[4-(4-Benzo[d]isothiazol-3-yl-piperazin-1-yl)-butyl]-hexahydro-pyrazino[1,2-c]pyrimidine-6,8-dione

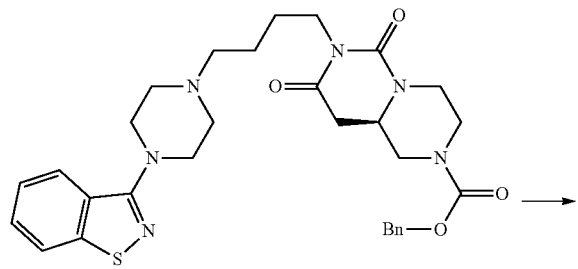

Example-19

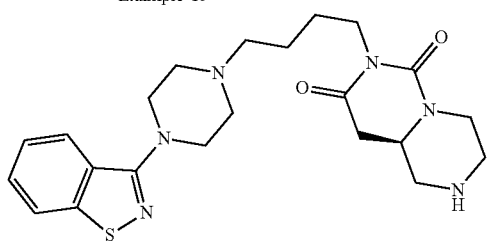

Example-31

To the stirred solution of Example-19 (300 mg, 0.52 mmol) in EtOAc (4.8 mL), Pd—C(10%, 60 mg) was added. The reaction mass was degassed with nitrogen followed by hydrogen. A balloon filled with hydrogen was fixed on the reaction flask using two way adapter to keep positive hydrogen pressure in the reaction. The reaction mass was continued until the starting material was completely consumed. The hydrogen atmosphere was removed, the reaction mass was purged with nitrogen gas, filtered through a pad of filter cloth/paper to remove the catalyst. The filtrate was evaporated to dryness to obtain a crude mass which was triturated with several portions of hexane to obtain the titled compound (235 mg) in quantitative yields. $^1$H NMR (400 MHZ, CDCl$_3$): δ 7.91 (d, J=8.0 Hz, 1H), 7.81 (d, J=8.0 Hz, 1H), 7.46 (t, J=8.0 Hz, 1H), 7.37 (t, J=7.6 Hz, 1H), 4.20-3.90 (m, 3H), 3.90-3.72 (m, 1H), 3.60-3.55 (m, 4H), 3.52-3.42 (m, 1H), 3.08-2.86 (m, 2H), 2.80-2.68 (m, 4H), 2.68-2.62 (m, 4H), 2.52-2.40 (m, 2H), 1.63-1.52 (m, 4H); Mass (m/z): 443.3 (M+H)$^+$.

Example-32: 7-{4-[4-(6-Fluoro-benzo[d]isoxazol-3-yl)-piperidin-1-yl]-butyl}-hexahydro-pyrazino[1,2-c]pyrimidine-6,8-dione

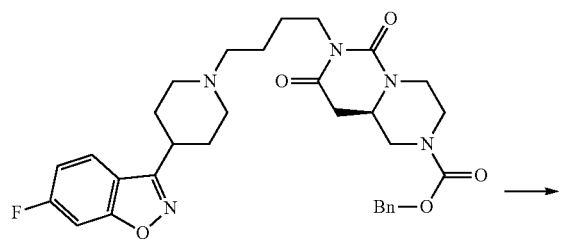

Example-21

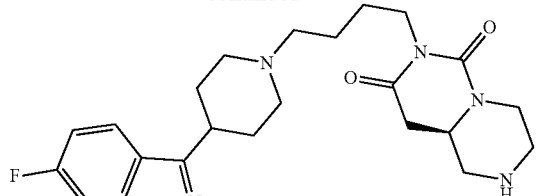

Example-32

Example-32 was prepared from Example 21 using the procedures of Example 31 with non-critical variations.
$^1$H NMR (400 MHZ, CDCl$_3$): δ 8.10-8.02 (m, 1H), 7.73 (d, J=9.2 Hz, 1H), 7.36 (dd, J=8.0, 9.2 Hz, 1H), 4.25-4.15 (m, 2H), 4.15-3.95 (m, 3H), 3.95-3.75 (m, 2H), 3.60-3.50 (m, 2H), 3.10-2.90 (m, 5H), 2.86-2.77 (m, 1H), 2.77-2.65 (m, 1H), 2.60-2.50 (m, 1H), 2.25-2.05 (m, 3H), 1.97-1.80 (m, 2H), 1.80-1.68 (m, 4H); Mass (m/z): 444.4 (M+H)$^+$.

Example-33: 7-[4-(4-Benzo[d]isothiazol-3-yl-piperazin-1-yl)-butyl]-6,8-dioxo-octahydro-pyrazino[1,2-c]pyrimidine-2-carboxylic acid methyl ester

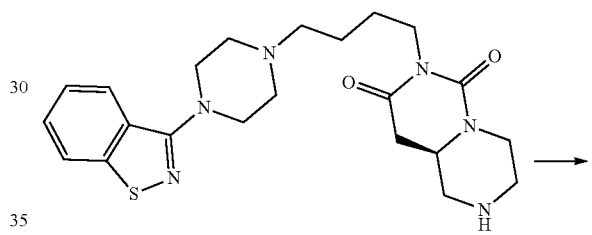

Example-31

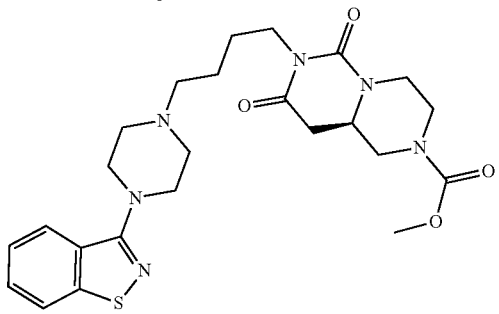

Example-33

To the stirred solution of Example-31 (50.0 mg, 0.11 mmol) in DCM (1.0 mL) cooled at 0° C., triethylamine (0.03 mL, 0.22 mmol) followed by methylchloroformate (0.02 mL, 0.2 mmol) was added. The reaction mixture was stirred for additional 1 h at same temperature after which, quenched by addition of aqueous NaHCO$_3$ solution. The reaction mass was extracted with EtOAc, the combined organic layer was washed with brine solution, dried over anhydrous Na$_2$SO$_4$ and the solvent was removed under vacuum to obtain the crude mass which was purified by silica gel column chromatography which afforded above titled compound (50 mg) in 90% yield. $^1$H NMR (400 MHZ, CDCl$_3$): δ 7.89 (d, J=8.0 Hz, 1H), 7.82 (d, J=8.0 Hz, 1H), 7.49 (t, J=7.6 Hz, 1H), 7.38 (d, J=7.6 Hz, 1H), 4.30-4.10 (m, 3H), 3.95-3.45 (m, 11H), 3.10-2.88 (m, 3H), 2.85-2.60 (m, 5H), 2.60-2.40 (m, 2H), 1.70-1.55 (m, 2H), 1.38-1.20 (m, 2H); Mass (m/z): 501.3 (M+H)$^+$; HPLC purity: 91.61%.

Example-34:7-[4-(4-Benzo[d]isothiazol-3-yl-piperazin-1-yl)-butyl]-6,8-dioxo-octahydro-pyrazino[1,2-c]pyrimidine-2-carboxylic acid methyl ester fumarate

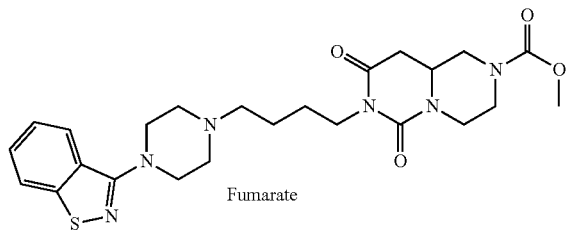 [SMILES: COC(=O)N1CCN2C(=O)N(CCCCN3CCN(c4nsc5ccccc45)CC3)C(=O)CC2C1]

Fumarate

The Example-33 was converted to its fumarate salt by treatment with fumaric acid in isopropanol to obtain above titled compound. $^1$H NMR (400 MHZ, DMSO-$d_6$): δ 8.07 (d, J=8.4 Hz, 2H), 7.58 (d, J=7.6 Hz, 1H), 7.46 (t, J=7.6 Hz, 1H), 6.62 (s, 2H), 4.05-3.93 (m, 3H), 3.95-3.45 (m, 10H), 3.10-2.88 (m, 2H), 2.85-2.60 (m, 5H), 2.60-2.40 (m, 2H), 1.70-1.55 (m, 4H), 1.35-1.22 (m, 2H); Mass (m/z): 501.3 (M+H)$^+$; HPLC purity: 92.01%.

Examples 35-38 were prepared by following the procedures as reported for examples 33 and 34 with some non-critical variations.

| Example Number | Chemical name and Structure | Characterization data |
|---|---|---|
| 35 | 7-{4-[4-(6-Fluoro-benzo[d]isoxazol-3-yl)-piperidin-1-yl]-butyl}-6,8-dioxo-octahydro-pyrazino[1,2-c]pyrimidine-2-carboxylic acid methyl ester | $^1$H NMR (400 MHz, CDCl$_3$): δ 8.10-8.02 (m, 1H), 7.73 (d, J = 9.2 Hz, 1H), 7.36 (dd, J = 8.0, 9.2 Hz, 1H), 4.30-4.10 (m, 5H), 3.95-3.75 (m, 2H), 3.73 (s, 3H), 3.60-3.50 (m, 2H), 3.10-2.90 (m, 5H), 2.86-2.77 (m, 1H), 2.77-2.65 (m, 1H), 2.60-2.50 (m, 1H), 2.25-2.05 (m, 3H), 1.97-1.80 (m, 2H), 1.80-1.68 (m, 4H); Mass (m/z): 502.3 (M + H)$^+$; |
| 36 | 7-{4-[4-(6-Fluoro-benzo[d]isoxazol-3-yl)-piperidin-1-yl]-butyl}-6,8-dioxo-octahydro-pyrazino[1,2-c]pyrimidine-2-carboxylic acid methyl ester fumarate | $^1$H NMR (400 MHz, DMSO-$d_6$): δ 12.7 (bs, 2H), 8.10-8.02 (m, 1H), 7.73 (d, J = 9.2 Hz, 1H), 7.36 (dd, J = 8.0, 9.2 Hz, 1H), 4.30-4.10 (m, 5H), 3.95-3.75 (m, 2H), 3.73 (s, 3H), 3.60-3.50 (m, 2H), 3.10-2.90 (m, 5H), 2.86-2.77 (m, 1H), 2.77-2.65 (m, 1H), 2.60-2.50 (m, 1H), 2.25-2.05 (m, 3H), 1.97-1.80 (m, 2H), 1.70-1.58 (m, 2H), 1.55-1.47 (m, 2H); Mass (m/z): 502.3 (M + H)$^+$; HPLC purity: 98.76% |
| 37 | 2-Acetyl-7-[4-(4-benzo[d]isothiazol-3-yl-piperazin-1-yl)-butyl]-hexahydro-pyrazino[1,2-c]pyrimidine-6,8-dione | $^1$H NMR (400 MHz, CDCl$_3$): δ 7.88 (d, J = 8.0 Hz, 1H), 7.83 (d, J = 8.0 Hz, 1H), 7.49 (t, J = 7.6 Hz, 1H), 7.38 (t, J = 7.6 Hz, 1H), 4.70-4.58 (m, 1H), 4.30-4.20 (m, 1H), 4.10-4.0 (m, 3H), 3.90-3.72 (m, 1H), 3.60-3.55 (m, 4H), 3.52-3.42 (m, 1H), 3.08-2.86 (m, 2H), 2.80-2.68 (m, 2H), 2.68-2.62 (m, 4H), 2.52-2.40 (m, 2H), 2.14 (s, 3H), 1.71-1.51 (m, 4H); Mass (m/z): 485.3 (M + H)$^+$. |

| Example Number | Chemical name and Structure | Characterization data |
|---|---|---|
| 38 | 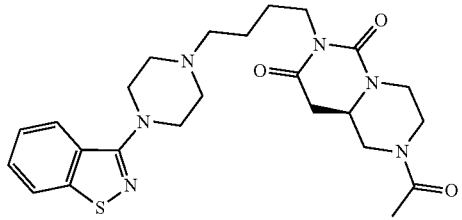 [SMILES: CC(=O)N1CCN2C(=O)N(CCCCN3CCN(c4nsc5ccccc45)CC3)C(=O)C[C@@H]2C1]<br>Fumarate<br><br>2-Acetyl-7-[4-(4-benzo[d]isothiazol-3-yl-piperazin-1-yl)-butyl]-hexahydro-pyrazino[1,2-c]pyrimidine-6,8-dione fumarate | $^1$H NMR (400 MHz, DMSO-$d_6$): δ 8.08 (d, J = 8.4 Hz, 2H), 7.57 (t, J = 8.0 Hz, 1H), 7.46 (t, J = 7.6 Hz, 1H), 6.62 (s, 2H), 4.45-4.30 (m, 1H), 4.02-3.85 (m, 4H), 3.80-3.72 (m, 1H), 3.60-3.55 (m, 4H), 3.52-3.42 (m, 1H), 3.08-2.86 (m, 2H), 2.80-2.68 (m, 2H), 2.68-2.62 (m, 4H), 2.52-2.40 (m, 2H), 2.02 (s, 3H), 1.76-1.52 (m, 4H); Mass (m/z): 485.3 (M + H)$^+$. |

Example-39: 7-[4-(4-Benzo[d]isothiazol-3-yl-piperazin-1-yl)-butyl]-2-isopropyl-hexahydro-pyrazino[1,2-c]pyrimidine-6,8-dione

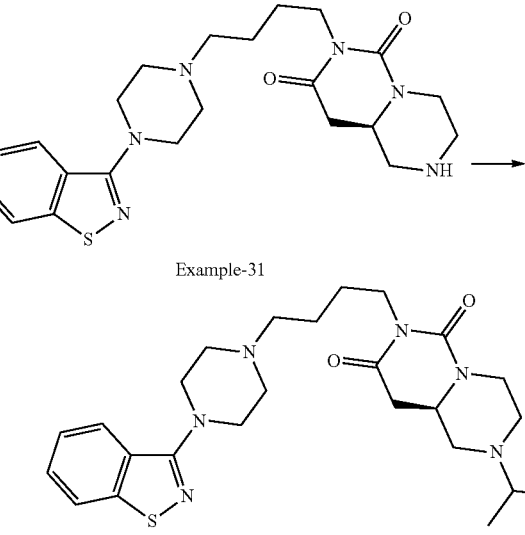

To the stirred solution of Example-31 (44.0 mg, 0.1 mmol) in DCM (1.0 mL) cooled at 0° C., K$_2$CO$_3$ (28.0 mg, 0.2 mmol) followed by 2-iodopropane (26.0 mg, 0.15 mmol) was added. The reaction mixture was gradually warmed to r.t., and stirred for additional 1 h after which, quenched by addition of aqueous NaHCO$_3$ solution. The reaction mass was extracted with EtOAc, the combined organic layer was washed with brine solution, dried over anhydrous Na$_2$SO$_4$ and the solvent was removed under vacuum to obtain the crude mass which was purified by silica gel column chromatography which afforded above titled compound (38 mg) in 82% yield. $^1$H NMR (400 MHZ, CDCl$_3$): δ 7.91 (d, J=8.0 Hz, 1H), 7.81 (d, J=8.0 Hz, 1H), 7.46 (t, J=8.0 Hz, 1H), 7.37 (t, J=7.6 Hz, 1H), 4.20-3.90 (m, 3H), 3.90-3.72 (m, 4H), 3.60-3.55 (m, 4H), 3.52-3.42 (m, 1H), 3.08-2.86 (m, 2H), 2.80-2.68 (m, 2H), 2.68-2.62 (m, 4H), 2.52-2.40 (m, 2H), 1.73-1.54 (m, 4H), 1.05 (d, J=6.4 Hz, 6H); Mass (m/z): 485.5 (M+H)$^+$.

Example-40: 7-[4-(4-Benzo[d]isothiazol-3-yl-piperazin-1-yl)-butyl]-2-isopropyl-hexahydro-pyrazino[1,2-c]pyrimidine-6,8-dione fumarate The Example-39 was converted to its fumarate salt by treatment with fumaric acid in isopropanol to obtain above titled compound. $^1$H NMR (400 MHZ, DMSO-$d_6$): δ 8.06 (d, J=8.4 Hz, 2H), 7.57 (t, J=7.2 Hz, 1H), 7.45 (t, J=7.6 Hz, 1H), 6.62 (s, 2H), 4.10-3.90 (m, 3H), 3.90-3.72 (m, 2H), 3.60-3.55 (m, 4H), 3.52-3.42 (m, 1H), 3.08-2.86 (m, 2H), 2.80-2.68 (m, 2H), 2.68-2.62 (m, 4H), 2.52-2.40 (m, 2H), 1.77-1.53 (m, 4H), 1.04 (d, J=6.0 Hz, 6H); Mass (m/z): 485.4 (M+H)$^+$.

The following examples 41 and 42 were prepared by using the procedure as described for examples-1 and examples-2 preparations respectively using appropriate intermediates with some non-critical variations, and examples 43 and 44 were prepared using the procedure of example 23 and examples-2 preparations respectively using appropriate intermediates with some non-critical variations.

| Example Number | Chemical name and Structure | Characterization data |
|---|---|---|
| 41 | 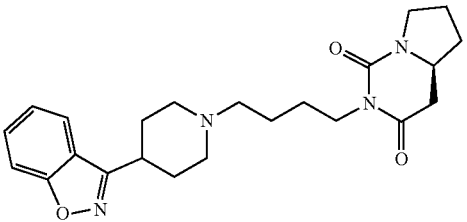<br>2-{4-[4-(Benzo[d]isoxazol-3-yl)-piperidin-1-yl]-butyl}-tetrahydro-pyrrolo[1,2-c]pyrimidine-1,3-dione | $^1$H NMR (400 MHz, CDCl$_3$): δ 7.78 (d, J = 8.0 Hz, 1H), 7.56 (d, J = 8.4 Hz, 1H), 7.54 (t, J = 7.2 Hz, 1H), 7.29 (t, J = 7.2 Hz, 1H), 3.88-3.78 (m, 1H), 3.78-3.60 (m, 3H), 3.58-3.48 (m, 1H), 3.15-3.02 (m, 3H), 2.88-2.80 (m, 1H), 2.45-2.38 (m, 3H), 2.32-2.23 (m, 1H), 2.18-2.02 (m, 7H), 1.95-1.81 (m, 1H), 1.67-1.52 (m, 5H); Mass (m/z): 411.1 (M + H)$^+$. |
| 42 | 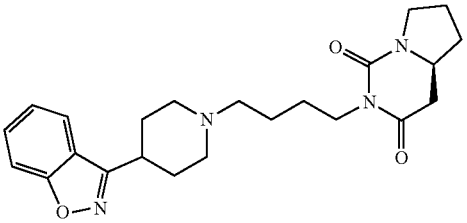 [SMILES: O=C1C[C@@H]2CCCN2C(=O)N1CCCCN1CCC(c2noc3ccccc23)CC1]<br>Oxalate<br>2-{4-[4-(Benzo[d]isoxazol-3-yl)-piperidin-1-yl]-butyl}-tetrahydro-pyrrolo[1,2-c]pyrimidine-1,3-dione, oxalate | $^1$H NMR (400 MHz, DMSO-d$_6$): δ 8.02 (d, J = 8.0 Hz, 1H), 7.75 (d, J = 8.4 Hz, 1H), 7.68 (t, J = 7.2 Hz, 1H), 7.43 (t, J = 7.6 Hz, 1H), 3.74-3.63 (m, 2H), 3.63-3.55 (m, 1H), 3.54-3.42 (m, 4H), 3.42-3.32 (m, 1H), 3.08-2.94 (m, 4H), 2.76-2.67 (m, 1H), 2.61-2.55 (m, 1H), 2.29-2.20 (m, 2H), 2.19-2.05 (m, 3H), 2.0-1.90 (m, 1H), 1.85-1.71 (m, 1H), 1.69-1.45 (m, 5H); Mass (m/z): 411.0 (M + H)$^+$; HPLC purity: 98.79%. |
| 43 | 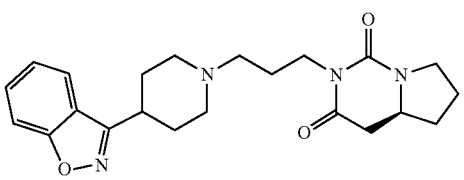 [SMILES: O=C1C[C@@H]2CCCN2C(=O)N1CCCN1CCC(c2noc3ccccc23)CC1]<br>2-[3-(4-Benzo[d]isoxazol-3-yl-piperidin-1-yl)-propyl]-tetrahydro-pyrrolo[1,2-c]pyrimidine-1,3-dione | $^1$H NMR (400 MHz, CDCl$_3$): δ 7.77 (d, J = 7.6 Hz, 1H), 7.56 (d, J = 8.0 Hz, 1H), 7.52 (t, J = 8.4 Hz, 1H), 7.29 (t, J = 6.8 Hz, 1H), 3.93-3.83 (m, 1H), 3.80-3.70 (m, 1H), 3.70-3.60 (m, 2H), 3.58-3.48 (m, 1H), 3.13-3.03 (m, 3H), 2.88-2.80 (m, 1H), 2.50-2.42 (m, 2H), 2.42-2.36 (m, 1H), 2.32-2.22 (m, 1H), 2.18-2.02 (m, 5H), 1.95-1.75 (m, 2H), 1.67-1.52 (m, 4H); Mass (m/z): 397.1 (M + H)$^+$; HPLC purity: 91.91%. |
| 44 | 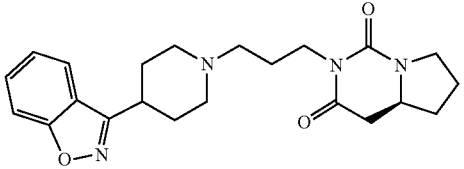<br>Oxalate<br>2-[3-(4-Benzo[d]isoxazol-3-yl-piperidin-1-yl)-propyl]-tetrahydro-pyrrolo[1,2-c]pyrimidine-1,3-dione, oxalate | $^1$H NMR (400 MHz, DMSO-d$_6$): δ 8.0 (d, J = 7.6 Hz, 1H), 7.75 (d, J = 8.4 Hz, 1H), 7.68 (t, J = 7.2 Hz, 1H), 7.43 (t, J = 6.8 Hz, 1H), 3.80-3.30 (m, 9H), 3.08-2.94 (m, 3H), 2.78-2.65 (m, 1H), 2.63-2.45 (m, 1H), 2.28-2.02 (m, 5H), 2.02-1.92 (m, 1H), 1.90-1.73 (m, 3H), 1.60-1.50 (m, 1H); Mass (m/z): 397.0 (M + H)$^+$; HPLC purity: 97.48%. |

Example-45: Determination of In Vitro Binding Potency at Multiple Receptors i) Determination of $K_i$ at 5-$HT_{1A}$ Receptor Compounds were tested according to the following procedure.

Materials and Method

Receptor source: Recombinant mammalian cells (HEK293-EBNA)
Radioligand: [$^3$H]-8-Hydroxy DPAT (200 Ci/mmol)
Final ligand concentration: 0.8 nM
Non-specific determinant: 0.1 mM U92016A
Reference compound: U92016A
Positive control: U92016A Incubation Conditions:

Reactions were carried out in buffer with pH 7.4 containing 50 mM Tris-HCl, 0.5 mM EDTA, 10 mM $MgSO_4$, 0.1% Ascorbic acid for 2 h at r.t. The reaction was terminated by rapid vacuum filtration onto the glass fiber filters. Radioactivity trapped onto the filters was determined and compared to the control values in order to ascertain any interactions of the test compound(s) with cloned human 5-$HT_{1A}$ receptor binding site.

Reference: *British Journal of Pharmacology*, 2000, 130, 1108-1114.

ii) Determination of $K_i$ at 5-$HT_{2A}$ Receptor

Compounds were tested according to the following procedure.

Materials and Method

Receptor source: Recombinant mammalian cells (CHO-$K_1$)
Radioligand: [$^3$H]-Ketanserine (41.9 Ci/mmol)
Final ligand concentration: 1.25 nM
Non-specific determinant: 0.1 mM 1-Napthyl piperazine (1-NP)
Reference compound: 1-Napthyl piperazine (1-NP)
Positive control: 1-Napthyl piperazine (1-NP)

Incubation Conditions:

Reactions were carried out in buffer with pH 7.4 containing 50 mM Tris-HCl, 4 mM $CaCl_2$), 0.1% Ascorbic acid for 1 h at r.t. The reaction was terminated by rapid vacuum filtration onto the glass fiber filters. Radioactivity trapped onto the filters was determined and compared to the control values in order to ascertain any interactions of the test compound(s) with cloned human 5-$HT_{2A}$ receptor binding site.

Reference: *J Biomol Screen*, 2000, 5 (4), 269-278.

iii) Determination of $K_i$ at SERT Receptor

Compounds were tested according to the following procedure.

Materials and Method

Receptor source: Recombinant mammalian cells (HEK293)
Radioligand: [$^3$H]-Citalopram (80.8 Ci/mmol)
Final ligand concentration: 2 nM
Non-specific determinant: 0.1 mM Venlafaxine
Reference compound: Venlafaxine
Positive control: Venlafaxine Incubation Conditions:

Reactions were carried out in buffer with pH 7.4 containing 50 mM Tris-HCl, 150 mM NaCl, 5 mM KCl and scintillation proximity assay (SPA) beads (0.1 mg/well) for 3 h at r.t. Radioactivity proximal to SPA beads was determined by scintillation proximity assay and compared to the control values in order to ascertain any interactions of the test compound(s) with cloned human SERT receptor binding site.

Reference: *Journal of Pharmacology and Experimental Therapeutics*, 1987, 242 (1), 364-371.

iv) Determination of $K_i$ at $D_{2S}$ Receptor

Compounds were tested according to the following procedure.

Materials and Method

Receptor source: Recombinant mammalian cells (CHO-K1)
Radioligand: [$^3$H]-Raclopride (80.8 Ci/mmol)
Final ligand concentration: 4 nM
Non-specific determinant: 0.1 mM Haloperidol
Reference compound: Haloperidol
Positive control: Haloperidol Incubation Conditions:

Reactions were carried out in buffer with pH 7.4 containing 50 mM Tris-HCl, 120 mM NaCl, 5 mM KCl, 5 mM $MgCl_2$, 1 mM EDTA for 2 h at r.t. The reaction was terminated by rapid vacuum filtration onto the glass fiber filters. Radioactivity trapped onto the filters was determined and compared to the control values in order to ascertain any interactions of the test compound(s) with cloned human dopamine Das receptor binding site.

Reference: *Neuropsychopharmacology*, 2010, 35, 806-817.

TABLE 1

$K_i$ (nM) values of the test compounds at h5-$HT_{1A}$, h5-$HT_{2A}$, hSERT and h$D_{2S}$.

| Example No | h5-$HT_{1A}$ | h5-$HT_{2A}$ | hSERT | h$D_{2S}$ |
|---|---|---|---|---|
| 2 | 0.06 | 0.6 | 1061 | 5.4 |
| 4 | 0.195 | 4.24 | 227.9 | 1.83 |
| 5 | 14.70 | 0.70 | >10 μM | 7.30 |
| 7 | 1.80 | 49.90 | 38.5 | 4.50 |
| 9 | 0.89 | 2.49 | 833.2 | 2.78 |
| 11 | 0.29 | 1.02 | 1281 | 0.62 |
| 12 | 0.1 | 0.6 | 181 | 0.6 |
| 13 | 14.9 | 2.5 | 1632.0 | 2.5 |
| 15 | 2.2 | 53.6 | 26.9 | 2.9 |
| 16 | 0.6 | 1208.0 | 426.7 | 59.1 |
| 18 | 0.8 | 4.2 | 1743.0 | 6.5 |
| 19 | 1.1 | 0.8 | 126.4 | 3.2 |
| 20 | 1.3 | 1.1 | 147.7 | 2.7 |
| 21 | 46.6 | 0.9 | 165.9 | 1.8 |
| 22 | 84.1 | 1.5 | 278.6 | 2.5 |
| 23 | 21.4 | 5.3 | 918.0 | 22.3 |
| 24 | 1693.0 | 7.1 | >10 μM | 103.0 |
| 25 | 58.6 | 194.6 | 297.9 | 23.8 |
| 27 | 4.7 | 2.0 | >10 μM | 0.2 |
| 29 | 10.0 | 0.8 | >10 μM | 0.2 |
| 30 | NA | 8.5 | 9351.0 | 0.6 |
| 33 | 0.3 | 0.8 | 61.1 | 1.7 |
| 34 | 1.3 | 0.5 | 152.4 | 2.4 |
| 35 | 45.7 | 4.8 | 975.0 | 4.7 |
| 36 | 130.0 | 2.2 | 1480.0 | 3.3 |
| 37 | 0.3 | 1.5 | 1096.0 | 8.2 |
| 38 | 0.3 | 2.2 | 953.0 | 4.5 |
| 40 | 0.5 | 1.6 | 1250.0 | 5.0 |
| 42 | 8.7 | 11.6 | >10 μM | 37.3 |
| 44 | 530.9 | 59.9 | >10 μM | 119.2 |

Example-46: In Vitro Functional Activity a) Determination of $K_b$ Values at 5-HT$_{2A}$ Receptor:

A stable CHO cell line expressing recombinant human 5-HT$_{2A}$ receptor and pCRE-Luc reporter system was used for cell-based assay. The assay offers a non-radioactive based approach to determine binding of a compound to GPCRs. In this specific assay, the level of intracellular cAMP which is modulated by activation or inhibition of the receptor was measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compound were added along with 1 µM of serotonin in Opti-MEM medium to the cells. The incubation was continued at 37° C. in $CO_2$ incubator for 4 hours. Medium was removed and cells were washed with phosphate buffered saline. The cells were lysed and luciferase activity was measured in a Luminometer. Luminescence units were plotted against the compound concentrations using GraphPad Prism software. $EC_{50}$ values of the compounds were defined as the concentration required in reducing the luciferase activity by 50%. The $K_b$ values were calculated by feeding the concentration of agonist used in the assay and its $EC_{50}$ value in the same software.

References: *Scientific Reports*. 2015, 5, 8060 and *Journal of biological chemistry*, 2002, 277, 11441-11449.

Results: Example-2 exhibited antagonistic activity in pCRE-Luc based reporter gene assay on human recombinant 5-HT$_{2A}$ receptor with no detectable agonist activity. The $K_b$ value is tabulated below.

TABLE 2

| Example No. | $K_b$ (nM) |
|---|---|
| 2 | 8 | b) Determination of $K_b$ Values at $D_{2S}$ Receptor:

A stable CHO cell line expressing recombinant human Das receptor and pCRE-Luc reporter system was used for cell-based assay. The assay offers a non-radioactive based approach to determine binding of a compound to GPCRs. In this specific assay, the level of intracellular cAMP which is modulated by activation or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compound were added along with 0.3 µM of Dopamine and 1 µM of forskolin in Opti-MEM medium to the cells. The incubation was continued at 37° C. in $CO_2$ incubator for 4 hours. Medium was removed and cells were washed with phosphate buffered saline. The cells were lysed and luciferase activity was measured in a Luminometer. Luminescence units were plotted against the compound concentrations using GraphPad Prism software. $EC_{50}$ values of the compounds were defined as the concentration required in reducing the luciferase activity by 50%. The $K_b$ values were calculated by feeding the concentration of agonist used in the assay and its $EC_{50}$ value in the same software.

References: *European Journal of Pharmacology*, 2005, 515, 10-19.

Results: Example-2 and 4 exhibited antagonistic activity in pCRE-Luc based reporter gene assay on human recombinant $D_{2S}$ receptor with no detectable agonist activity. The Kb value is tabulated below.

TABLE 3

| Example No. | $K_b$ (nM) |
|---|---|
| 2 | 33 |
| 4 | 54.4 | c) Determination of $K_b$ Values at 5-HT$_{1A}$ Receptor:

A stable CHO cell line expressing recombinant human 5-HT$_{1A}$ receptor and pCRE-Luc reporter system was used for cell-based assay. The assay offers a non-radioactive based approach to determine binding of a compound to GPCRs. In this specific assay, the level of intracellular cAMP which is modulated by activation or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compound were added along with 1 µM of U92016A and 1 µM of forskolin in Opti-MEM medium to the cells. The incubation was continued at 37° C. in $CO_2$ incubator for 4 hours. Medium was removed and cells were washed with phosphate buffered saline. The cells were lysed and luciferase activity was measured in a Luminometer. Luminescence units were plotted against the compound concentrations using GraphPad Prism software. $EC_{50}$ values of the compounds were defined as the concentration required in reducing the luciferase activity by 50%. The $K_b$ values were calculated by feeding the concentration of agonist used in the assay and its $EC_{50}$ value in the same software.

References: *Scientific Reports*, 2015, 5, 8060 and *Journal of biological chemistry*, 1990, 265, 5825-5832.

Results: Example-2 exhibited antagonistic activity in pCRE-Luc based reporter gene assay on human recombinant 5-HT$_{1A}$ receptor with no detectable agonist activity. The $K_b$ value is tabulated below.

TABLE 4

| Example No. | $K_b$ (nM) |
|---|---|
| 2 | 2.3 | d) Determination of $K_b$ Values at 5-HT$_7$ Receptor:

A stable CHO cell line expressing recombinant rat 5-HT$_7$ receptor and pCRE-Luc reporter system was used for cell-based assay. The assay offers a non-radioactive based approach to determine binding of a compound to GPCRs. In this specific assay, the level of intracellular cAMP which is modulated by activation or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compound were added along with 1

μM of serotonin in Opti-MEM medium to the cells. The incubation was continued at 37° C. in $CO_2$ incubator for 4 hours. Medium was removed and cells were washed with phosphate buffered saline. The cells were lysed and luciferase activity was measured in a Luminometer. Luminescence units were plotted against the compound concentrations using GraphPad Prism software. $EC_{50}$ values of the compounds were defined as the concentration required in reducing the luciferase activity by 50%. The $K_b$ values were calculated by feeding the concentration of agonist used in the assay and its $EC_{50}$ value in the same software.

References: *Scientific Reports,* 2015, 5, 8060, *British Journal of Pharmacology,* 2004, 143, 404-410, and *Bioorganic & Medicinal Chemistry Letters,* 2004, 14, 4245-4248.

Results: Example-2, 9, 11 and 18 exhibited antagonistic activity in pCRE-Luc based reporter gene assay on rat recombinant 5-$HT_7$ receptor with no detectable agonist activity. The $K_b$ values are tabulated below.

TABLE 5

| Example No. | $K_b$ (nM) |
|---|---|
| 2 | 0.6 |
| 9 | 0.7 |
| 11 | 0.17 |
| 18 | 1.0 | lar vein catheter. Rats were randomly divided for oral (3 mg/kg) and intravenous (1 mg/kg) dosing (n=3/group) and fasted overnight before oral dosing (p.o.). However, food and water were provided ad libitum to the rats allocated for intravenous dosing.

At pre-determined time points, blood samples were collected through jugular vein and replenished with an equivalent volume of normal saline. Collected blood was transferred into a labeled eppendorf tube containing 10 μL of heparin as an anticoagulant. Typically blood samples were collected at 0.08, 0.25, 0.5, 1, 2, 4, 6, 8, and 24 h post dose. Blood samples were centrifuged at 4000 rpm for 10 min. Plasma was separated and stored frozen at −80° C. until analysis. The concentrations of the test compounds were quantified in plasma by qualified LC-MS/MS method using suitable extraction technique. The test compounds were quantified in the calibration range around 1-1000 ng/mL in plasma. Study samples were analyzed using calibration samples in the batch and quality control samples spread across the batch.

Pharmacokinetic parameters $C_{max}$, $AUC_t$, $t_{1/2}$. Clearance and Bioavailability (F) were calculated using standard non-compartmental model by using Phoenix WinNonlin 6.0.4 version software package.

TABLE 6

Pharmacokinetic profile of the test compounds*

| Example No. | ROA | $C_{max}$ (ng/mL) | $AUC_{0-t}$ (ng · hr/mL) | $t_{1/2}$ (hr) | Clearance (mL/min/kg) | F (%) |
|---|---|---|---|---|---|---|
| 2 | oral (gavage) | 253 ± 59 | 244 ± 53 | 1.3 ± 0.1 | — | 15 ± 3 |
|   | intravenous (bolus) | — | 544 ± 19 | 2.0 ± 0.7 | 30 ± 1 | |
| 4 | oral (gavage) | 77 ± 2 | 169 ± 14 | 1.1 ± 0.3 | — | 16 ± 1 |
|   | intravenous (bolus) | — | 350 ± 40 | 0.8 ± 0.2 | 48 ± 5 | |
| 5 | oral (gavage) | 152 ± 44 | 151 ± 61 | 0.7 ± 0.1 | — | 22 ± 9 |
|   | intravenous (bolus) | — | 226 ± 11 | 0.5 ± 0.1 | 74 ± 3.4 | |
| 9 | oral (gavage) | 164 ± 43 | 178 ± 23 | 1.4 ± 0.3 | — | 14 ± 2 |
|   | intravenous (bolus) | — | 415 ± 69 | 1.8 ± 0.1 | 40 ± 6 | |
| 11 | oral (gavage) | 94 ± 52 | 98 ± 63 | 2.0 ± 0.2 | — | 8 ± 5 |
|   | intravenous (bolus) | — | 412 ± 44 | 1.3 ± 0.1 | 41 ± 5 | |
| 27 | oral (gavage) | 186 ± 109 | 173 ± 92 | 1.8 ± 0.1 | — | 16 ± 8 |
|   | intravenous (bolus) | — | 360 ± 10 | 2.4 ± 0.4 | 45 ± 1.3 | |
| 29 | oral (gavage) | 37 ± 14 | 40 ± 15 | 0.9 ± 0.1 | — | 4.6 ± 2 |
|   | intravenous (bolus) | — | 291 ± 17 | 1.0 ± 0.1 | 57 ± 3 | |

*Fasted male Wistar rats were used; Vehicle used is water for injection for both oral and i.v. routes. Values are mean ± S.D, n = 3 animals/time point.

Example-47: Rodent Pharmacokinetic Study

Male Wistar rats (260±50 g) were used as experimental animals. Animals were housed individually in polypropylene cage. Two days prior to study, male Wistar rats were anesthetized with isoflurane for surgical placement of jugu- Example-48: Rodent Brain Penetration Study Male Wistar rats (260±40 g) were used as experimental animals. Three animals were housed in each cage. Animals were given water and food ad libitum throughout the experiment and maintained on a 12 h light/dark cycle.

Brain penetration was determined in discrete manner in rats. One day prior to dosing, male Wistar rats were acclimatized and randomly grouped according to their body weight. At each time point (0.50, 1 and 2 h), n=3 animals were used.

The test compounds were suitably preformulated and administered orally at (free base equivalent) 3 mg/kg. Blood samples were removed via cardiac puncture under isoflurane anesthesia. The animals were sacrificed to collect brain tissue. Plasma was separated and brain samples were homogenized. Plasma and brain homogenates were stored frozen at −20° C. until analysis. The concentrations of the test compounds in plasma and brain were determined using LC-MS/MS method.

The test compounds were quantified in plasma and brain homogenate by qualified LC-MS/MS method using suitable extraction technique in the calibration range of 1-500 ng/mL. Study samples were analyzed using calibration samples in the batch and quality control samples spread across the batch. Extent of brain-plasma ratio ($C_{brain}/C_{plasma}$) was calculated.

TABLE 7

Blood-Brain Penetration data of the test compounds*

| Example No. | Rat Brain Penetration ($C_{brain}/C_{plasma}$) at 3 mg/kg, p.o. @ 1 h |
|---|---|
| 2 | 0.49 ± 0.08 |
| 4 | 2.14 ± 0.88 |
| 5 | 1.06 ± 0.46 |
| 9 | 0.40 ± 0.13 |
| 11 | 0.09 ± 0.16 |
| 27 | 1.21 ± 0.13 |
| 29 | 2.73 ± 0.23 |

*Fed male Wistar rats were used; Vehicle used is water for injection. Values are mean ± S.D, n = 3 animals/time point.

Example-49: Amphetamine-Induced Hyperlocomotion

Male Sprague Dawley rats of 230-280 g body weight were used. Rats were weighed and randomized according to their body weights. Following day, the rats were brought to the laboratory 1 h prior to test. In the morning session, rats were habituated to open field arena for 15 min. Test compound/vehicle and amphetamine/vehicle were administered 30 min prior to the trial. After the post-dose interval, rats were placed in the open field and locomotion was recorded for a period of 15 min. Amphetamine-induced hyperlocomotion models positive symptoms of schizophrenia.

TABLE 8

Amphetamine antagonism data of the test compounds

| Example No. | Dose | Inference |
|---|---|---|
| 2 | 3 mg/kg, p.o. | Active |
| 27 | 3 mg/kg, p.o. | Active |

Example-50: Forced Swim Test

Male Swiss albino mice having weight range of 30-40 g were used. Mice were dosed with vehicle or test compound. Thirty min after treatment, animals were individually placed inside the plexiglass cylinder (40 cm height×17 cm width) for 6 min. The depth of water (24±1° C.) was maintained at 18 cm. The immobility of the mice during the last 4 min were recorded in the 6 min trial. Forced swim test assesses antidepressant like effects of test compounds.

TABLE 9

Mice forced swim test data of the test compounds

| Example No. | Dose | Inference |
|---|---|---|
| 2 | 10 mg/kg, p.o. | Active |

Example-51: MK-801-Induced Amnesia in Novel Object Recognition Task (NORT)

Male Wistar rats of 230-280 g body weight were used. Rats were weighed and randomized according to their body weights. On day 1, animals were habituated to the arenas for 45 min. On day 2, 30 min before the trial-1 animals were administered with vehicle (WFI) or test compound and 20 min before the trial-1 the animals were administered with MK-801 0.03 mg/kg, i.p. Trial-1 is familiarization task in the arena with two similar kind of silver color flasks of same dimensions for a period of 3 min. After an inter trial interval of 90 min animals were subjected to recognition task in the arena with one silver and one violet bottle for a period of 3 min. Time spent by the rats with either familiar or novel objects was noted and analyzed. MK-801-induced amnesia in novel object recognition task models cognitive deficits associated with schizophrenia.

TABLE 10

MK-801-induced amnesia in NORT data of the test compound

| Example No. | Dose | Inference |
|---|---|---|
| 2 | 0.3 mg/kg, p.o. | Active |

Example-52: DOI-induced Head Twitch Response

On day 1 male Wistar rats (220-250 g) were habituated in a circular cylinder for a period of 15 min. On day 2, the rats were brought to the experimental room 30 min prior to the experiment. All the animals were administered with respective formulations i.e. vehicle or test compound 30 min prior to DOI or vehicle administration. Immediately following DOI or vehicle administration, the animals were kept in the circular cylinder for a period of 10 min to score the head twitches. Compounds which act as $5\text{-}HT_{2A}$ antagonists attenuate DOI-induced head twitches.

TABLE 11

DOI-induced Head twitch response data of the test compound

| Example No. | Dose | Inference |
|---|---|---|
| 2 | 3.0 mg/kg, s.c. | Active |

Example-53: Resident-Intruder Task

Male CD1 mice of weight 20-35 g (Resident) and 15-25 g (Intruder) were used. Resident mice were habituated individually with an ovariectomized female mouse in each cage and intruders were habituated socially for 1 week.

β-estradiol at a dose of 0.2 mg/kg, s.c. was administered to female mice during habituation. On day 1 and day 2, intruder was exposed to resident mouse in resident's home cage for a period of 10 min and duration of attack was measured. During this exposure, female mouse were removed from the cage. On day 4 from initial exposure, animals were randomized based on their duration of attacking and administered respective treatments. Test compound and vehicle were administered 30 min prior to the trial. After post dose interval resident mice were exposed to same intruder for 10 min and duration of attack was recorded. Resident intruder task models aggressive behavior.

TABLE 12

Resident intruder task data of the test compound

| Example No. | Dose | Inference |
|---|---|---|
| 2 | 3.0 mg/kg, p.o. | Active |

Example-54: Reserpine-Induced Dihydroxyphenylalanine (DOPA) Accumulation Assay in Rat Striatum Reserpine (5.0 mg/kg, s.c.) was injected, after which rats were fasted for 18 h before sacrifice. Example-2/vehicle and apomorphine (a dopamine receptor agonist, 0.1 mg/kg, s.c) were administered 1.0 and 0.6 h respectively before sacrifice. NSD-1015 (a DOPA decarboxy lase inhibitor, 100 mg/kg, s.c.) was injected 0.5 h before sacrifice. Each rat was sacrificed and the striatum was dissected out of the whole brain on ice. Each striatum was weighed and homogenized individually in buffer containing 0.01 N hydrochloric acid and 0.2 mg/ml L-cysteine. Supernatants were subjected for quantification of DOPA using HPLC coupled to electrochemical detector.

Example-2 (10 mg/kg, s.c.) produced no change in reserpine elevated DOPA levels suggesting non-agonistic nature at dopamine receptor. Whereas, apomorphine, a dopamine receptor agonist produced significant decrease in reserpine-induced DOPA accumulation (Figure-1). However, pre-treatment of Example-2 blocked the effects of apomorphine.

Results from this in vivo profiling assay suggest that Example-2 acts as a dopamine receptor antagonist in vivo.

Example-55: Modulation in Dopamine and Norepinephrine Levels in Prefrontal Cortex and Striatum of Male Wistar Rats Male Wistar rats (240-300 g body weight) were stereotaxically implanted with a microdialysis guide cannula in prefrontal cortex (PFC; AP: +3.2 mm, ML: −0.5 mm, DV: −1.0 mm) or Striatum (AP −0.2 mm, ML −3.0 mm, DV −3.0 mm) under isoflurane anesthesia. Co-ordinates were taken according to atlas for the rat brain (Paxinos and Watson 2004) with reference points taken from bregma and vertical from the skull. The rats were allowed to recover individually for four days in a round bottom Plexiglass bowl with free access to feed and water.

After surgical recovery of 4 days, rats were connected to dual quartz lined two-channel liquid swivel (Instech, UK) on a counter balance lever arm, which allowed unrestricted movements of the animal. 16 h before start of the study, a pre-equilibrated microdialysis probe (4 mm dialysis membrane) was inserted into PFC or striatum through the guide cannula. On the day of study, probe was perfused with artificial cerebrospinal fluid at a flow rate of 1.5 L/min and a stabilization period of 2 h was maintained. Four basal samples were collected at 30 min intervals prior to the treatment of Example-2 (3 or 10 mg/kg, p.o.) or vehicle. Dialysate samples were collected for an additional period of 4 h post treatment and stored below −50° C. prior to analysis.

Dopamine and norepinephrine levels in dialysate were quantified using LC-MS/MS method. Microdialysis data was plotted as percent change from mean dialysate basal concentrations with 100% defined as the average of four pre-dose values. The percent change in neurotransmitter levels was analyzed using two-way analysis of variance (time and treatment), followed by Bonferroni's post-test. Statistical significance was considered at a p-value less than 0.05.

Figure 2:
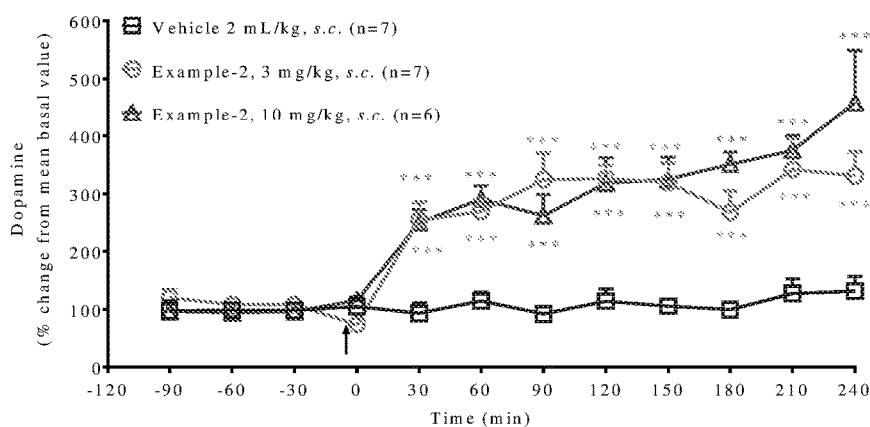
FIG. 2: Modulation in dopamine levels in prefrontal cortex

Treatment with Example-2 produced an increase in cortical dopamine levels in prefrontal cortex with mean maximum increase of 326±24% and 458±91% at 3 and 10 mg/kg, s.c. respectively (Figure-2)

Figure 3:
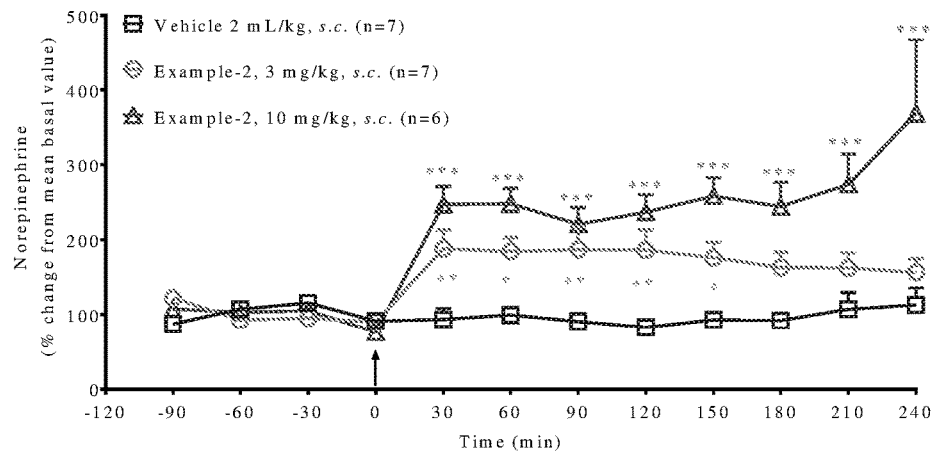
FIG. 3: Modulation in norepinephrine levels in prefrontal cortex

Treatment with Example-2 produced an increase in cortical norepinephrine levels in prefrontal cortex with mean maximum increase of 187±30% and 368±99% at 3 and 10 mg/kg, s.c. respectively (Figure-3)

Figure 4:
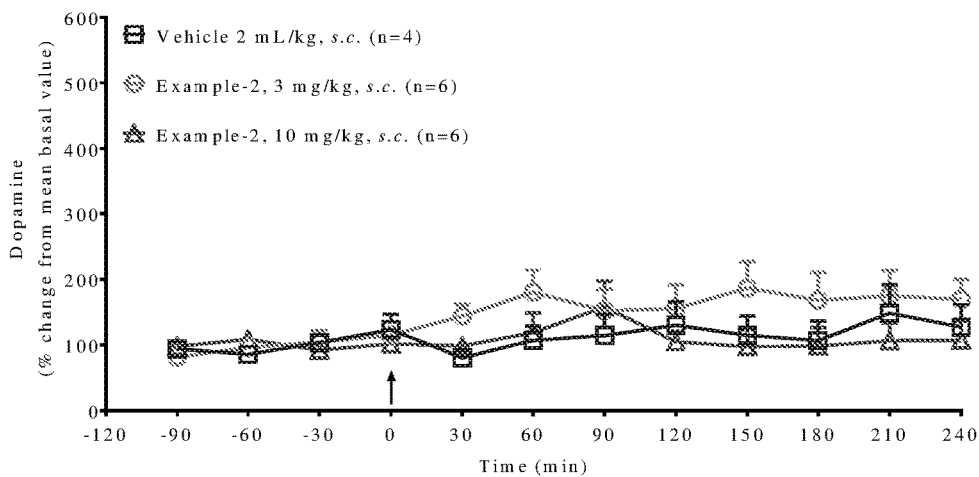
FIG. 4: Modulation in dopamine levels in striatum

Treatment with Example-2 produced no change in dopamine levels in striatum (Figure-4).

Results from these studies indicate that Example-2 produces a significant increase in dopamine and norepinephrine in prefrontal cortex and does not increase dopamine levels in the striatum suggesting it may have utility in the treatment of neuropsychiatric disorders with no propensity to induce psychostimulation.

Example-56: Effect on Sleep/Wake Profile in Male Wistar Rats

Male Wistar rats were anesthetized with isoflurane (Baxter India Private Limited: 4% in oxygen for induction; 2% for maintenance) and were fixed into the stereotaxic frame (Stoelting, Illinois, USA) to perform surgery. An incision was made to reveal bregma from which coordinates were taken. Telemetric transmitter (Model F40-EET; DSI, St. Paul, MN, USA) was implanted into intraperitoneal cavity of the rats and leads were tunneled subcutaneously to the skull. One pair of electrodes were implanted epidurally into the frontal cortex region using stainless steel screws (CMA Microdialysis, Stockholm, Sweden) at coordinates of AP +3.2 mm, ML ±3.0 mm (Paxinos and Watson 2004) for recording of EEG and electrodes were fixed to the skull with dental acrylic cement (Dentalon® plus). The second set of lead wires were implanted into the neck nuchal muscle to record electromyogram (EMG). After a surgical recovery of minimum 3 weeks, animals were acclimatized to the handling procedures and were given a mock dosing for 3 days before the first experimental day.

One hour prior to lights-off, transmitter was switched on using a magnet and animals were transferred on to the receiver along with the home cage. Recording was carried out using Ponemah (Version 5.2; DSI, St. Paul, MN, USA) software. Fifteen minutes prior to lights-off, animals were treated with vehicle or Example-2 (10 mg/kg, p.o.) in a cross-over design allowing washout period of one week between treatments. Recording was continued overnight post treatment. EEG and EMG were collected as primary signals and sampled at 500 Hz. Whereas, temperature and activity were sampled at 250 Hz. The data was stored for off-line analysis using NeuroScore software (Version 3.0; DSI, St. Paul, MN, USA).

The amount of time spent in wake was determined for every 30 min and comparison between treatments was done using Bonferroni's post test.

Figure 5:
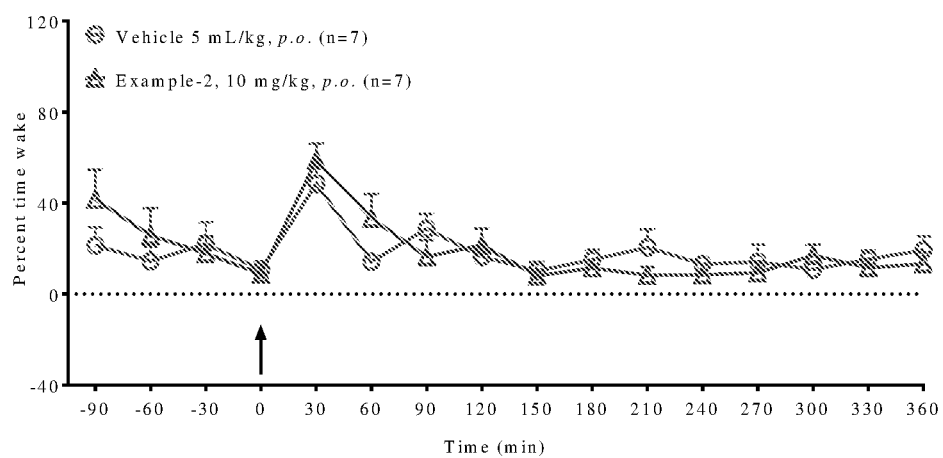
FIG. 5: Effect on Sleep/Wake

Treatment with Example-2 (10 mg/kg, p.o.) produced no change in percent time wake of male Wistar rats (Figure-5) suggesting Example-2 may not produce sleep-related side effects at therapeutically effective dose range.

Example-57: Tardive Dyskinesia Test

Rats weighing 200-230 g were acclimatized to the plexiglass observation cages (30×20×30 cm) equipped with mirrors for 5 min. After acclimatization, basal vacuous chewing movements (VCMs) and tongue protrusions (TPs) of the rats were quantified manually for 5 min. Rats were randomized based on the basal readings. Rats received a single dose of sesame oil (vehicle treatment) or haloperidol decanoate (38 mg/kg, i.m. positive control). Example-2, 10 mg/kg, p.o. (5 mg twice a day) was administered for 4 weeks. VCMs and TPs were scored on weekly basis for 4 weeks. Tardive dyskinesia is a side effect of antipsychotic medications.

TABLE 13

Tardive dyskinesia test data of the test compound

| Example No. | Dose | Inference |
|---|---|---|
| Haloperidol decanoate | 38 mg/kg, i.m. | Increased number of VCMs and TPs significantly compared to vehicle group at all the tested weeks. Haloperidol decanoate caused tardive dyskinesia |
| 2 | 10 mg/kg, p.o. | Example-2 did not show tardive dyskinesia like symptoms at 10 mg/kg, p.o. |

Example-58: Rotarod Test

Male Wistar rats of 200-280 g body weight were used. Rats were weighed and randomized according to their body weights. The animals were habituated on a rotating rod (4 rpm) for 4 times. Animals which successfully stayed on the rotating rod for 60 seconds (out of 4 trials per animal) were selected for further study. Animals which did not complete 60 seconds trial within 4 choices were rejected from the study. A single trial was carried out on the next day. Animals that were able to stay on the rotating rod for 60 seconds were chosen for further study. Animals were administered with test compound or vehicle 60 min prior to the trial. The latency to fall from the rotating rod was noted. Rotarod test assesses effects of test compound on motor functions.

TABLE 14

Rotarod test data of the test compound

| Example No. | Dose | Inference |
|---|---|---|
| 2 | 30 mg/kg p.o. | No motor incoordination side effects |

We claim:

1. A compound of formula (I):

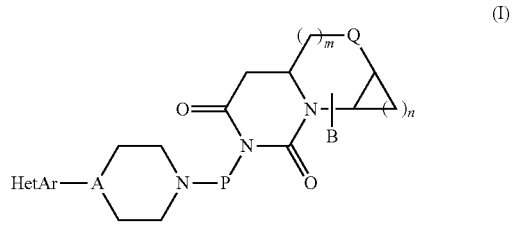

or a pharmaceutically acceptable salt or stereoisomer thereof, wherein:

HetAr is:

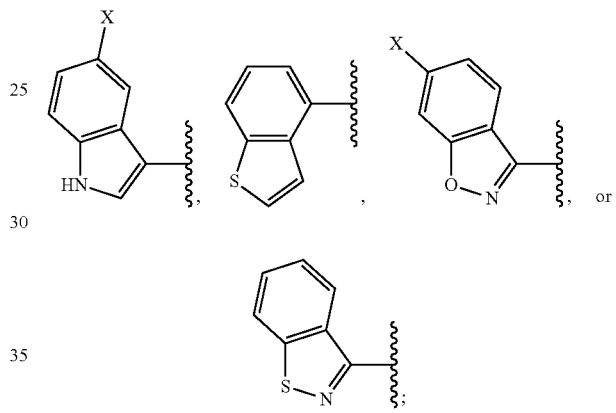

X is H, halogen, or O(alkyl);

⁓ is the point of attachment to A;

A is CH or N;

P is —(CH$_2$)$_b$— or

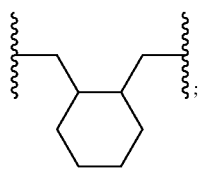 [SMILES: *CC1CCCCC1C*]

Q is —CH$_2$—, —NH—, —N(alkyl)-, —N[C(O)R]—, —N[C(O)OR]—, or —O—;

R is alkyl, alkyl-O(alkyl), alkyl(aryl), or cycloalkyl;

b is 2, 3, 4, 5, or 6;

m is 0 or 1; and n is 0 or 1;

with the provisos that:

(1) if Q is —CH$_2$—, then each B is independently H, halogen, or O(alkyl); and (2) if Q is —NH—, —N(alkyl)-, —N[C(O)R]—, —N[C(O)OR]—, or —O—, then B is absent.

2. The compound as claimed in claim 1, or a pharmaceutically acceptable salt thereof, wherein the compound, or pharmaceutically acceptable salt thereof, is selected from the group consisting of:
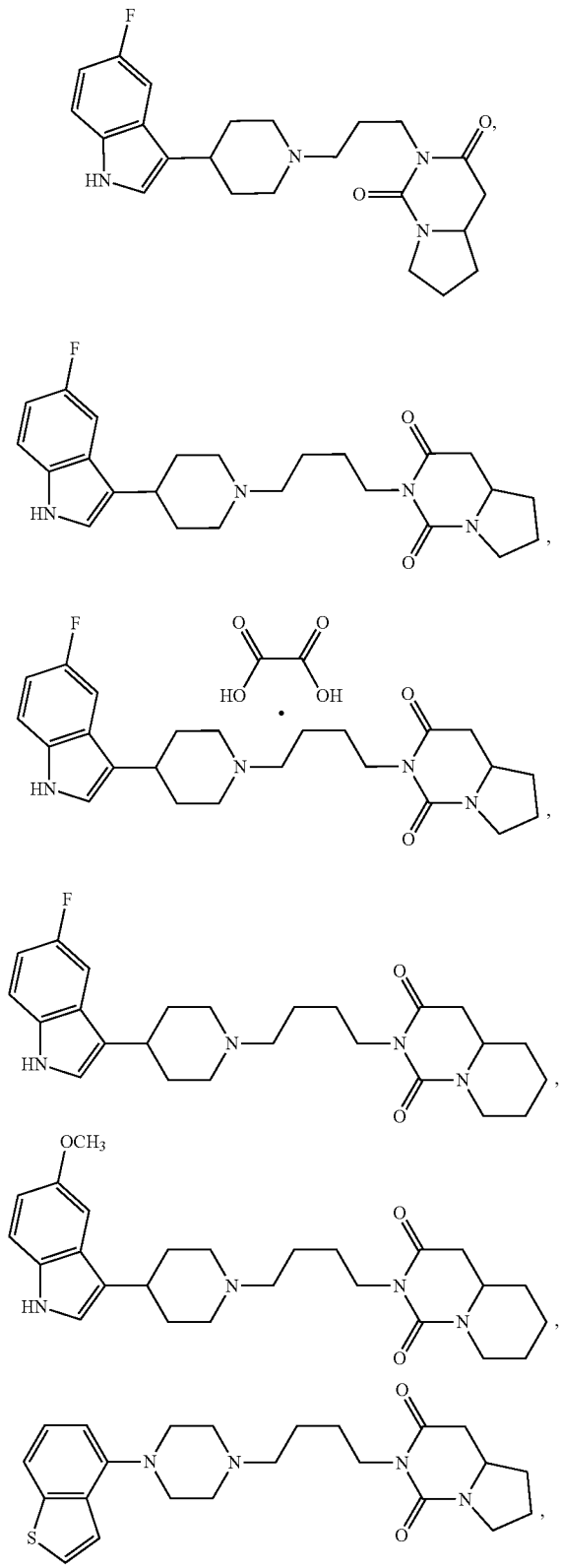
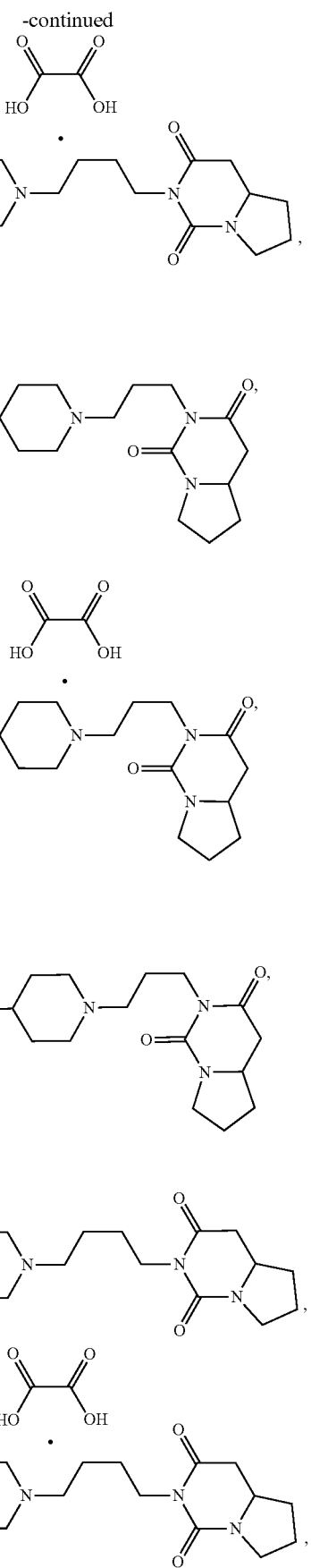
-continued

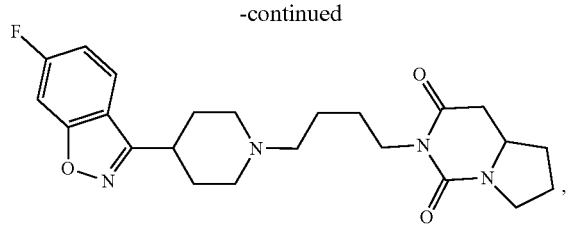
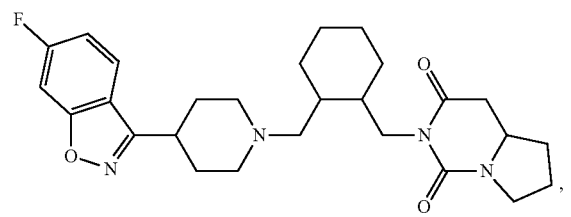
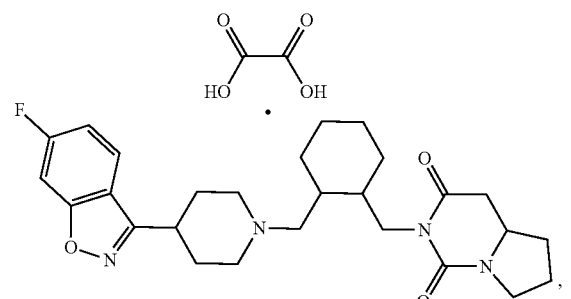
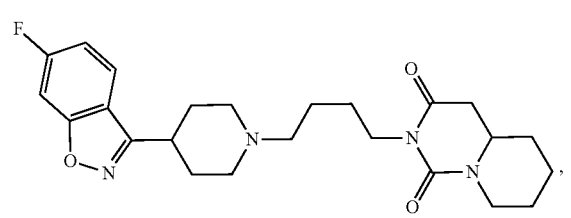
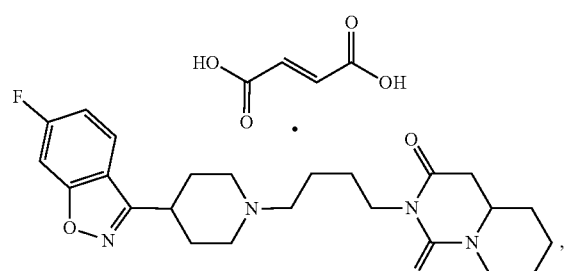
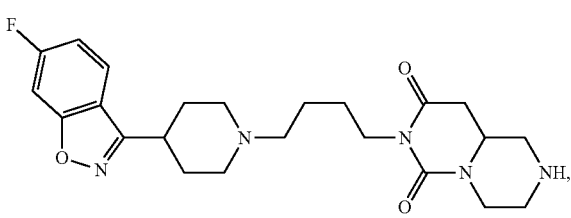
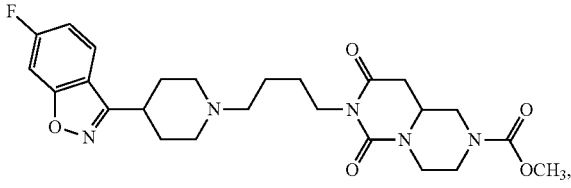
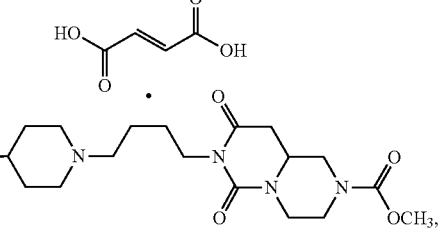
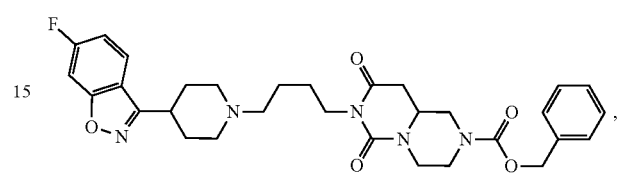
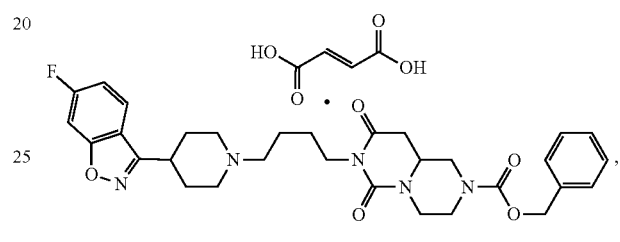
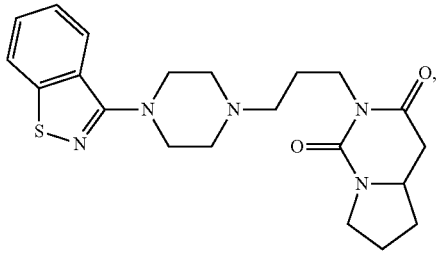
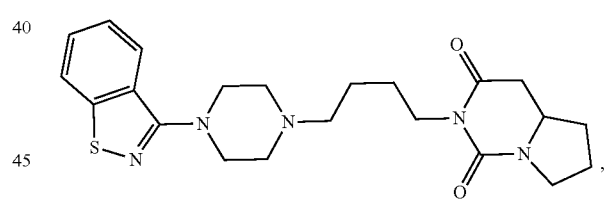
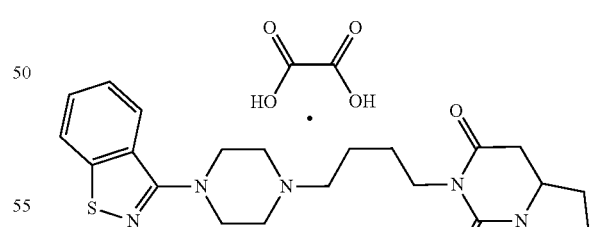
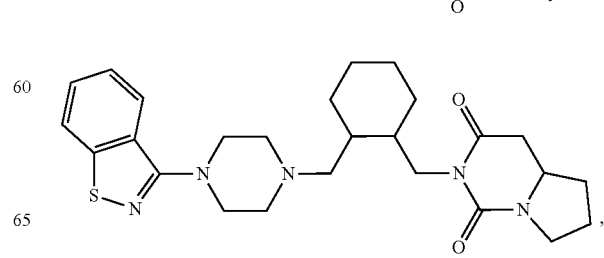

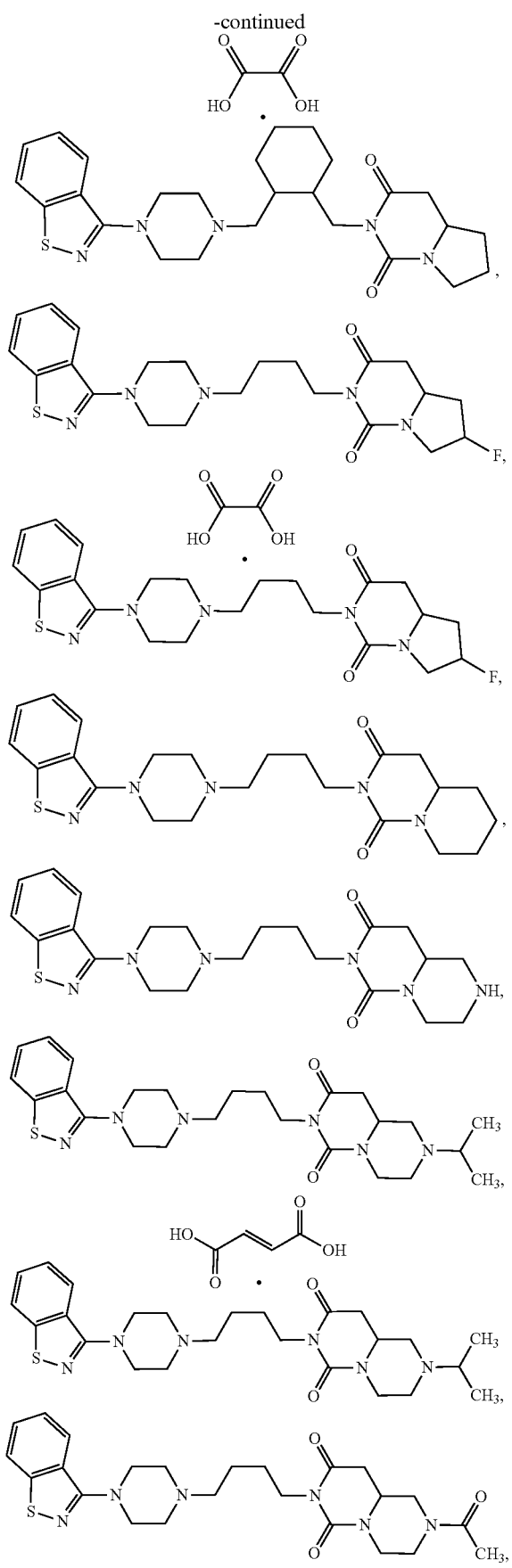
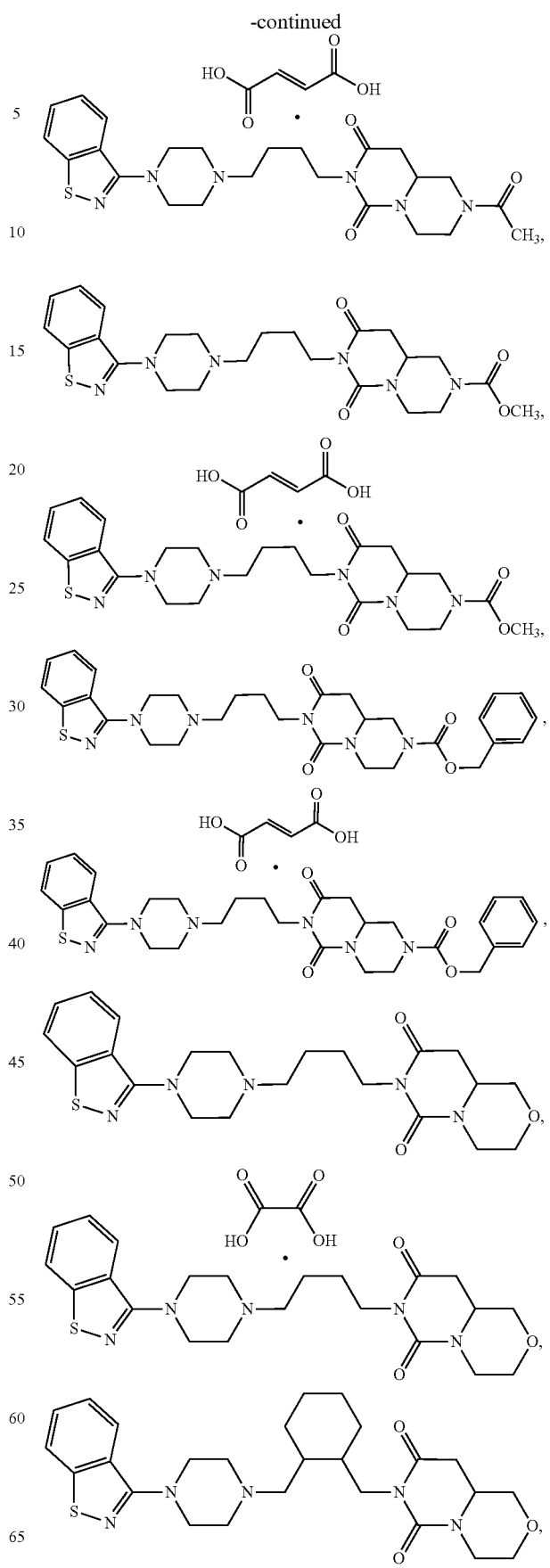

-continued

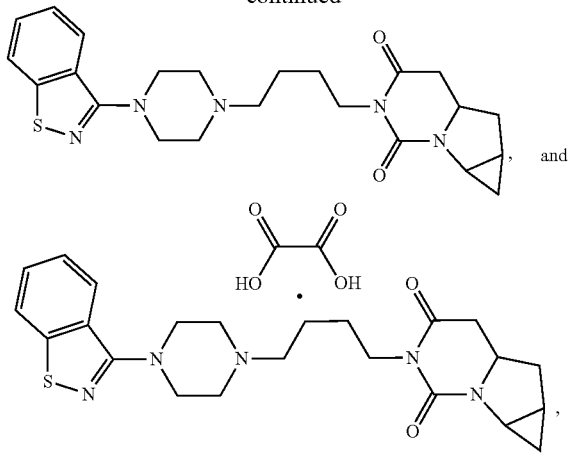

or a stereoisomer thereof.

3. A pharmaceutical composition comprising at least one pharmaceutically acceptable excipient and the compound as claimed in claim 1, or a pharmaceutically acceptable salt or stereoisomer thereof.

4. A method for inhibiting 5-hydroxytryptamine receptor 1A (5-$HT_{1A}$) activity, 5-hydroxytryptamine receptor 2A (5-$HT_{2A}$) activity, 5-hydroxytryptamine receptor 7 (5-$HT_7$) activity, dopamine receptor ($D_2$) activity, or serotonin transporter (SERT) activity in a patient in need thereof, wherein the method comprises the step of administering to the patient a therapeutically effective amount of the compound as claimed in claim 1, or a pharmaceutically acceptable salt or stereoisomer thereof.

5. The method as claimed in claim 4, wherein the patient has a central nervous system condition or central nervous system disorder selected from the group consisting of an amnestic disorder, an anxiety disorder, attention-deficit/hyperactivity disorder, autism disorder, a cognitive disorder, a depressive disorder, a drug dependency, an emotional disturbance, a mood disorder, a movement disorder, a neuropsychiatric symptom associated with dementia, a psychotic disorder, and a sleep disorder.

6. The method as claimed in claim 5, wherein the cognitive disorder is a cognitive deficit associated with schizophrenia.

7. The method as claimed in claim 5, wherein the movement disorder is Tourette syndrome.

8. The method as claimed in claim 5, wherein the neuropsychiatric symptom associated with dementia is aggression or agitation.

9. The method as claimed in claim 5, wherein the psychotic disorder is selected from the group consisting of anhedonia, bipolar disorder type 1, bipolar disorder type 2, borderline personality disorder, delirium, dissociative disorder, hysteria, and schizophrenia.

10. A method for inhibiting 5-hydroxytryptamine receptor 1A (5-$HT_{1A}$) activity, 5-hydroxytryptamine receptor 2A (5-$HT_{2A}$) activity, 5-hydroxytryptamine receptor 7 (5-$HT_7$) activity, dopamine receptor ($D_2$) activity, or serotonin transporter (SERT) activity in a patient in need thereof, wherein the method comprises the step of administering to the patient a therapeutically effective amount of the pharmaceutical composition as claimed in claim 3.

11. The method as claimed in claim 10, wherein the patient has a central nervous system condition or central nervous system disorder selected from the group consisting of an amnestic disorder, an anxiety disorder, attention-deficit/hyperactivity disorder, autism disorder, a cognitive disorder, a depressive disorder, a drug dependency, an emotional disturbance, a mood disorder, a movement disorder, a neuropsychiatric symptom associated with dementia, a psychotic disorder, and a sleep disorder.

12. The method as claimed in claim 11, wherein the cognitive disorder is a cognitive deficit associated with schizophrenia.

13. The method as claimed in claim 11, wherein the movement disorder is Tourette syndrome.

14. The method as claimed in claim 11, wherein the neuropsychiatric symptom associated with dementia is aggression or agitation.

15. The method as claimed in claim 11, wherein the psychotic disorder is selected from the group consisting of anhedonia, bipolar disorder type 1, bipolar disorder type 2, borderline personality disorder, delirium, dissociative disorder, hysteria, and schizophrenia.

* * * * *